US012661190B2

(12) United States Patent　　(10) Patent No.:　US 12,661,190 B2
Avall et al.　　(45) Date of Patent:　Jun. 23, 2026

(54) SYSTEMS AND METHODS FOR FACILITATING MOVEMENT EFFICIENCY OF A MEDICAL DEVICE WITHIN A BODILY CAVITY

(71) Applicant: KARDIUM INC., Burnaby (CA)

(72) Inventors: Stefan Avall, Vancouver (CA); Saar Moisa, Vancouver (CA)

(73) Assignee: KARDIUM INC., Burnaby (CA)

( * ) Notice: Subject to any disclaimer, the term of this patent is extended or adjusted under 35 U.S.C. 154(b) by 131 days.

(21) Appl. No.: 18/542,972

(22) Filed: Dec. 18, 2023

(65) Prior Publication Data

US 2024/0252258 A1　　Aug. 1, 2024

Related U.S. Application Data

(60) Provisional application No. 63/441,296, filed on Jan. 26, 2023.

(51) Int. Cl.
　*A61B 34/30*　　(2016.01)
　*A61B 18/00*　　(2006.01)
　　　(Continued)

(52) U.S. Cl.
　CPC .............. *A61B 34/25* (2016.02); *A61B 18/00* (2013.01); *A61B 34/20* (2016.02); *G06T 1/0007* (2013.01);
　　　(Continued)

(58) Field of Classification Search
　CPC ......... A61B 34/00; A61B 34/25; A61B 18/00; A61B 2034/105; A61B 2034/2065; A61B 2034/254
　See application file for complete search history.

(56) References Cited

U.S. PATENT DOCUMENTS 5,697,377　A　　12/1997　Wittkampf
6,546,270　B1　　4/2003　Goldin et al.
　　　(Continued)

FOREIGN PATENT DOCUMENTS

EP　　　3372186　A1　　9/2018
EP　　　3422297　A1　　1/2019
　　　(Continued)

OTHER PUBLICATIONS

Non-Final Office Action issued in copending U.S. Appl. No. 18/536,641 mailed Jul. 24, 2024.

(Continued)

*Primary Examiner* — Vi X Nguyen
(74) *Attorney, Agent, or Firm* — ROSSI, KIMMS & McDOWELL LLP

(57)　　　　　ABSTRACT

A data processing device system may be configured to cause display of a three-dimensional graphical representation of a first volume within a bodily cavity, cause the three-dimensional graphical representation to be annotated to include a graphical annotation set, and cause, at least in response to the annotation, the three-dimensional graphical representation to add an anatomical feature graphical representation. A data processing device system may be configured cause display of a particular graphical representation including a graphical representation of a particular volume within a cardiac cavity, cause the particular graphical representation to be annotated to include a graphical annotation set having a particular graphical attribute set, and cause, in response to a movement of a medical device, a changing of the particular graphical attribute set while the graphical annotation set graphically remains in correspondence with a same location in real-world three-dimensional space.

35 Claims, 21 Drawing Sheets

(51) Int. Cl.

| | |
|---|---|
| *A61B 34/00* | (2016.01) |
| *A61B 34/20* | (2016.01) |
| *G06T 1/00* | (2006.01) |
| *G16H 10/60* | (2018.01) |
| *A61B 34/10* | (2016.01) |

(52) U.S. Cl.
CPC .... *G16H 10/60* (2018.01); *A61B 2018/00375* (2013.01); *A61B 2018/00577* (2013.01); *A61B 2034/105* (2016.02); *A61B 2034/2055* (2016.02); *A61B 2034/2065* (2016.02); *A61B 2034/254* (2016.02); *G06T 2207/30048* (2013.01)

(56) References Cited

U.S. PATENT DOCUMENTS

| | | | |
|---|---|---|---|
| 7,720,520 | B2 | 5/2010 | Willis |
| 8,123,721 | B2 | 2/2012 | Tegg |
| 8,825,144 | B2 | 9/2014 | Starks |
| 8,906,011 | B2 | 12/2014 | Gelbart |
| 8,920,411 | B2 | 12/2014 | Gelbart et al. |
| 9,198,592 | B2 | 12/2015 | Reinders |
| 9,452,016 | B2 | 9/2016 | Moisa |
| 9,492,227 | B2 | 11/2016 | Lopes |
| 9,980,653 | B2 | 5/2018 | Lichtenstein et al. |
| 10,368,936 | B2 | 8/2019 | Brewster et al. |
| 10,814,099 | B2 | 10/2020 | Funk |
| 2007/0265526 | A1 | 11/2007 | Govari |
| 2008/0085042 | A1 | 4/2008 | Trofimov et al. |
| 2013/0035576 | A1 | 2/2013 | O'Grady et al. |
| 2016/0000357 | A1 | 1/2016 | Harlev et al. |
| 2017/0143201 | A1* | 5/2017 | Claude ................... A61B 1/05 |
| 2017/0202469 | A1 | 7/2017 | Scharf |
| 2017/0330487 | A1 | 11/2017 | Harlev |
| 2019/0269367 | A1* | 9/2019 | Reinders ............... A61N 1/362 |
| 2020/0085329 | A1 | 3/2020 | Markovitz |
| 2021/0353370 | A1 | 11/2021 | Moisa |

FOREIGN PATENT DOCUMENTS

| | | | |
|---|---|---|---|
| EP | 4046574 | A1 | 8/2022 |
| WO | 2012100184 | A2 | 7/2012 |
| WO | 2012100185 | A2 | 7/2012 |
| WO | 2017100902 | A1 | 6/2017 |

OTHER PUBLICATIONS

Non-Final Office Action issued in copending U.S. Appl. No. 18/536,492 mailed Jul. 26, 2024.

Amendment filed in copending U.S. Appl. No. 18/536,492 on Aug. 30, 2024.

Preliminary Amendment filed in copending U.S. Appl. No. 18/536,602 on Aug. 30, 2024.

Preliminary Amendment filed in copending U.S. Appl. No. 18/536,569 on Aug. 30, 2024.

Office Action issued in copending U.S. Appl. No. 18/536,569 mailed Sep. 6, 2024.

Amendment filed in copending U.S. Appl. No. 18/536,641 on Sep. 6, 2024.

Notice of Allowance issued in copending U.S. Appl. No. 17/389,972, mailed Dec. 27, 2023.

Bhakta. "Principles of Electroanatomic Mapping." Indian Pacing and Electrophysiology Journal. 2008: 32-50. vol. 8, No. 1.

International Search Report issued in Intl. Appln. No. PCT/CA2020/050061 mailed Apr. 23, 2020.

Written Opinion issued in Intl. Appln. No. PCT/CA2020/050061 mailed Apr. 23, 2020.

Kottkamp et al. "Global multielectrode contact mapping plus ablation with a single catheter: Preclinical and preliminary experience in humans with atrial fibrillation." Journal of Cardiovascular Electrophysiology. 2017:1-10.

Mounsey. "A novel multielectrode combined mapping and ablation basket catheter: A future player in the atrial fibrillation ablation space?" Journal of Cardiovascular Electrophysiology. 2017:1-2.

Extended European Search Report issued in European Appln. No. 20756459.2 mailed Oct. 13, 2022.

Ideker et al. "A Computerized Method for the Rapid Display of Ventricular Activation During the Intraoperative Study of Arrhythmias" Journal Circulation, Mar. 1979. pp. 449-458, vol. 59, No. 3.

Non-Final Office Action issued in copending U.S. Appl. No. 17/389,972 mailed May 9, 2023.

Response filed in copending U.S. Appl. No. 17/389,972 on Jul. 26, 2023.

Final Office Action issued in copending U.S. Appl. No. 17/389,972 mailed Sep. 6, 2023.

Amendment After Final Action filed in copending U.S. Appl. No. 17/389,972 on Nov. 6, 2023.

Moisa. Copending U.S. Appl. No. 18/536,492, filed Dec. 12, 2023.

Moisa. Copending U.S. Appl. No. 18/536,569, filed Dec. 12, 2023.

Moisa. Copending U.S. Appl. No. 18/536,602, filed Dec. 12, 2023.

Moisa. Copending U.S. Appl. No. 18/536,641, filed Dec. 12, 2023.

Avall et al. Copending U.S. Appl. No. 18/543,301, filed Dec. 18, 2023.

Amendment filed in U.S. Appl. No. 18/536,569 on Dec. 4, 2024.

Response After Final Action filed in U.S. Appl. No. 18/536,641 on Dec. 23, 2024.

Communication Under Rule 71(3) EPC issued in European Appln. No. 20756459.2 mailed Jan. 10, 2025.

Second Response After Final Action filed in U.S. Appl. No. 18/536,641 on Jan. 28, 2025.

Notice of Allowance issued in U.S. Appl. No. 18/536,569 mailed Jan. 15, 2025.

Notice of Allowance issued in U.S. Appl. No. 18/536,641 mailed Feb. 19, 2025.

Notice of Allowance issued in U.S. Appl. No. 18/536,492 mailed Oct. 18, 2024.

Office Action issued in U.S. Appl. No. 18/536,641 mailed Oct. 28, 2024.

Extended European Search Report issued in European Application No. 25182875.2 mailed Sep. 12, 2025.

\* cited by examiner

Figure 8A:
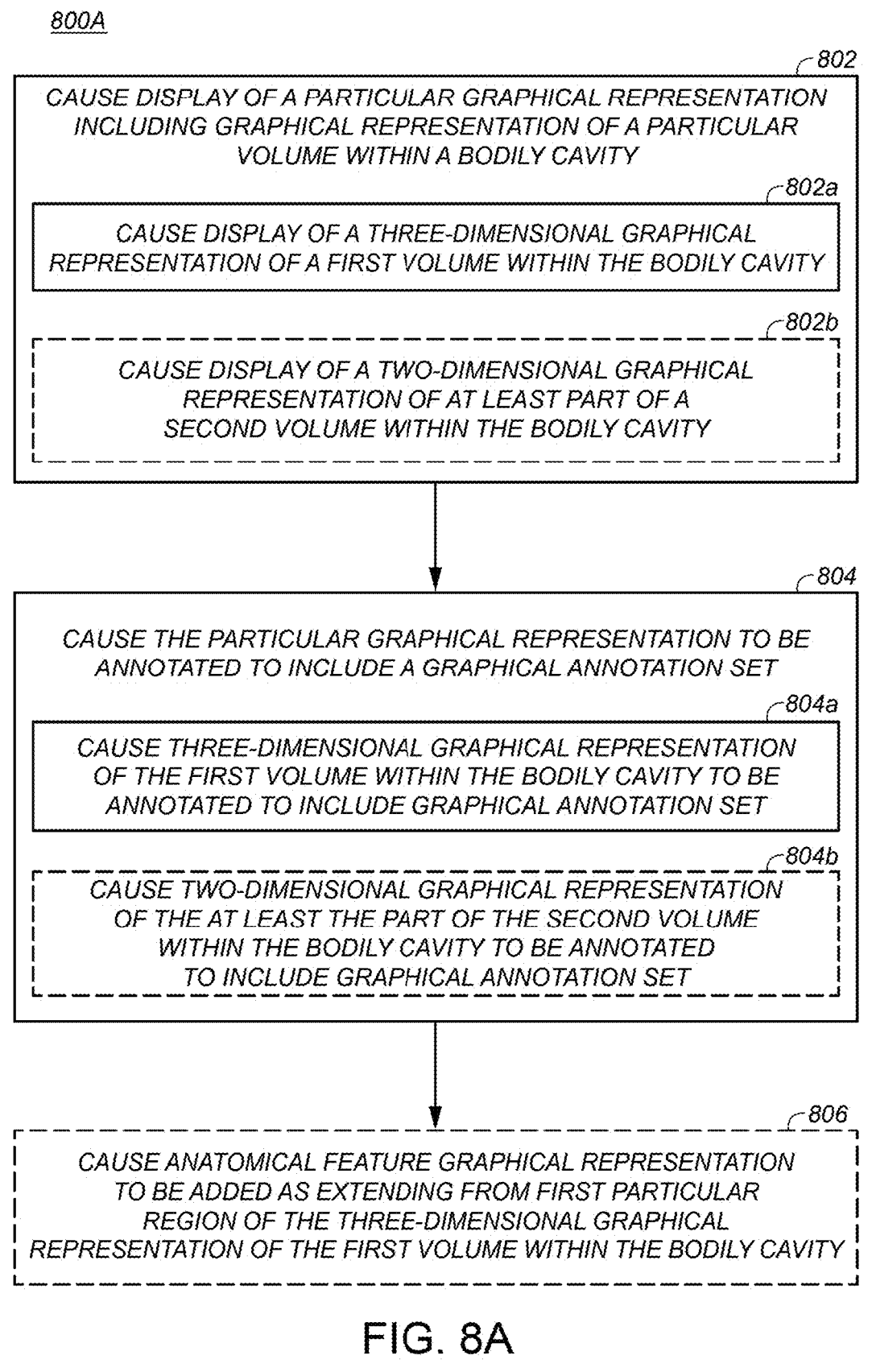

_800A_

┌─────────────────────────────────────────────────────────────────┐ ⌐802
│ *CAUSE DISPLAY OF A PARTICULAR GRAPHICAL REPRESENTATION*           │
│ *INCLUDING GRAPHICAL REPRESENTATION OF A PARTICULAR*               │
│ *VOLUME WITHIN A BODILY CAVITY*                                    │
│   ┌───────────────────────────────────────────────────────┐ ⌐802a │
│   │ *CAUSE DISPLAY OF A THREE-DIMENSIONAL GRAPHICAL*         │      │
│   │ *REPRESENTATION OF A FIRST VOLUME WITHIN THE BODILY CAVITY* │   │
│   └───────────────────────────────────────────────────────┘      │
│   ┌───────────────────────────────────────────────────────┐ ⌐802b │
│   │ *CAUSE DISPLAY OF A TWO-DIMENSIONAL GRAPHICAL*          │      │
│   │ *REPRESENTATION OF AT LEAST PART OF A*                  │      │
│   │ *SECOND VOLUME WITHIN THE BODILY CAVITY*                │      │
│   └───────────────────────────────────────────────────────┘      │
└─────────────────────────────────────────────────────────────────┘

┌─────────────────────────────────────────────────────────────────┐ ⌐804
│ *CAUSE THE PARTICULAR GRAPHICAL REPRESENTATION TO BE*             │
│ *ANNOTATED TO INCLUDE A GRAPHICAL ANNOTATION SET*                 │
│   ┌───────────────────────────────────────────────────────┐ ⌐804a │
│   │ *CAUSE THREE-DIMENSIONAL GRAPHICAL REPRESENTATION*       │      │
│   │ *OF THE FIRST VOLUME WITHIN THE BODILY CAVITY TO BE*     │      │
│   │ *ANNOTATED TO INCLUDE GRAPHICAL ANNOTATION SET*          │      │
│   └───────────────────────────────────────────────────────┘      │
│   ┌───────────────────────────────────────────────────────┐ ⌐804b │
│   │ *CAUSE TWO-DIMENSIONAL GRAPHICAL REPRESENTATION*        │      │
│   │ *OF THE AT LEAST THE PART OF THE SECOND VOLUME*         │      │
│   │ *WITHIN THE BODILY CAVITY TO BE ANNOTATED*             │      │
│   │ *TO INCLUDE GRAPHICAL ANNOTATION SET*                  │      │
│   └───────────────────────────────────────────────────────┘      │
└─────────────────────────────────────────────────────────────────┘

┌─────────────────────────────────────────────────────────────────┐ ⌐806
│ *CAUSE ANATOMICAL FEATURE GRAPHICAL REPRESENTATION*               │
│ *TO BE ADDED AS EXTENDING FROM FIRST PARTICULAR*                  │
│ *REGION OF THE THREE-DIMENSIONAL GRAPHICAL*                       │
│ *REPRESENTATION OF THE FIRST VOLUME WITHIN THE BODILY CAVITY*     │
└─────────────────────────────────────────────────────────────────┘

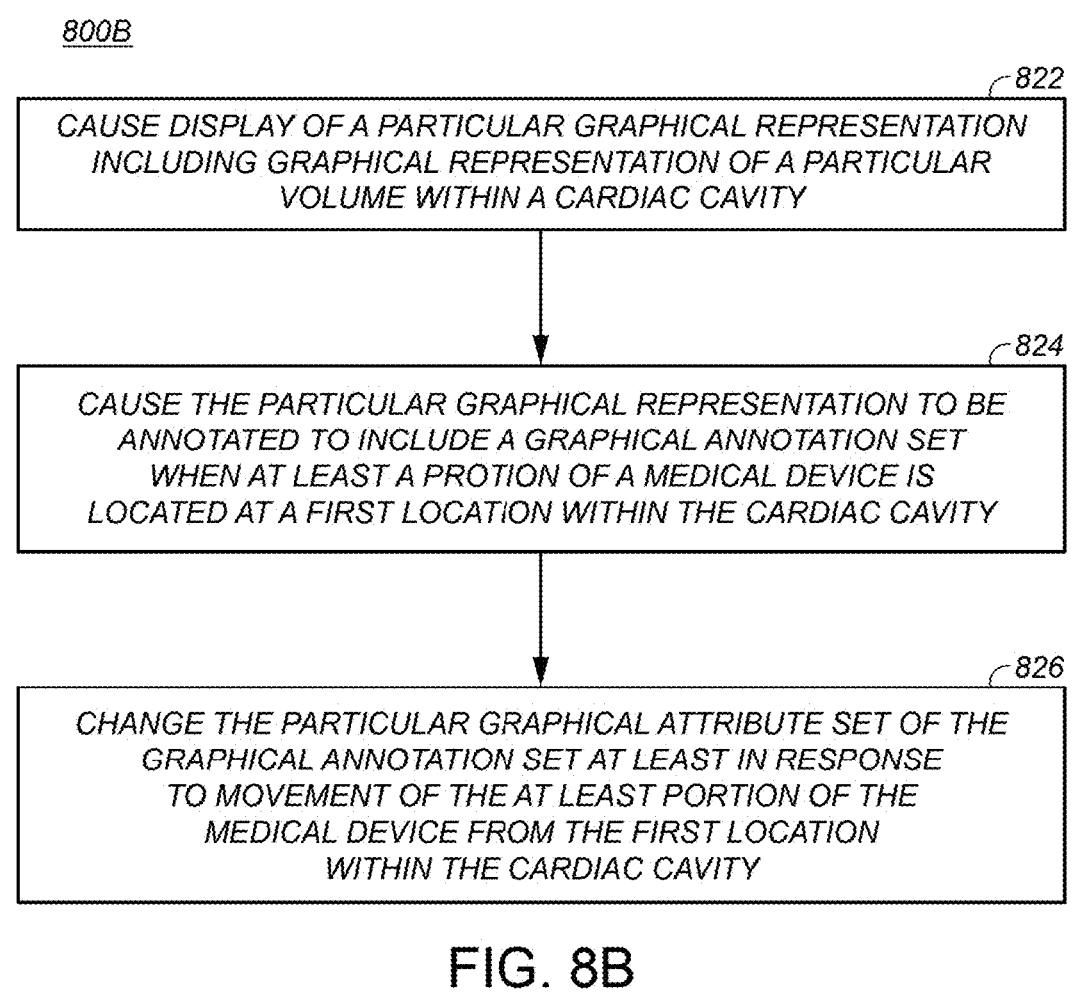

CAUSE DISPLAY OF A PARTICULAR GRAPHICAL REPRESENTATION INCLUDING GRAPHICAL REPRESENTATION OF A PARTICULAR VOLUME WITHIN A CARDIAC CAVITY

824

CAUSE THE PARTICULAR GRAPHICAL REPRESENTATION TO BE ANNOTATED TO INCLUDE A GRAPHICAL ANNOTATION SET WHEN AT LEAST A PROTION OF A MEDICAL DEVICE IS LOCATED AT A FIRST LOCATION WITHIN THE CARDIAC CAVITY

826

CHANGE THE PARTICULAR GRAPHICAL ATTRIBUTE SET OF THE GRAPHICAL ANNOTATION SET AT LEAST IN RESPONSE TO MOVEMENT OF THE AT LEAST PORTION OF THE MEDICAL DEVICE FROM THE FIRST LOCATION WITHIN THE CARDIAC CAVITY

FIG. 8B

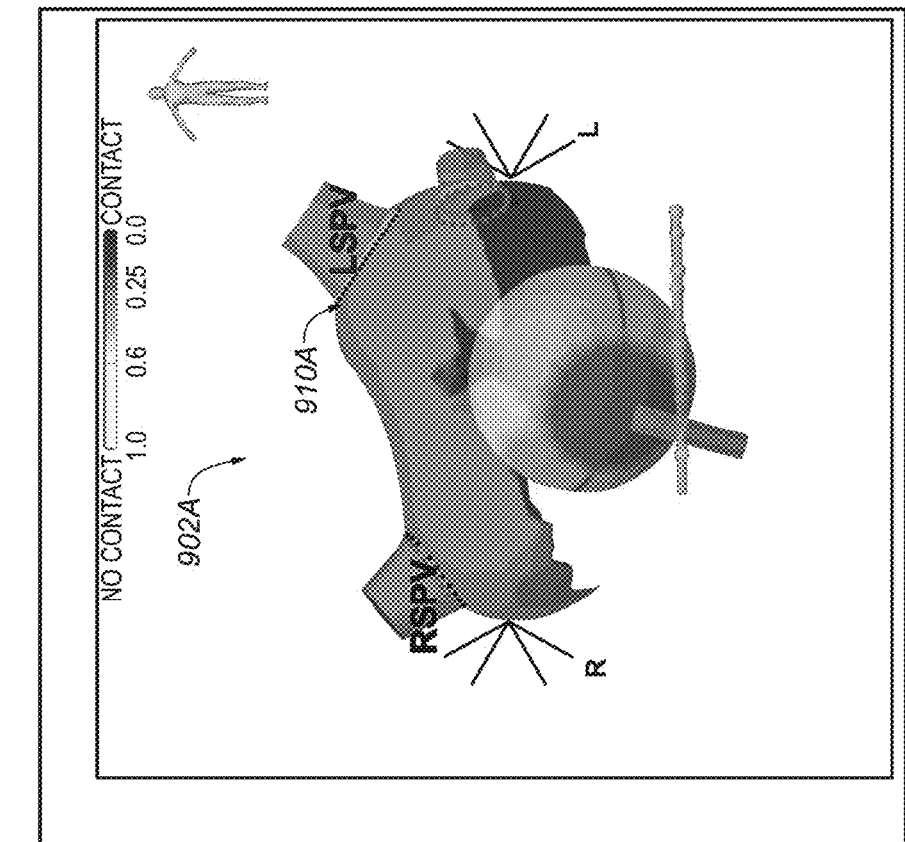
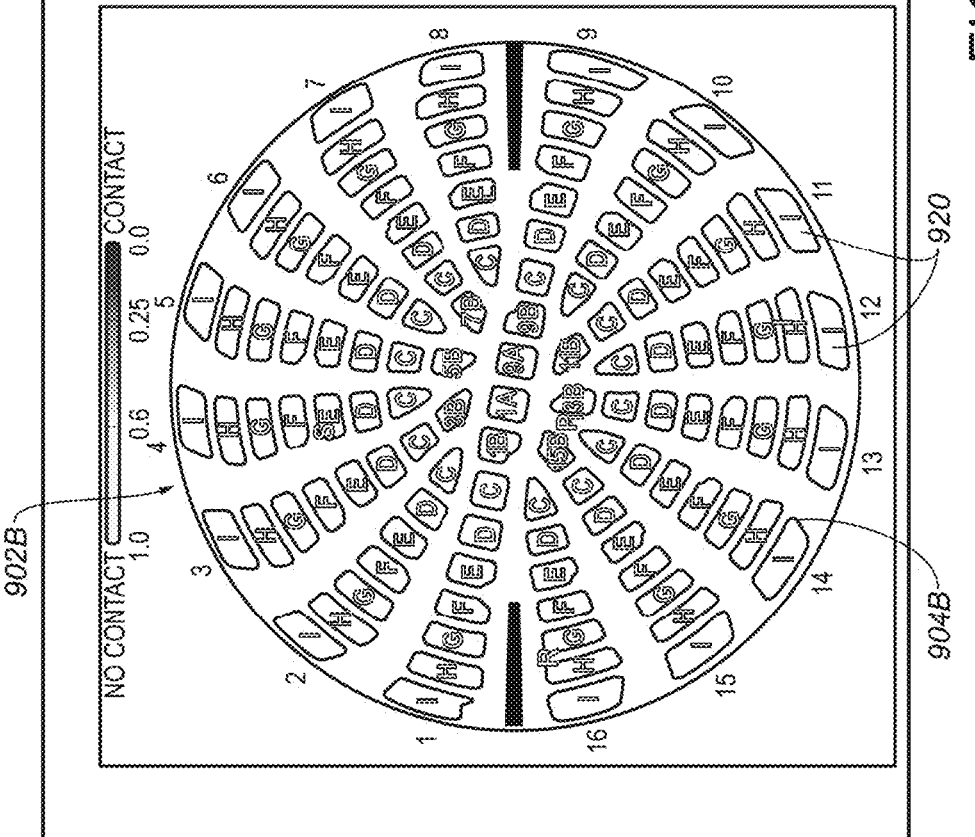
FIG. 9I

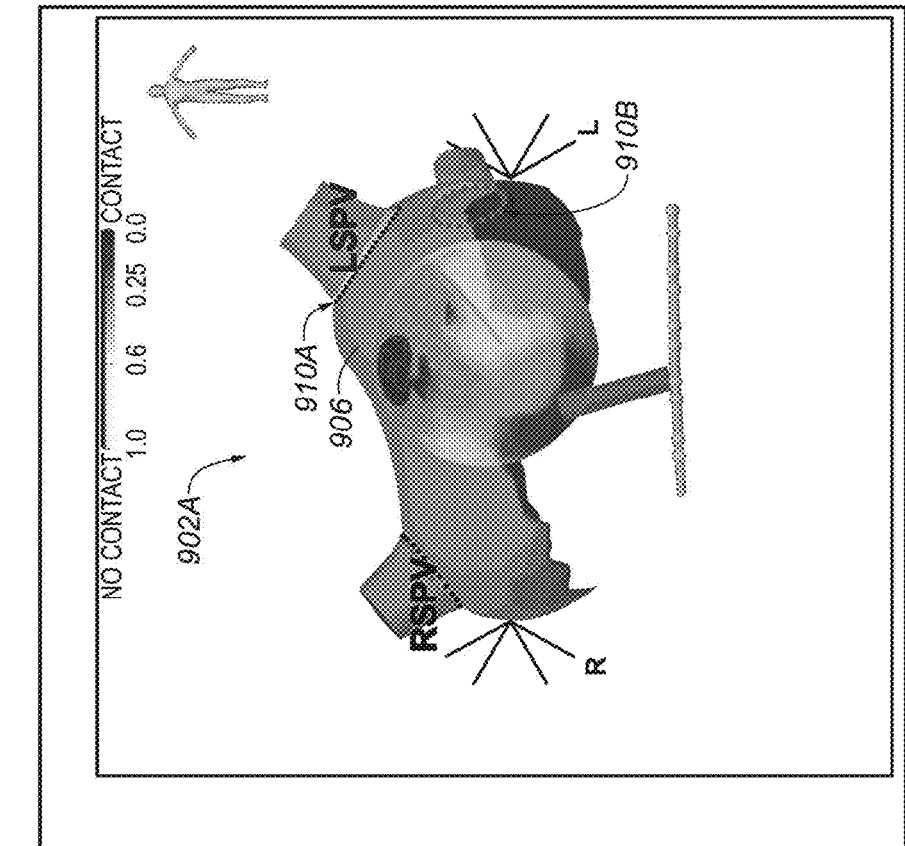
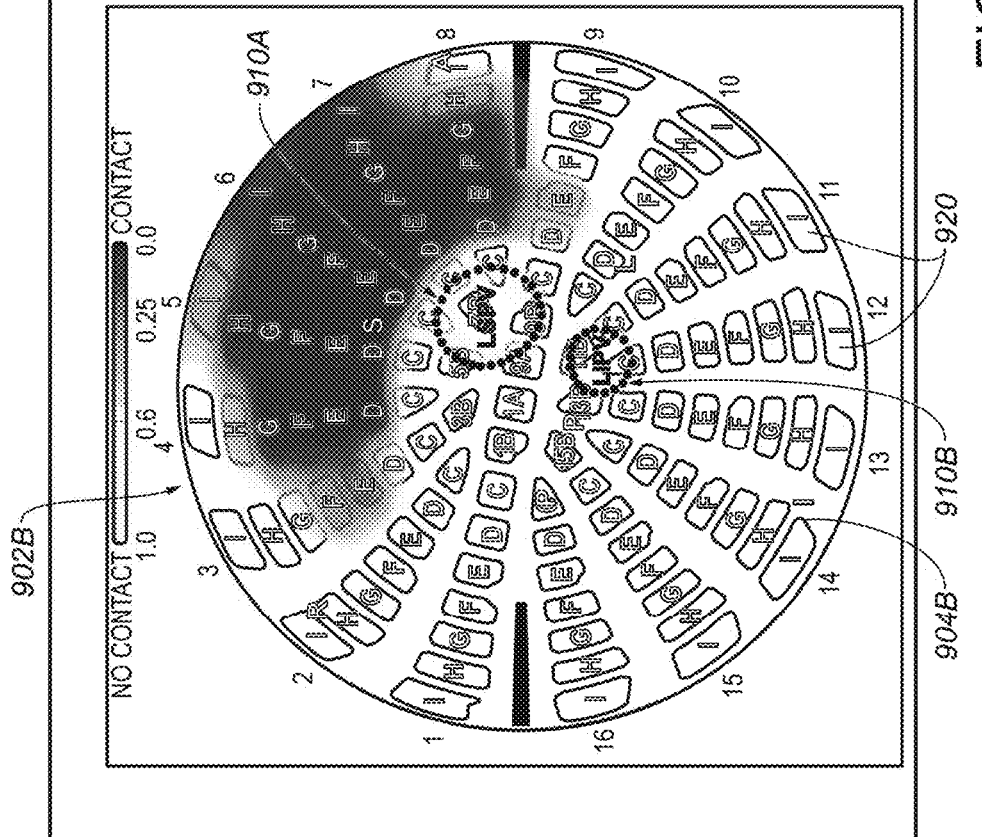
FIG. 9J

SYSTEMS AND METHODS FOR FACILITATING MOVEMENT EFFICIENCY OF A MEDICAL DEVICE WITHIN A BODILY CAVITY

CROSS-REFERENCE TO RELATED APPLICATIONS

This application claims the benefit of U.S. Provisional Application No. 63/441,296, filed Jan. 26, 2023, the entire disclosure of which is hereby incorporated herein by reference.

This application is related to concurrently-filed sibling U.S. Non-Provisional Application Ser. No. 18/543,301, which is filed having the same title and inventors.

TECHNICAL FIELD

Aspects of this disclosure generally are related to systems and methods for facilitating at least percutaneous or intravascular movement of a medical device within a bodily cavity.

BACKGROUND

Cardiac surgery was initially undertaken using highly invasive open procedures. A sternotomy, which is a type of incision in the center of the chest that separates the sternum, was typically employed to allow access to the heart. In the past several decades, more and more cardiac operations have been performed using intravascular or percutaneous techniques, where access to inner organs or other tissue is gained via a medical device or probe known as a catheter.

Intravascular or percutaneous surgeries benefit patients by reducing surgery risk, complications, and recovery time. However, the use of intravascular or percutaneous technologies also raises some particular challenges. Medical devices used in intravascular or percutaneous surgery need to be deployed via catheter systems which significantly increase the complexity of the device structure. As well, doctors do not have direct visual contact with the medical devices once the devices are positioned within the body.

One example of where intravascular or percutaneous medical techniques have been employed is in the treatment of a heart disorder called atrial fibrillation. Atrial fibrillation is a disorder in which spurious electrical signals cause an irregular heartbeat. Atrial fibrillation has been treated with open heart methods using a technique known as the "Cox-Maze procedure". During this procedure, physicians create specific patterns of lesions in the left or right atria to block various paths taken by the spurious electrical signals. Such lesions were originally created using incisions, but are now typically created by ablating the tissue with various techniques including radio-frequency (RF) energy, microwave energy, laser energy and cryogenic techniques. The procedure is performed with a high success rate despite the lack of direct vision that is provided in open procedures, but is relatively complex to perform intravascularly or percutaneously because of the difficulty in correctly positioning various catheter devices to create the lesions in the correct locations. Various problems, potentially leading to severe adverse results, may occur if the lesions are placed incorrectly. For example, if tissue ablation is attempted by a transducer in a state in which the transducer is not in sufficient contact with tissue, some ablation procedures may generate thermal coagulum (i.e., a clot) in blood, which may lead to stroke or other harm to the patient. It also is particularly important to know the position of the various transducers which will be creating the lesions relative to cardiac features such as the pulmonary veins and mitral valve of a cardiac chamber. The continuity, transmurality, and placement of the lesion patterns that are formed can impact the ability to block paths taken within the heart by spurious electrical signals. The ability to achieve desired lesions is often dependent on correctly manipulating a catheter device to provide sufficient contact between various ones of the transducers and the tissue and knowing the location of the transducers relative to various anatomical features of the bodily cavity in which the transducers are manipulated. Variability associated with various anatomical structures often requires additional physical manipulation of a catheter device to improve the contact or positioning of the catheter device with respect to anatomical features.

Some conventional systems have attempted to address the problem of lack of visibility of an internal medical device associated with percutaneous or intravascular procedures. Some conventional systems rely on fluoroscopic imaging to view the location of an internal medical device, but the present inventors recognized that such fluoroscopic imaging does not readily produce images of tissue within the bodily cavity in sufficient detail to assess the location or particular degree of tissue contact associated with a particular transducer or to identify sufficient proximity to particular anatomical landmarks within the bodily cavity. Some conventional systems generate a graphical model of a tissue surface defining a bodily cavity into which a medical device or probe is deployed based on data acquired from electric potential-based navigation systems, electromagnetic-based navigation systems, or ultrasound-based navigation systems. Some of these conventional navigation systems rely on a three-dimensional (3D) location of the medical device or probe located in the particular bodily cavity that is to be modeled. Some of these conventional navigation systems may incorporate a user interface employed to show a 3D graphical model of the bodily cavity. Some 3D graphical models typically are relatively coarse in nature and may not provide detailed information regarding the positioning of various anatomical landmarks or features (e.g., ports associated with the pulmonary veins of a cardiac chamber or cavity). Knowing where various anatomical landmarks or features are in the bodily cavity and the correlated 3D graphical model may improve the ability of the medical practitioner to navigate the medical device or probe relative to particular anatomical landmarks or features. Unfortunately, identifying or ascertaining a relative positioning between graphical depictions of the medical device or probe and various anatomical landmarks or features in the 3D graphical model of the bodily cavity is cumbersome, subject to visualization errors, and time consuming. The present inventors recognized that these conventional systems for generating the anatomical models do not, among other things, allow the user, with sufficient efficiency and effectiveness, to quickly assess a particular positioning of a medical device or probe with respect to a particular location within a bodily cavity.

For at least these and other reasons, the present inventors recognized that a need in the art exists for improved systems and methods to facilitate navigation of a medical device or probe within a bodily cavity by indicating relative positioning between the medical device or probe and a particular location within a bodily cavity with improved efficiency and effectiveness.

SUMMARY

At least the above-discussed need is addressed and technical solutions are achieved by various embodiments of the present invention. According to some embodiments, a medical system may be summarized as including a data processing device system, an input-output device system communicatively connected to the data processing device system, and a memory device system communicatively connected to the data processing device system and storing a program executable by the data processing device system. According to various embodiments, the data processing device system may be configured by the program at least to cause, via the input-output device system, display of a particular graphical representation including a graphical representation of a particular volume within a cardiac cavity of a patient. According to various embodiments, the data processing device system may be configured by the program at least to cause, via the input-output device system, the particular graphical representation to be annotated to include a graphical annotation set having a particular graphical attribute set at least in a state in which at least a portion of a medical device is located at a first location within the cardiac cavity. According to various embodiments, the data processing device system may be configured by the program at least to cause, at least in response to a movement of the at least the portion of the medical device within the cardiac cavity from the first location within the cardiac cavity, a changing of the particular graphical attribute set of the graphical annotation set while the graphical annotation set, which is annotated to the particular graphical representation, graphically remains in correspondence with a same location within the patient.

In some embodiments, the data processing device system may be configured by the program at least to cause, via the input-output device system, the graphical representation of the particular volume within the cardiac cavity to include a graphical depiction of at least a part of a tissue surface in the cardiac cavity at least in the state in which the at least the portion of the medical device is located at the first location within the cardiac cavity.

In some embodiments, the data processing device system may be configured by the program at least to cause, via the input-output device system, the graphical representation of the particular volume within the cardiac cavity to include a graphical depiction of information indicating various degrees of contact between at least a part of the medical device and a tissue surface in the cardiac cavity at least in the state in which the at least the portion of the medical device is located at the first location within the cardiac cavity. In some embodiments, the data processing device system may be configured by the program at least to cause, via the input-output device system, the graphical representation of the particular volume within the cardiac cavity to include a graphical depiction of information indicating no contact between the at least the part of the medical device and the tissue surface in the cardiac cavity at least in a state in which the at least the portion of the medical device is located at a second location within the cardiac cavity, the second location other than the first location. In some embodiments, in a state in which the movement of the at least the portion of the medical device within the cardiac cavity from the first location within the cardiac cavity is a movement of the at least the portion of the medical device within the cardiac cavity from the first location to the second location within the cardiac cavity, the data processing device system may be configured by the program at least to cause, via the input-output device system and in response to at least the movement of the at least the portion of the medical device within the cardiac cavity from the first location to the second location within the cardiac cavity, the graphical annotation set to have a different visual appearance at least in the state in which the at least the portion of the medical device is located at the second location within the cardiac cavity than when the at least the portion of the medical device is located at the first location within the cardiac cavity.

In some embodiments, the data processing device system may be configured by the program at least to cause, via the input-output device system, the graphical representation of the particular volume within the cardiac cavity to include a graphical depiction of an anatomical feature of the cardiac cavity at least in the state in which the at least the portion of the medical device is located at the first location within the cardiac cavity. In some embodiments, at least a portion of the graphical annotation set included in the particular graphical representation may graphically surround at least a portion of the graphical depiction of the anatomical feature at least in the state in which the at least the portion of the medical device is located at the first location within the cardiac cavity.

In some embodiments, the graphical annotation set may identify an anatomical feature of the cardiac cavity. In some embodiments, the data processing device system may be configured by the program at least to receive, via the input-output device system, user input defining at least part of the graphical annotation set, and cause, via the input-output device system, the particular graphical representation to be annotated to include the graphical annotation set, at least in response to the received user input.

In some embodiments, the data processing device system may be configured by the program at least to cause, via the input-output device system, the particular graphical representation to be annotated to include the graphical annotation set having the particular graphical attribute set at least in the state in which the at least the portion of the medical device is located at the first location within the cardiac cavity at least by causing, via the input-output device system, the graphical representation of the particular volume within the cardiac cavity to be annotated to include the graphical annotation set. In some embodiments, the data processing device system may be configured by the program at least to cause, via the input-output device system, relative graphical movement between the graphical annotation set and the graphical representation of the particular volume within the cardiac cavity at least in response to movement of the at least the portion of the medical device within the cardiac cavity from the first location within the cardiac cavity.

In some embodiments, the data processing device system may be configured by the program at least to cause, via the input-output device system, a graphical repositioning of the graphical annotation set from a first location in the particular graphical representation to a second location in the particular graphical representation at least in response to movement of the at least the portion of the medical device within the cardiac cavity away from the first location within the cardiac cavity, each of the first location in the particular graphical representation and the second location in the particular graphical representation corresponding to the same location within the patient. In some embodiments, each of the first location in the particular graphical representation and the second location in the particular graphical representation is a location in the graphical representation of the particular volume within the cardiac cavity. In some embodiments, the graphical representation of the particular volume within the cardiac cavity includes a map including a two-dimensional graphical representation of at least part of the particular volume within the cardiac cavity, and the data processing device system may be configured by the program at least to cause, via the input-output device system, the particular graphical representation to be annotated to include the graphical annotation set having the particular graphical attribute set at least in the state in which the at least the portion of the medical device is located at the first location within the cardiac cavity at least by causing, via the input-output device system, the two-dimensional graphical representation of the at least part of the particular volume within the cardiac cavity to be annotated to include the graphical annotation set.

In some embodiments, the data processing device system may be configured by the program at least to cause, via the input-output device system, the graphical representation of the particular volume within the cardiac cavity to remain graphically stationary in the particular graphical representation at least in a state in which the movement of the at least the portion of the medical device within the cardiac cavity from the first location within the cardiac cavity occurs. In some embodiments, the data processing device system may be configured by the program at least to cause, via the input-output device system, the graphical annotation set to remain graphically stationary in the particular graphical representation at least in a state in which the movement of the at least the portion of the medical device within the cardiac cavity from the first location within the cardiac cavity occurs. In some embodiments, the graphical representation of the particular volume within the cardiac cavity may be a three-dimensional graphical representation of the particular volume within the cardiac cavity.

In some embodiments, at least in the state in which the at least the portion of the medical device is located at the first location within the cardiac cavity, the particular graphical attribute set of the graphical annotation set, may visually indicate a first distance between the at least the portion of the medical device and a particular location in the cardiac cavity. In some embodiments, in a state in which the movement of the at least the portion of the medical device within the cardiac cavity from the first location within the cardiac cavity is a movement of the at least the portion of the medical device within the cardiac cavity from the first location to a second location within the cardiac cavity, the data processing device system may be configured by the program at least to cause, via the input-output device system and in response to at least the movement of the at least the portion of the medical device within the cardiac cavity from the first location to the second location within the cardiac cavity, the particular graphical attribute set of the graphical annotation set to be changed in a manner that the particular graphical attribute set of the graphical annotation set is changed, at least in a state in which the at least the portion of the medical device is located at the second location within the cardiac cavity, to visually indicate a second distance between the at least the portion of the medical device and the particular location within the cardiac cavity, the second location other than the first location, and the second distance different than the first distance.

In some embodiments, the data processing device system may be configured by the program at least to cause the changing of the particular graphical attribute set of the graphical annotation set at least in response to the movement of the at least the portion of the medical device within the cardiac cavity from the first location in the cardiac cavity at least by changing a size, a color, or a degree of transparency of at least a first graphical annotation in the graphical annotation set. In some embodiments, the changing of the particular graphical attribute set of the graphical annotation set at least in response to the movement of the at least the portion of the medical device within the cardiac cavity from the first location in the cardiac cavity may cause, via the input-output device system, at least a graphical removal of at least a first graphical annotation in the graphical annotation set.

In some embodiments, the graphical representation of the particular volume within the cardiac cavity may include a map including a two-dimensional graphical representation of at least part of the particular volume within the cardiac cavity. In some embodiments, the graphical representation of the particular volume within the cardiac cavity may include a map that maps three dimensional spatial coordinates of at least part of the particular volume within the cardiac cavity onto a two-dimensional coordinate frame. In some embodiments, the particular graphical representation may include a map that maps three-dimensional spatial coordinates of various sub-portions of the at least the portion of the medical device onto a two-dimensional coordinate frame. In some embodiments, the graphical representation of the particular volume within the cardiac cavity may include a three-dimensional graphical representation of the particular volume within the cardiac cavity mapped onto a two-dimensional coordinate frame.

In some embodiments the particular volume within the cardiac cavity may correspond to at least part of a volume occupied by the at least the portion of the medical device.

In some embodiments, at least in the state in which the particular graphical representation is caused to be annotated to include the graphical annotation set having the particular graphical attribute set, the graphical annotation set having the particular graphical attribute set corresponds to a second location within the patient, and the changing of the particular graphical attribute set of the graphical annotation set may occur while the graphical annotation set, which is annotated to the particular graphical representation, graphically remains in correspondence with the second location within the patient. In some embodiments, at least in the state in which the at least the portion of the medical device is located at the first location within the cardiac cavity, the graphical annotation set having the particular graphical attribute set corresponds to a second location within the patient, and the changing of the particular graphical attribute set of the graphical annotation set may occur while the graphical annotation set, which is annotated to the particular graphical representation, graphically remains in correspondence with the second location within the patient.

In some embodiments, the input-output device system may include a catheter-device-location tracking system, and the first location within the cardiac cavity is indicated by a location signal set provided by the catheter-device-location tracking system. In some embodiments, the input-output device system may include a catheter-device-location tracking system. In some embodiments, at least in a state in which the particular graphical representation is caused to be annotated to include the graphical annotation set having the particular graphical attribute set, the graphical annotation set having the particular graphical attribute set corresponds to a second location indicated by a location signal set provided by the catheter-device-location tracking system, and the changing of the particular graphical attribute set of the graphical annotation set may occur while the graphical annotation set, which is annotated to the particular graphical representation, graphically remains in correspondence with the second location. In some embodiments, the second location within the patient may be a location within the cardiac cavity. In some embodiments, the second location within the patient may be a location on a tissue surface in the cardiac cavity. In some embodiments, the second location within the patient may be a location of a pulmonary vein of the cardiac cavity. In some embodiments, the first location within the cardiac cavity may be a location where the at least the portion of the medical device contacts a tissue surface in the cardiac cavity.

In some embodiments, the input-output device system includes a catheter-device-location tracking system, and wherein the data processing device system may be configured by the program at least to receive location signal sets from the catheter-device-location tracking system, and generate the graphical representation of the particular volume within the cardiac cavity of the patient based at least on the received location signal sets.

Various systems may include combinations and subsets of all those summarized above.

According to some embodiments, a medical system may be summarized as including a data processing device system, an input-output device system communicatively connected to the data processing device system, and a memory device system communicatively connected to the data processing device system and storing a program executable by the data processing device system. In some embodiments, the data processing device system may be configured by the program at least to cause, via the input-output device system, display of a three-dimensional graphical representation of a first volume within a bodily cavity. In some embodiments, the data processing device system may be configured by the program at least to cause, via the input-output device system, the three-dimensional graphical representation of the first volume within the bodily cavity to be annotated to include a graphical annotation set at least in a state in which at least a portion of a medical device is located within the bodily cavity. In some embodiments, the data processing device system may be configured by the program at least to cause, via the input-output device system, at least in response to the causing the three-dimensional graphical representation of the first volume within the bodily cavity to be annotated to include the graphical annotation set, and at least in the state in which the at least the portion of the medical device is located within the bodily cavity, the three-dimensional graphical representation of the first volume within the bodily cavity to add an anatomical feature graphical representation extending away from a first particular region of the three-dimensional graphical representation of the first volume within the bodily cavity, the added anatomical feature graphical representation extending away from the first particular region of the three-dimensional graphical representation of the first volume within the bodily cavity.

In some embodiments, the added anatomical feature graphical representation may extend away from the first particular region of the three-dimensional graphical representation of the first volume within the bodily cavity in a direction extending outwardly from the three-dimensional graphical representation of the first volume within the bodily cavity.

In some embodiments, the anatomical feature graphical representation extending away from the first particular region of the three-dimensional graphical representation of the first volume within the bodily cavity may be added to the three-dimensional graphical representation of the first volume within the bodily cavity at least in a state in which the at least the portion of the medical device is located at a particular location within the bodily cavity. In some embodiments, the data processing device system may be configured by the program at least to cause, via the input-output device system, display of a three-dimensional graphical representation of a volume corresponding to a volume of the portion of the medical device graphically depicted as located at least in part within the three-dimensional graphical representation of the first volume within the bodily cavity. According to some embodiments, a first relative graphical positioning between the three-dimensional graphical representation of the volume corresponding to the volume of the portion of the medical device and the three-dimensional graphical representation of the first volume within the bodily cavity may correspond to a second relative positioning between the at least the portion of the medical device and the bodily cavity at least in the state in which the at least the portion of the medical device is located at the particular location within the bodily cavity. In some embodiments, the added anatomical feature graphical representation may extend away from the first particular region of the three-dimensional graphical representation of the first volume within the bodily cavity in a direction away from the three-dimensional graphical representation of the volume corresponding to the volume of the portion of the medical device in a state in which the first relative graphical positioning exists between the three-dimensional graphical representation of the volume corresponding to the volume of the portion of the medical device and the three-dimensional graphical representation of the first volume within the bodily cavity. In some embodiments, the three-dimensional graphical representation of the first volume within the bodily cavity may be annotated to include the graphical annotation set in the state in which the first relative graphical positioning exists between the three-dimensional graphical representation of the volume corresponding to the volume of the portion of the medical device and the three-dimensional graphical representation of the first volume within the bodily cavity.

In some embodiments, the data processing device system may be configured by the program at least to cause, via the input-output device system, display of a three-dimensional graphical representation of a volume corresponding to a volume of the portion of the medical device graphically depicted as located at least in part within the three-dimensional graphical representation of the first volume within the bodily cavity, and in some embodiments, the data processing device system may be configured by the program at least to cause, via the input-output device system and in response to a change in a relative positioning between the at least the portion of the medical device within the bodily cavity, varying of a relative graphical positioning between the three-dimensional graphical representation of the volume corresponding to the volume of the portion of the medical device and the three-dimensional graphical representation of the first volume within the bodily cavity.

In some embodiments, the added anatomical feature graphical representation may include a graphically represented conical frustum shaped portion. In some embodiments, the added anatomical feature graphical representation may include a graphical representation of a shape, the shape including an outer side surface between a first end region of the shape and a second end region of the shape opposing the first end region of the shape, and the outer side surface of the shape being curved along a geodesic of the outer side surface spanning from the first end region to the second end region. In some embodiments, the added anatomical feature graphical representation may include a graphically represented pseudosphere shaped portion. In some embodiments, the added anatomical feature graphical representation may include a graphically represented cylindrical portion. In some embodiments, the bodily cavity is a cardiac cavity, and the added anatomical feature graphical representation may correspond to a pulmonary vein.

In some embodiments, the data processing device system may be configured by the program at least to cause, via the input-output device system, display of a two-dimensional graphical representation of at least part of a second volume within the bodily cavity. In some embodiments, the data processing device system may be configured by the program at least to cause, via the input-output device system, the two-dimensional graphical representation of the at least part of the second volume within the bodily cavity to be annotated to include the graphical annotation set at least in a state in which the at least the portion of the medical device is located at a first location within the bodily cavity, the graphical annotation set included in the two-dimensional graphical representation of the at least part of the second volume within the bodily cavity displayed in a two-dimensional graphical manner. In some embodiments, the data processing device system may be configured by the program at least to cause, via the input-output device system, the three-dimensional graphical representation of the first volume within the bodily cavity to be annotated to include the graphical annotation set at least in response to the data processing device system causing, via the input-output device system, the two-dimensional graphical representation of the at least part of the second volume within the bodily cavity to be annotated to include the graphical annotation set, the graphical annotation set included in the three-dimensional graphical representation of the first volume within the bodily cavity displayed in a three-dimensional graphical manner. In some embodiments, the three-dimensional graphical representation of the first volume within the bodily cavity may be annotated to include the graphical annotation set in a state in which the at least the portion of the medical device is located at the first location within the bodily cavity. In some embodiments, the anatomical feature graphical representation may be added to the three-dimensional graphical representation of the first volume within the bodily cavity in a state in which the at least the portion of the medical device is located at the first location within the bodily cavity. In some embodiments, the second volume within the bodily cavity may form some, but not all, of the first volume within the bodily cavity. In some embodiments, the second volume within the bodily cavity may correspond to at least part of a volume occupied by the at least the portion of the medical device. In some embodiments, the two-dimensional graphical representation of the at least part of the second volume within the bodily cavity may map three-dimensional surface portions of the at least the portion of the medical device onto a two-dimensional coordinate frame. In some embodiments, the two-dimensional graphical representation of the at least part of the second volume within the bodily cavity may map three-dimensional tissue surface portions corresponding to the at least part of the second volume within the bodily cavity onto a two-dimensional coordinate frame. In some embodiments, the at least the portion of the medical device includes a plurality of transducers, and the two-dimensional graphical representation of the at least part of the second volume within the bodily cavity may map information indicating a three-dimensional spatial distribution of transducer-to-tissue contact information onto a two-dimensional coordinate frame. In some embodiments, the at least the portion of the medical device includes a plurality of transducers, and the two-dimensional graphical representation of the at least part of the second volume within the bodily cavity may map information indicating a three-dimensional spatial distribution of the plurality of transducers onto a two-dimensional coordinate frame. In some embodiments, the data processing device system may be configured by the program at least to receive, via the input-output device system, user input defining at least part of the graphical annotation set, and cause, via the input-output device system, updating of the two-dimensional graphical representation of the at least part of the second volume within the bodily cavity to be annotated to include the graphical annotation set, at least in response to the received user input.

In some embodiments, at least a portion of the graphical annotation set included in the three-dimensional graphical representation of the first volume within the bodily cavity may graphically surround, in three-dimensional graphical space, the first particular region of the three-dimensional graphical representation of the first volume within the bodily cavity.

In some embodiments, the input-output device system includes a catheter-device-location tracking system, and the data processing device system may be configured by the program at least to receive location signal sets from the catheter-device-location tracking system, and generate the three-dimensional graphical representation of the first volume within the bodily cavity based at least on the received location signal sets.

Various systems may include combinations and subsets of all those summarized above.

Various embodiments of the present invention may include systems, devices, or machines that are or include combinations or subsets of any one or more of the systems, devices, or machines and associated features thereof summarized above or otherwise described herein (which should be deemed to include the figures).

Further, all or part of any one or more of the systems, devices, or machines summarized above or otherwise described herein or combinations or sub-combinations thereof may implement or execute all or part of any one or more of the processes or methods described herein or combinations or sub-combinations thereof.

For example, in some embodiments, a method is executed by a data processing device system according to a program stored by a communicatively connected memory device system, the data processing device system also communicatively connected to an input-output device system, and the method including: causing, via the input-output device system, display of a particular graphical representation including a graphical representation of a particular volume within a cardiac cavity of a patient; causing, via the input-output device system, the particular graphical representation to be annotated to include a graphical annotation set having a particular graphical attribute set at least in a state in which at least a portion of a medical device is located at a first location within the cardiac cavity; and causing, via the input-output device system and at least in response to a movement of the at least the portion of the medical device within the cardiac cavity from the first location within the cardiac cavity, a changing of the particular graphical attribute set of the graphical annotation set while the graphical annotation set, which is annotated to the particular graphical representation, graphically remains in correspondence with a same location within the patient.

For another example, in some embodiments, a method is executed by a data processing device system according to a program stored by a communicatively connected memory device system, the data processing device system also communicatively connected to an input-output device system, and the method including: causing, via the input-output device system, display of a three-dimensional graphical representation of a first volume within a bodily cavity; causing, via the input-output device system, the three-dimensional graphical representation of the first volume within the bodily cavity to be annotated to include a graphical annotation set at least in a state in which at least a portion of a medical device is located within the bodily cavity; and causing, via the input-output device system, at least in response to the causing the three-dimensional graphical representation of the first volume within the bodily cavity to be annotated to include the graphical annotation set, and at least in the state in which the at least the portion of the medical device is located within the bodily cavity, the three-dimensional graphical representation of the first volume within the bodily cavity to add an anatomical feature graphical representation extending away from a first particular region of the three-dimensional graphical representation of the first volume within the bodily cavity, the added anatomical feature graphical representation extending away from the first particular region of the three-dimensional graphical representation of the first volume within the bodily cavity.

It should be noted that various embodiments of the present invention include variations of the methods or processes summarized above or otherwise described herein (which should be deemed to include the figures) and, accordingly, are not limited to the actions described or shown in the figures or their ordering, and not all actions shown or described are required according to various embodiments. According to various embodiments, such methods may include more or fewer actions and different orderings of actions. Any of the features of all or part of any one or more of the methods or processes summarized above or otherwise described herein may be combined with any of the other features of all or part of any one or more of the methods or processes summarized above or otherwise described herein.

In addition, a computer program product may be provided that includes program code portions for performing some or all of any one or more of the methods or processes and associated features thereof described herein, when the computer program product is executed by a computer or other computing device or device system. Such a computer program product may be stored on one or more computer-readable storage mediums, also referred to as one or more computer-readable data storage mediums or a computer-readable storage medium system.

For example, in some embodiments, one or more computer-readable storage mediums store a program executable by a data processing device system communicatively connected to an input-output device system, the program including display instructions configured to cause, via the input-output device system, display of a particular graphical representation including a graphical representation of a particular volume within a cardiac cavity of a patient; annotation instructions configured to cause, via the input-output device system, the particular graphical representation to be annotated to include a graphical annotation set having a particular graphical attribute set at least in a state in which at least a portion of a medical device is located at a first location within the cardiac cavity; and graphical attribute set changing instructions configured to cause, via the input-output device system and at least in response to a movement of the at least the portion of the medical device within the cardiac cavity from the first location within the cardiac cavity, a changing of the particular graphical attribute set of the graphical annotation set while the graphical annotation set, which is annotated to the particular graphical representation, graphically remains in correspondence with a same location within the patient.

For another example, in some embodiments, one or more computer-readable storage mediums store a program executable by a data processing device system communicatively connected to an input-output device system, the program including: display instructions configured to cause, via the input-output device system, display of a three-dimensional graphical representation of a first volume within a bodily cavity; annotation instructions configured to cause, via the input-output device system, the three-dimensional graphical representation of the first volume within the bodily cavity to be annotated to include a graphical annotation set at least in a state in which at least a portion of a medical device is located within the bodily cavity; and graphical representation instructions configured to cause, via the input-output device system, at least in response to the causing the three-dimensional graphical representation of the first volume within the bodily cavity to be annotated to include the graphical annotation set, and at least in the state in which the at least the portion of the medical device is located within the bodily cavity, the three-dimensional graphical representation of the first volume within the bodily cavity to add an anatomical feature graphical representation extending away from a first particular region of the three-dimensional graphical representation of the first volume within the bodily cavity, the added anatomical feature graphical representation extending away from the first particular region of the three-dimensional graphical representation of the first volume within the bodily cavity.

In some embodiments, each of any of one or more or all of the computer-readable data storage mediums or medium systems (also referred to as processor-accessible memory device systems) described herein is a non-transitory computer-readable (or processor-accessible) data storage medium or medium system (or memory device system) including or consisting of one or more non-transitory computer-readable (or processor-accessible) storage mediums (or memory devices) storing the respective program(s) which may configure a data processing device system to execute some or all of any of one or more of the methods or processes described herein.

Further, any of all or part of one or more of the methods or processes and associated features thereof discussed herein may be implemented or executed on or by all or part of a device system, apparatus, or machine, such as all or a part of any of one or more of the systems, apparatuses, or machines described herein or a combination or sub-combination thereof.

BRIEF DESCRIPTION OF THE DRAWINGS

It is to be understood that the attached drawings are for purposes of illustrating aspects of various embodiments and may include elements that are not to scale.

FIGS. 8A and 8B illustrate program configurations or methods of facilitating movement efficiency of a medical device within a bodily cavity of a patient, according to various example embodiments.

FIGS. 9A-9K illustrate a sequence of states of a particular graphical representation that is annotated or otherwise modified to facilitate movement efficiency of a medical device within a bodily cavity of a patient, according to various example embodiments.

DETAILED DESCRIPTION

Figure 1:
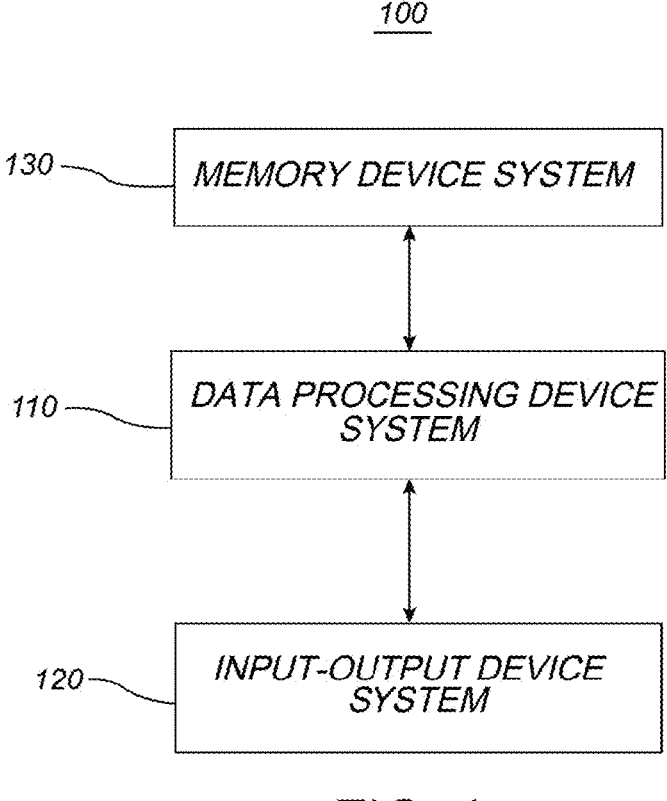
FIG. 1 includes a schematic representation of a medical system according to various example embodiments, the medical system including a data processing device system, an input-output device system, and a memory device system.

At least some embodiments of the present invention include systems and methods that facilitate improved navigation of a medical device within a bodily cavity, such as with improved efficiency and effectiveness of indicating a desired location within a bodily cavity. For instance, in some embodiments, improved systems and methods provide enhanced capabilities for graphically representing one or more anatomical features in a bodily cavity, or graphically representing the location(s) of one or more anatomical features in the bodily cavity, or both enhanced capabilities for graphically representing one or more anatomical features in a bodily cavity and graphically representing the location(s) of one or more anatomical features in the bodily cavity. At least some embodiments of the present invention include systems and methods providing enhanced capabilities for locating at least a portion of a medical device in a bodily cavity, e.g., with respect to an anatomical feature. In some embodiments, the disclosed systems form part of various anatomical mapping systems. In some embodiments, the disclosed systems form part of various tissue ablation systems including thermal ablation systems (e.g., RF ablation systems) and pulsed field ablation ("PFA") systems. In some embodiments, the disclosed systems generate a graphical model of a tissue surface defining a bodily cavity into which at least a portion of a medical device or probe is deployed. (It should be noted that further uses of the phrase "medical device" should be interpreted to include "probe".) In some embodiments, the graphical model representing the bodily cavity is derived based on data acquired from electric-potential-based navigation systems, electromagnetic-based navigation systems, or ultrasound-based navigation systems. Some of these navigation systems rely on a three-dimensional ("3D") location of the medical device located in the particular bodily cavity that is to be modeled. Some of these navigation systems may incorporate a user interface employed to show a 3D graphical model of the bodily cavity, which, in some of these systems, is generated via a medical practitioner moving a part of the medical device (which moves a corresponding transducer set) along the tissue wall. Some of these systems may compile a set of mapped locations from such movement and, from such mapped locations, build the 3D graphical model of the bodily cavity.

As described in greater detail below, in various embodiments of the present invention, one or more graphical models is or are annotated with a graphical annotation set that graphically remains in correspondence with a same location within the patient. In some embodiments, the graphical annotation set may highlight, enhance the visibility of, or otherwise call a user's attention to a location of a portion of the medical device, a location (which may be a location of an anatomical feature or other location) inside or outside of the bodily cavity, or a relative positioning between a portion of the medical device and the location inside or outside of the bodily cavity. At least in instances in which the location within the patient is outside the bodily cavity, the graphical annotation set may reside in three-dimensional graphical space at a location outside the three-dimensional graphical space occupied by a model of the bodily cavity. Such a circumstance may occur, for instance, when the bodily cavity itself has expanded (e.g., due to a portion of a cardiac cycle in the case of a heart, or due to expansion caused by the medical device pressing against the wall of the bodily cavity) beyond a size predicted or represented by the model of the bodily cavity. According to various embodiments, a particular graphical attribute set of the graphical annotation set is varied with movement of at least part of the medical device within the bodily of cavity. According to various embodiments, variances in the particular graphical attribute set of the graphical annotation set may be employed to provide enhanced positional information of a portion of the medical device within the bodily cavity, enhanced positional information of a location in the bodily cavity, or enhanced positional information of a relative positioning between a portion of the medical device and a location in the bodily cavity (e.g., a location of an anatomical feature of the bodily cavity). For instance, in some embodiments, such variances in the particular graphical attribute set may facilitate medical device navigation at least by helping a user understand what impact movement of a portion of the medical device has had with respect to a location to which the graphical annotation set corresponds. For example, in some embodiments, such variances in the particular graphical attribute set may indicate whether such movement of the portion of a medical device has caused an increase or a decrease in distance from, or a change in direction toward, a particular location within the bodily cavity.

It is noted however, that various embodiments may have other benefits or goals than those described above or otherwise herein.

In this regard, in the descriptions herein, certain specific details are set forth in order to provide a thorough understanding of various embodiments of the invention. However, one skilled in the art will understand that the invention may be practiced at a more general level without one or more of these details. In other instances, well known structures have not been shown or described in detail to avoid unnecessarily obscuring descriptions of various embodiments of the invention.

Any reference throughout this specification to "one embodiment", "an embodiment", "an example embodiment", "an illustrated embodiment", "a particular embodiment", and the like means that a particular feature, structure or characteristic described in connection with the embodiment is included in at least one embodiment. Thus, any appearance of the phrase "in one embodiment", "in an embodiment", "in an example embodiment", "in this illustrated embodiment", "in this particular embodiment", or the like in this specification is not necessarily always referring to one embodiment or a same embodiment. Furthermore, the particular features, structures or characteristics of different embodiments may be combined in any suitable manner to form one or more other embodiments. In one embodiment, all references to "some embodiments" may refer to the same single embodiment.

Unless otherwise explicitly noted or required by context, the word "or" is used in this disclosure in a non-exclusive sense. In addition, unless otherwise explicitly noted or required by context, the word "set" is intended to mean one or more. For example, the phrase, "a set of objects" means one or more of the objects. In some embodiments, the word "subset" is intended to mean a set having the same or fewer elements of those present in the subset's parent or superset. In other embodiments, the word "subset" is intended to mean a set having fewer elements of those present in the subset's parent or superset. In this regard, when the word "subset" is used, some embodiments of the present invention utilize the meaning that "subset" has the same or fewer elements of those present in the subset's parent or superset, and other embodiments of the present invention utilize the meaning that "subset" has fewer elements of those present in the subset's parent or superset.

Further, the phrase "at least" is or may be used herein at times merely to emphasize the possibility that other elements may exist besides those explicitly listed. However, unless otherwise explicitly noted (such as by the use of the term "only") or required by context, non-usage herein of the phrase "at least" nonetheless includes the possibility that other elements may exist besides those explicitly listed. For example, the phrase, 'based at least on A' includes A as well as the possibility of one or more other additional elements besides A. In the same manner, the phrase, 'based on A' includes A, as well as the possibility of one or more other additional elements besides A. However, the phrase, 'based only on A' includes only A. Similarly, the phrase 'configured at least to A' includes a configuration to perform A, as well as the possibility of one or more other additional actions besides A. In the same manner, the phrase 'configured to A' includes a configuration to perform A, as well as the possibility of one or more other additional actions besides A. However, the phrase, 'configured only to A' means a configuration to perform only A.

The word "device", the word "machine", the word "system", and the phrase "device system" all are intended to include one or more physical devices or sub-devices (e.g., pieces of equipment) that interact to perform one or more functions, regardless of whether such devices or sub-devices are located within a same housing or different housings. However, it may be explicitly specified according to various embodiments that a device or machine or device system resides entirely within a same housing to exclude embodiments where the respective device, machine, system, or device system resides across different housings. The word "device" may equivalently be referred to as a "device system" in some embodiments, and the word "system" may equivalently be referred to as a "device system" in some embodiments.

Further, the phrase "in response to" may be used in this disclosure. For example, this phrase may be used in the following context, where an event A occurs in response to the occurrence of an event B. In this regard, such phrase includes, for example, that at least the occurrence of the event B causes or triggers or is a necessary precondition for the event A, according to various embodiments.

The phrase "thermal ablation" as used in this disclosure refers, in some embodiments, to an ablation method in which destruction of tissue occurs by hyperthermia (elevated tissue temperatures) or hypothermia (depressed tissue temperatures). Thermal ablation may include radiofrequency ("RF") ablation, microwave ablation, or cryo-ablation by way of non-limiting examples. Thermal ablation energy waveforms can take various forms. For example, in some thermal ablation embodiments, energy (e.g., RF energy) is provided in the form of a continuous waveform. In some thermal ablation embodiments, energy (e.g., RF energy) is provided in the form of discrete energy applications (e.g., in the form of a duty-cycled waveform).

The phrase "pulsed field ablation" ("PFA") as used in this disclosure refers, in some embodiments, to an ablation method that employs high voltage pulse delivery in a unipolar (also referred to as monopolar) or bipolar fashion in proximity to target tissue. In some embodiments, each high voltage pulse may be referred to as a discrete energy application. In some embodiments, a grouped plurality of high voltages pulses may be referred to as a discrete energy application. Each high voltage pulse may be a monophasic pulse including a single polarity, or a biphasic pulse including a first component having a first particular polarity and a second component having a second particular polarity opposite the first particular polarity. In some embodiments, the second component of the biphasic pulse follows immediately after the first component of the biphasic pulse. In some embodiments, the first and second components of the biphasic pulse are temporally separated by a relatively small time interval. The electric field applied by the high voltage pulses in PFA physiologically changes the tissue cells to which the energy is applied (e.g., puncturing or perforating the cell membrane to form various pores therein). If a relatively low field strength is established, the formed pores close after the electric field is removed, and the cells maintain viability (e.g., a process sometimes referred to as reversible electroporation). If the field strength that is established is relatively high, then permanent, and sometimes larger, pores form in the tissue cells, the pores allowing leakage of cell contents, eventually resulting in cell death (e.g., a process sometimes referred to as irreversible electroporation).

The word "proximal", in the context of a proximal portion, proximal location, and the like of a medical device, includes, for example, the portion, location, and the like, being or being configured to be further away from a patient or portion of or region within a patient (e.g., a bodily cavity) intended to be treated or assessed by the medical device, as compared to a distal portion, location, and the like of the medical device, according to some embodiments. In some embodiments, the word "proximal", in the context of a proximal portion, proximal location, and the like of a medical device, includes, for example, the portion, location, and the like, being or being configured to be delivered (e.g., percutaneously or intravascularly) toward a patient or portion of or region within a patient (e.g., a bodily cavity) intended to be treated or assessed by the medical device, after or behind a distal portion, location, and the like of the medical device. On the other hand, the word "distal", in the context of a distal portion, distal location, and the like of a medical device, includes, for example, the portion, location, and the like, being or being configured to be closer to a patient or portion of or region within a patient (e.g., a bodily cavity) intended to be treated or assessed by the medical device, as compared to a proximal portion, location, and the like of the medical device, according to some embodiments. In some embodiments, the word "distal", in the context of a distal portion, distal location, and the like of a medical device, includes, for example, the portion, location, and the like, being or being configured to be delivered (e.g., percutaneously or intravascularly) toward a patient or portion of or region within a patient (e.g., a bodily cavity) intended to be treated or assessed by the medical device, before or ahead of a proximal portion, location, and the like of the medical device. The word "fluid" as used in this disclosure should be understood to include any fluid that can be contained within a bodily cavity or can flow into or out of, or both into and out of a bodily cavity via one or more bodily openings positioned in fluid communication with the bodily cavity. In the case of cardiac applications, fluid such as blood will flow into and out of various intracardiac cavities (e.g., a left atrium or a right atrium).

The phrase "bodily opening" as used in this disclosure should be understood to include, for example, a naturally occurring bodily opening or channel or lumen; a bodily opening or channel or lumen or perforation in tissue formed by an instrument or tool using techniques that can include, but are not limited to, mechanical, thermal, electrical, chemical, and exposure or illumination techniques; a bodily opening or channel or lumen or perforation formed by trauma to a body; or various combinations of one or more of the above. Various elements having respective openings, lumens, or channels and positioned within the bodily opening (e.g., a catheter sheath) may be present in various embodiments. These elements may provide a passageway through a bodily opening for various devices employed in various embodiments.

The phrase "bodily cavity" as used in this disclosure should be understood to mean a cavity in a body and the tissue surface in the bodily cavity that at least partially envelopes, at least partially surrounds, or forms a boundary of a volume of space within the bodily cavity. The bodily cavity may be a cavity or chamber provided in a bodily organ (e.g., an intracardiac cavity or chamber of a heart).

The word "tissue" as used in this disclosure should be understood to include, for example, any surface-forming tissue that is used to form a surface of a body or a surface within a bodily cavity, a surface of an anatomical feature or a surface of a feature associated with a bodily opening positioned in fluid communication with the bodily cavity. The tissue may include, for example, part or all of a tissue wall or membrane that defines a surface of the bodily cavity. In this regard, the tissue may form an interior surface of the bodily cavity that surrounds a fluid within the bodily cavity. In the case of cardiac applications, tissue may include, for example, tissue used to form an interior surface of an intracardiac cavity such as a left atrium or a right atrium. In some embodiments, the word "tissue" may refer to a tissue having fluidic properties (e.g., blood) and may be referred to as fluidic tissue.

The word "transducer" as used in this disclosure should be interpreted broadly as any device configured to transmit or deliver energy; distinguish between fluid and tissue; sense temperature; generate heat; ablate tissue; sense, sample or measure electrical activity of a tissue surface (e.g., sense, sample, or measure intracardiac electrograms, or sense, sample, or measure intracardiac voltage data); stimulate tissue; provide location information (e.g., in conjunction with a navigation system); or any combination thereof. A transducer may convert input energy of one form into output energy of another form. Without limitation, a transducer may include, for example, an electrode that functions as, or as part of, a sensing device included in the transducer, an energy delivery device included in the transducer, or both a sensing device and an energy delivery device included in the transducer. A transducer may be constructed from several parts, which may be discrete components or may be integrally formed. In this regard, although transducers, electrodes, or both transducers and electrodes are referenced with respect to various embodiments, it is understood that other transducers or transducer elements may be employed in other embodiments. It is understood that a reference to a particular transducer in various embodiments may also imply a reference to an electrode, as an electrode may be part of the transducer as shown, e.g., at least with respect to FIG. 7 discussed below.

The word "activation" as used in this disclosure should be interpreted broadly as making active a particular function as related to various transducers disclosed in this disclosure. Particular functions may include, but are not limited to, those described above or otherwise herein with respect to transducers. For example, in some embodiments, activation of a tissue ablation function of a particular transducer is initiated by causing energy sufficient for tissue ablation from an energy source device system to be delivered to the particular transducer. Also, in this example, the activation can last for a duration of time concluding when the ablation function is no longer active, such as when energy sufficient for the tissue ablation is no longer provided to the particular transducer. In some contexts, however, the word "activation" may merely refer to the initiation of the activating of a particular function, as opposed to referring to both the initiation of the activating of the particular function and the subsequent duration in which the particular function is active. In these contexts, the phrase or a phrase similar to "activation initiation" may be used.

In some embodiments, the word "adjacent", the word "proximate", and the like refer at least to a sufficient closeness between the objects or events defined as adjacent, proximate, or the like, to allow the objects or events to interact in a designated way. For example, in the case of physical objects, if object A performs an action on an adjacent or proximate object B, objects A and B would have at least a sufficient closeness to allow object A to perform the action on object B. In this regard, some actions may require contact between the associated objects, such that if object A performs such an action on an adjacent or proximate object B, objects A and B would be in contact, for example, in some instances or embodiments where object A needs to be in contact with object B to successfully perform the action. In some embodiments, the word "adjacent", the word "proximate", and the like additionally or alternatively refer to objects or events that do not have another substantially similar object or event between them. For example, object or event A and object or event B could be considered adjacent or proximate (e.g., physically or temporally) if they are immediately next to each other (with no other object or event between them) or are not immediately next to each other but no other object or event that is substantially similar to object or event A, object or event B, or both objects or events A and B, depending on the embodiment, is between them. In some embodiments, the word "adjacent", the word "proximate", and the like additionally or alternatively refer to at least a sufficient closeness between the objects or events defined as adjacent, proximate, and the like, the sufficient closeness being within a range that does not place any one or more of the objects or events into a different or dissimilar region or time period, or does not change an intended function of any one or more of the objects or events or of an encompassing object or event that includes a set of the objects or events. Different embodiments of the present invention adopt different ones or combinations of the above definitions. Of course, however, the word "adjacent", the word "proximate", and the like are not limited to any of the above example definitions, according to some embodiments. In addition, the word "adjacent" and the word "proximate" do not have the same definition, according to some embodiments.

Some embodiments of the present invention may be implemented at least in part by a data processing device system or a controller system configured by a software program. Such a program may equivalently be implemented as multiple programs, and some, or all, of such software program(s) may be equivalently constructed in hardware. In this regard, reference to "a program" should be interpreted to include one or more programs.

The word "program" in this disclosure should be interpreted to include one or more programs including a set of instructions or modules that can be executed by one or more components in a system, such as a controller system or a data processing device system, in order to cause or configure the system to perform one or more operations. The set of instructions or modules may be stored by any kind of memory device, such as those described subsequently with respect to the memory device system 130 or 330 shown in at least FIGS. 1, 5 and 6. In addition, this disclosure may describe or similarly describe that the instructions or modules of a program are configured to cause the performance of an action. The phrase "configured to" in this context is intended to include, for example, at least (a) instructions or modules that are presently in a form executable by one or more data processing devices to cause performance of the action (e.g., in the case where the instructions or modules are in a compiled and unencrypted form ready for execution), and (b) instructions or modules that are presently in a form not executable by the one or more data processing devices, but could be translated into the form executable by the one or more data processing devices to cause performance of the action (e.g., in the case where the instructions or modules are encrypted in a non-executable manner, but through performance of a decryption process, would be translated into a form ready for execution). In some instances, this disclosure may describe that the instructions or modules of a program perform an action. Such descriptions should be deemed to be equivalent to describing that the instructions or modules are configured to cause the performance of the action. The word "module" can be defined as a set of instructions. The word "program" and the word "module" may each be interpreted to include multiple sub-programs or multiple sub-modules, respectively. In this regard, reference to a program or a module may be considered to refer to multiple programs or multiple modules.

Further, it is understood that information or data may be operated upon, manipulated, or converted into different forms as it moves through various devices or workflows. In this regard, unless otherwise explicitly noted or required by context, it is intended that any reference herein to information or data or the like includes modifications to that information or data. For example, "data X" may be encrypted for transmission, and a reference to "data X" is intended to include both its encrypted and unencrypted forms, unless otherwise required or indicated by context. For another example, "image information Y" may undergo a noise filtering process, and a reference to "image information Y" is intended to include both the pre-processed form and the noise-filtered form, unless otherwise required or indicated by context. In other words, both the pre-processed form and the noise-filtered form are considered to be "image information Y", unless otherwise required or indicated by context. In order to stress this point, the phrase "or a derivative thereof" or the like may be used herein. Continuing the preceding example, the phrase "image information Y or a derivative thereof" refers to both the pre-processed form and the noise-filtered form of "image information Y", unless otherwise required or indicated by context, with the noise-filtered form potentially being considered a derivative of "image information Y". However, non-usage of the phrase "or a derivative thereof" or the like nonetheless includes derivatives or modifications of information or data unless otherwise explicitly noted or required by context.

Further, in some embodiments, the phrase "graphical representation" used herein is intended to include a visual representation presented via a display device system and may include computer-generated text, graphics, animations, or one or more combinations thereof, which may include one or more visual representations originally generated, at least in part, by an image-capture device, such as computerized tomography ("CT") scans or images, magnetic resonance imaging ("MRI") scans or images, or images created from a navigation system (e.g., electro-potential navigation system or an electro-magnetic navigation system), according to some embodiments. The graphical representation may include various entities depicted in a three-dimensional manner, in some embodiments. The graphical representation may include various entities depicted in a two-dimensional manner that are mapped from a three-dimensional space into a two-dimensional coordinate system, in some embodiments. Example methods are described herein with respect to FIGS. 8A and 8B. Such figures include blocks associated with actions, computer-executable instructions of one or more programs, or both actions and computer-executable instructions, according to various embodiments. It should be noted that the respective instructions associated with any such blocks therein need not be separate instructions and may be combined with other instructions to form a combined instruction set. The same set of instructions may be associated with more than one block. In this regard, the block arrangement shown in each of the method figures herein is not limited to an actual structure of any program or set of instructions or required ordering of method tasks, and such method figures, according to some embodiments, merely illustrate the tasks that instructions are configured to perform, for example, upon execution by a data processing device system in conjunction with interactions with one or more other devices or device systems.

FIG. 1 schematically illustrates at least a portion of a medical system 100, which may be at least part of or include a user interface system or controller system that may be employed to at least select, control, activate, or monitor functions or states of a medical device, according to some embodiments. The system 100 includes a data processing device system 110, an input-output device system 120, and a processor-accessible memory device system 130. The processor-accessible memory device system 130 and the input-output device system 120 are communicatively connected to the data processing device system 110. According to some embodiments, various components such as data processing device system 110, input-output device system 120, and processor-accessible memory device system 130 form at least part of a controller system (e.g., controller 324 shown in FIGS. 2, 3, 5, and 6).

The data processing device system 110 includes one or more data processing devices that implement or execute, in conjunction with other devices, such as those in the system 100, various methods and actions described herein, including those described with respect to methods exemplified in FIGS. 8A and 8B. Each of the phrases "data processing device", "data processor", "processor", "controller", "computing device", "computer" and the like is intended to include any data or information processing device, such as a central processing unit (CPU), a control circuit, a desktop computer, a laptop computer, a mainframe computer, a tablet computer, a personal digital assistant, a cellular or smart phone, and any other device configured to process information or data, manage information or data, or handle information or data, whether implemented with electrical, magnetic, optical, quantum, or biological components, or otherwise. The data processing device system 110 may be a distributed data processing device system including multiple communicatively connected data processing devices. On the other hand, the data processing device system 110 need not be a distributed data processing device system and, consequently, may include one or more data processing devices located within a single housing.

The memory device system 130 includes one or more processor-accessible memory devices configured to store one or more programs and information, including the program(s) and information needed to execute the methods or actions described herein, including those described with respect to example method FIGS. 8A and 8B. In this regard, each of the blocks illustrated in the example methods of FIGS. 8A and 8B may represent or be associated with program instructions stored in the memory device system 130 and configured to cause execution of the respective action(s). The memory device system 130 may be a distributed processor-accessible memory device system including multiple processor-accessible memory devices communicatively connected to the data processing device system 110 via a plurality of computers and/or devices. However, the memory device system 130 need not be a distributed processor-accessible memory system and, consequently, may include one or more processor-accessible memory devices located within a single data processing device or housing.

Each of the phrases "processor-accessible memory" and "processor-accessible memory device" and the like is intended to include any processor-accessible data storage device or medium, whether volatile or nonvolatile, electronic, magnetic, optical, or otherwise, including but not limited to, registers, hard disk drives, Compact Discs, DVDs, SSDs, flash memories, ROMs, and RAMs. In some embodiments, each of the phrases "processor-accessible memory" and "processor-accessible memory device" is intended to include or be a processor-accessible (or computer-readable) storage medium or data storage medium. In some embodiments, each of the phrases "processor-accessible memory" and "processor-accessible memory device" is intended to include or be a non-transitory processor-accessible (or computer-readable) storage medium or data storage medium. In some embodiments, the processor-accessible memory device system 130 may be considered to include or be a non-transitory processor-accessible (or computer-readable) storage medium system or data storage medium system. And, in some embodiments, the processor-accessible memory device system 130 may be considered to include or be a non-transitory processor-accessible (or computer-readable) storage medium system or data storage medium system including or consisting of one or more non-transitory processor-accessible (or computer-readable) storage mediums or data storage mediums.

The phrase "communicatively connected" is intended to include any type of connection, whether wired or wireless, between devices, data processors, or programs between which data may be communicated. Further, the phrase "communicatively connected" is intended to include a connection between devices or programs within a single data processor or computer, a connection between devices or programs located in different data processors or computers, and a connection between devices not located in data processors or computers at all. In this regard, although the memory device system 130 is shown separately from the data processing device system 110 and the input-output device system 120, one skilled in the art will appreciate that the memory device system 130 may be located completely or partially within the data processing device system 110 or the input-output device system 120. Further in this regard, although the input-output device system 120 is shown separately from the data processing device system 110 and the memory device system 130, one skilled in the art will appreciate that such system may be located completely or partially within the data processing device system 110 or the memory device system 130, for example, depending upon the contents of the input-output device system 120. Further still, the data processing device system 110, the input-output device system 120, and the memory device system 130 may be located entirely within the same device or housing or may be separately located, but communicatively connected, among different devices or housings. In the case where the data processing device system 110, the input-output device system 120, and the memory device system 130 are located within the same device, the system 100 of FIG. 1 may be implemented by a single application-specific integrated circuit (ASIC), field programmable gate array (FPGA), system on chip (SOC), or other type of integrated circuit, in some embodiments.

The input-output device system 120 may include a mouse, a keyboard, a touch screen, another computer, a processor-accessible memory device system, or any device or combination of devices from which a desired selection, desired information, instructions, or any other data is input to the data processing device system 110. The input-output device system 120 may include a user-activatable control system that is responsive to a user action. The user-activatable control system may include at least one user input element that may be activated or deactivated on the basis of a particular user action. The input-output device system 120 may include any suitable interface for receiving information, instructions, or any data from other devices and systems described in various ones of the embodiments. In this regard, the input-output device system 120 may include various ones of other systems described in various embodiments. For example, the input-output device system 120 may include at least a portion of a transducer-based device system or catheter-based device system (for example, a medical device, at least a portion thereof configured to be inserted in a bodily cavity of a patient). The phrase "transducer-based device system" is intended to include one or more physical systems that include various transducers. The phrase "transducer-based device" is intended to include one or more physical devices that include various transducers. An electro-anatomical mapping device system that includes one or more transducers or a tissue ablation device system that includes one or more transducers may be considered a transducer-based device or device system, according to some embodiments.

The input-output device system 120 also may include an image generating device system, a display device system, a speaker or audio output device system, a computer, a processor-accessible memory device system, a network-interface card or network-interface circuitry, or any device or combination of devices to which information, instructions, or any other data is output by the data processing device system 110. In this regard, the input-output device system 120 may include various other devices or systems described in various embodiments. The input-output device system 120 may include any suitable interface for outputting information, instructions, or data to other devices and systems described in various ones of the embodiments. If the input-output device system 120 includes a processor-accessible memory device, such memory device may, or may not, form part, or all, of the memory device system 130. The input-output device system 120 may include any suitable interface for outputting information, instructions, or data to other devices and systems described in various ones of the embodiments. In this regard, the input-output device system 120 may include various other devices or systems described in various embodiments. In some embodiments, the input-output device system 120 may include one or more display devices that display one or more of the graphical interfaces of FIGS. 9A-9L, described below.

According to some embodiments of the present invention, the system 100 includes some or all of the systems shown in FIGS. 2-7, or vice versa. In this regard, some or all of the systems shown in FIGS. 2-7 may be a particular implementation of the system 100, according to some embodiments.

Various embodiments of medical devices (e.g., transducer-based devices) are described in this disclosure. Some of the described devices are percutaneously or intravascularly deployed. Some of the described devices are moveable between a delivery or unexpanded configuration (e.g., FIG. 5 discussed below) in which a portion of the device is sized for passage through a bodily opening leading to a bodily cavity, and an expanded or deployed configuration (e.g., FIG. 6 discussed below) in which the portion of the device has a size too large for passage through the bodily opening leading to the bodily cavity. An example of an expanded or deployed configuration, in some embodiments, is when the portion of the transducer-based device is in its intended-deployed-operational state, which may be inside the bodily cavity when, e.g., performing a therapeutic or diagnostic procedure for a patient, or which may be outside the bodily cavity when, e.g., performing testing, quality control, or other evaluation of the device. Another example of the expanded or deployed configuration, in some embodiments, is when the portion of the device is being changed from the delivery configuration to the intended-deployed-operational state to a point where the portion of the device now has a size too large for passage through the bodily opening leading to the bodily cavity.

In some example embodiments, the medical device includes transducers that sense characteristics (e.g., convective cooling, permittivity, force) that distinguish between fluid, such as fluidic tissue (e.g., blood), and tissue forming an interior surface of the bodily cavity. Such sensed characteristics can allow a medical system to map the bodily cavity, for example, using positions of openings or ports into and out of the bodily cavity to determine a position or orientation (e.g., pose), or both of the portion of the medical device in the bodily cavity. In some example embodiments, the described systems employ a navigation system or electro-anatomical mapping system (e.g., as described below with respect to at least FIG. 2 or 3, according to some embodiments) including electromagnetic-based systems and electropotential-based systems to determine a positioning of a portion of a medical device in a bodily cavity. In some example embodiments, the described medical devices are part of a tissue ablation system configured to ablate tissue in a desired pattern within the bodily cavity using various techniques (e.g., via thermal ablation, PFA, etc., according to various embodiments).

In some example embodiments, the devices are capable of sensing various cardiac functions (e.g., electrophysiological activity including intracardiac voltages). In some example embodiments, the devices are capable of providing stimulation (e.g., electrical stimulation) to tissue within the bodily cavity. Electrical stimulation may include pacing.

Figure 2:
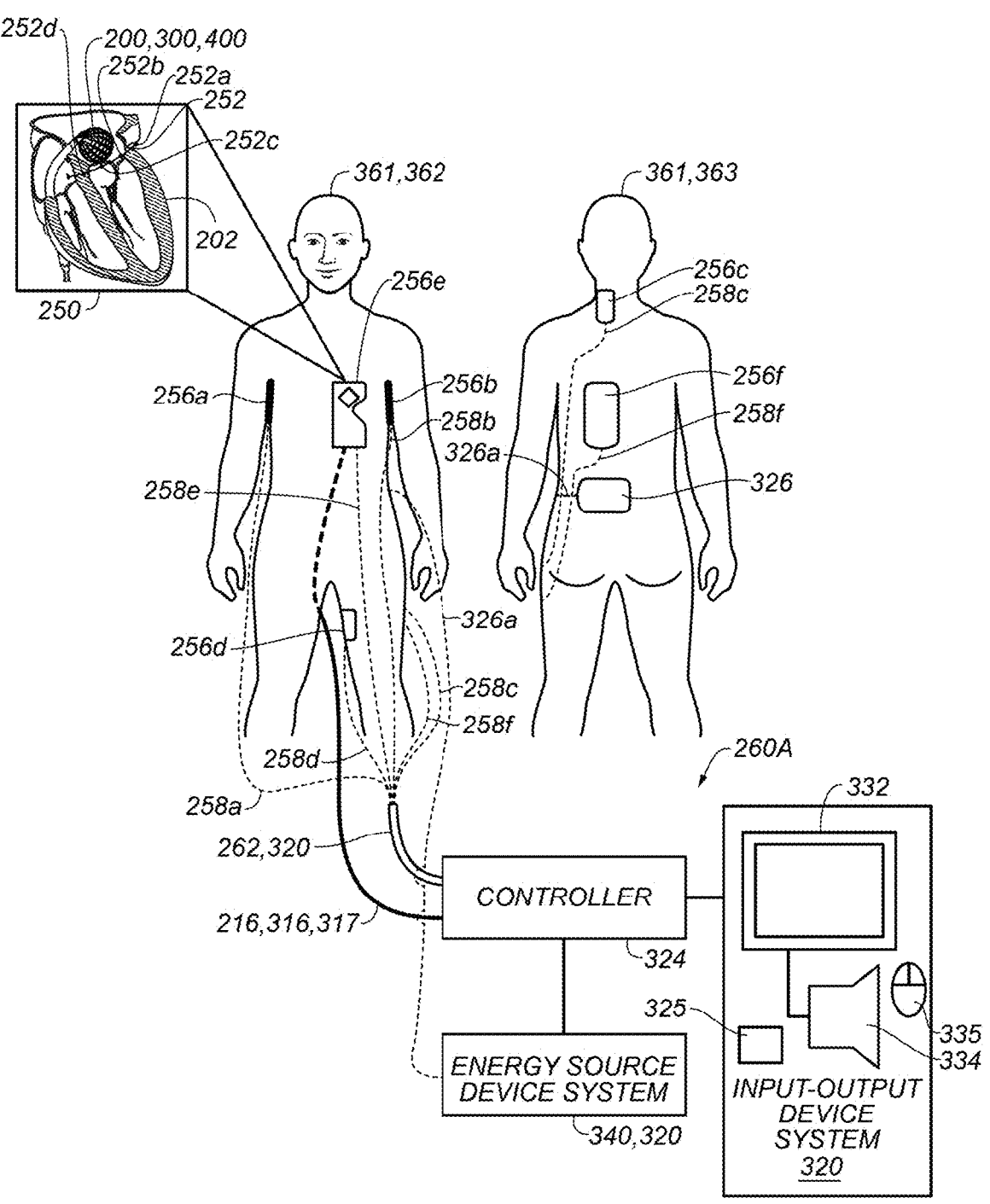
FIG. 2 includes a partially schematic representation of some particular implementations of a catheter navigation system implementing an electric-field-based location system, according to various example embodiments.

FIG. 2 includes a partially schematic representation of some particular implementations of a catheter navigation system 260A implementing an electric-field-based location system, according to various example embodiments. According to some embodiments, the catheter navigation system 260A is at least part of various medical device systems described in this disclosure. In this regard, all or part of the catheter navigation system 260A may form all or part of a medical system, such as medical system 100 shown in FIG. 1, according to some embodiments. FIG. 2 illustrates a controller 324, which may be a particular implementation of the data processing device system 110 shown in FIG. 1. Illustrated in FIG. 2 is an input-output device system 320 communicatively connected to the controller 324 and may include a display device system 332, a mouse 335 or other pointing device system, a speaker device system 334 or other audio output device system, or a sensing device system 325, according to various embodiments. Possible contents of the input-output device system 320 are discussed in more detail below. The input-output device system 320 may be a particular implementation of the input-output device system 120 shown in FIG. 1. FIG. 2 also illustrates, in cut-out illustration window 250, a medical device (e.g., catheter or medical device) 200, 300, or 400 (also referenced herein as "200, 300, 400"), discussed in more detail below, which may be communicatively connected to the controller 324 via electrical conductors 216, cable 316, electrical leads 317 (discussed in more detail below; see, e.g., at least FIGS. 4-6), or a combination thereof, according to various embodiments. According to various embodiments, medical device 200, 300, or 400 may form part of a tissue ablation system or sensing system. The electrical conductors 216, cable 316, or electrical leads 317 may reside, at least in part, within a catheter shaft 214 or 314 or within a catheter sheath 212 or 312 discussed in more detail below (see, e.g., at least FIGS. 4-6). The medical device 200, 300, or 400 may include one or more transducers (discussed in more detail below; see, e.g., at least FIGS. 4-7) and may be included in the input-output device system 320, according to some embodiments. In FIG. 2, a portion of the medical device 200, 300, or 400 is illustrated via cut-out illustration window 250 within a heart 202 of a patient 361, although the medical device 200, 300, or 400 may instead be operated outside of any living being, e.g., in a quality-control, training, or testing environment. The single patient 361 is illustrated in two parts in FIG. 2 merely to concurrently show the front-side 362 and the back-side 363 of the patient 361, although the various connections to the controller 324 are only fully shown via the illustrated front-side 362 of the patient 361 for purposes of clarity. The portion of the electrical conductors 216, cable 316, or electrical leads 317 that is outside the patient 361 is illustrated in thick solid line in FIG. 2, and the portion of the electrical conductors 216, cable 316, or electrical leads 317 that is inside the patient 361 is illustrated in thick broken line in FIG. 2. The other electrical conductors 258a-258f and 326a shown in FIG. 2 and described in more detail below are illustrated in thin broken lines for clarity even though they may typically reside outside the body of the patient 361 in some embodiments.

Also illustrated in FIG. 2 is an energy source device system 340 communicatively connected to the controller 324. The energy source device system 340 may be part of the input-output device system 320 and may be configured to provide energy to the transducers of the catheter or medical device 200, 300, or 400 for sensing, tissue ablation, or both, according to various embodiments and as discussed in more detail below. According to various embodiments, energy delivered to medical device 200, 300, or 400 for tissue ablation may be configured to cause thermal ablation or PFA. Electrode 326, shown on the lower back of the back-side 363 of patient 361 in FIG. 2, for example, may be communicatively connected to energy source device system 340 via conductor 326a. Electrode 326 may be placed externally on the body of the patient 361, according to some embodiments. Electrode 326 may be an indifferent electrode, which may facilitate the performance of impedance sensing or ablation, particularly monopolar or blended monopolar ablation, according to some embodiments. Indifferent electrode 326 is discussed further below.

FIG. 2 also illustrates electrodes 256a, 256b, 256c, 256d, 256e, and 256f that are placed externally on the body of the patient 361, according to some embodiments. The electrodes 256a, 256b, 256c, 256d, 256e, and 256f may be included in the input-output device system 320 and may be communicatively connected to the controller 324 via respective electrical conductors 258a, 258b, 258c, 258d, 258e, and 258f partially inside cable 262, according to some embodiments. Although respective electrical conductors 258a, 258b, 258c, 258d, 258e, and 258f are shown within a same cable 262 for clarity of illustration, one or more of such electrical conductors may be in separate cables. According to some embodiments, electrodes 256a, 256b, 256c, 256d, 256e, and 256f are configured to generate electric fields that enable the controller 324 to determine, at least in conjunction with corresponding sensing performed by transducers of the catheter or medical device 200, 300, or 400, X, Y, and Z coordinate axis location information of the catheter or medical device 200, 300, or 400 within the heart 202 of the patient 361 or in a quality-control, training, or testing environment. In particular, electrodes 256a and 256b (a first pair of electrodes) may be configured to generate a first electric field at a first frequency or frequency range, and one or more voltages resulting from that field are sensed with respect to a reference device 252 (shown more clearly in FIG. 4) by transducers of the catheter or medical device 200, 300, or 400 as, e.g., representing respective X-axis locations of the respective transducers. Similarly, electrodes 256c and 256d (a second pair of electrodes) may be configured to generate a second electric field at a second frequency or frequency range, and one or more voltages resulting from that field are sensed with respect to reference device 252 by transducers of the catheter or medical device 200, 300, or 400 as, e.g., representing respective Y-axis locations of the respective transducers. Similarly, electrodes 256e and 256f (a third pair of electrodes) may be configured to generate a third electric field at a third frequency or frequency range, and one or more voltages resulting from that field are sensed with respect to reference device 252 by transducers of the medical device 200, 300, or 400 as, e.g., representing respective Z-axis locations of the respective transducers. The first, second, and third frequencies or frequency ranges may be mutually exclusive, according to some embodiments. In some embodiments, the first, second, and third electric fields may have a same frequency or frequency range and be time-multiplexed in coordination with time-multiplexed sensing by the transducers of the catheter or medical device 200, 300, or 400, to facilitate repeated sequential sensing of respective X, Y, and Z-axis locations of the respective transducers. Electric field strength sensed by one or more transducers of the medical device 200, 300, or 400 may be evaluated by the controller 324 or its data processing device system 310 to determine location information including respective three-dimensional X, Y, and Z-axis locations of the transducers with respect to the first, second, and third electric fields and with respect to reference device 252 (shown as including reference electrodes 252a, 252b, 252c, and 252d, although fewer or more may be provided), according to some embodiments. The reference device 252 (see, e.g., cut-out illustration window 250 in FIG. 2 or see, e.g., FIG. 4 for more detail) may be located within the body of the patient 361, preferably in a location that keeps its positioning relatively stable, such as in the coronary sinus, to factor out transitory movements of the transducer(s) of the medical device 200, 300, or 400 due, e.g., to the beating of the heart. The one or more reference electrodes (e.g., reference electrodes 252a, 252b, 252c, and 252d) of the reference device 252 may be configured to also sense electric field strength of the first, second, and third electric fields, and the three-dimensional location of the medical device 200, 300, or 400 is determined by the controller 324 or its data processing device system 310 with respect to the reference device 252 based on the measurements made by the transducers of the medical device 200, 300, or 400 and the measurements made by the reference electrodes (e.g., reference electrodes 252a, 252b, 252c, and 252d) of the reference device 252, according to some embodiments.

The measurements made by the transducers of the medical device 200, 300, or 400, the measurements made by the reference electrodes of the reference device 252 (or reference device 257z (described in more detail below with respect to FIG. 3) in some embodiments), or both may, in some embodiments, provide at least part of location information indicating locations of at least a portion of a medical device 200, 300, or 400 in a bodily cavity or relative to a tissue surface or anatomical feature in a bodily cavity. In some embodiments, even if (i) the measurements made by the transducers of the medical device 200, 300, or 400, (ii) the measurements made by the reference electrodes of the reference device 252 (or reference device 257z in some embodiments), or both (i) and (ii) indicate locations of the at least the portion of the medical device 200, 300, or 400 with respect to an absolute reference frame associated with locations derived solely from the three-dimensional X, Y, and Z-axes, such location information may indicate (e.g., by derivation or by combination with tissue contact sensing information provided by electrodes of the medical device in some embodiments) locations of the at least the portion of the medical device 200, 300, or 400 relative to a tissue surface or anatomical feature in the bodily cavity, according to some embodiments. In some embodiments, measurements made by the transducers of the medical device 200, 300, or 400 derived relatively to the measurements made by the reference electrodes of the reference device 252 or reference device 257z may indicate locations of the at least the portion of the medical device 200, 300, or 400 relative to one or more locations on a tissue surface or otherwise within the patient body (e.g., the coronary sinus), or on the patient body (e.g., xyphoid process). In this regard, a reference, such as reference device 252 or reference device 257z may, according to various embodiments, help define a coordinate frame that moves with an organ that includes the bodily cavity (e.g., movement of the organ resulting from the cardiac cycle or pulmonary cycle), and measurements made in this coordinate frame may accordingly indicate locations of at least part of the medical device 200, 300, or 400 relative to various locations on a tissue surface or otherwise within or on a patient body, according to some embodiments. However, in some embodiments, the locations of the at least the portion of the medical device may be indicated by location information without necessarily being relative to a reference location. U.S. Pat. No. 5,697,377, issued on Dec. 16, 1997 to Frederik H. M. Wittkampf, provides examples of how to determine a three-dimensional location of a catheter (e.g., an electrode position).

In this regard, FIG. 2 illustrates a catheter navigation system 260A that may include, or form part of, a medical device (e.g., a catheter device system) 200, 300, or 400, the controller 324 or data processing device system 310 or 110, and a display device system (e.g., display device system 332), according to various embodiments. The medical device 200, 300, or 400 may include a plurality of transducers (discussed in more detail below). The catheter-device-location tracking system or catheter navigation system may include one or more external electrodes (e.g., electrodes 256a, 256b, 256c, 256d, 256e, and 256f) and one or more reference electrodes (e.g., reference electrodes 252a, 252b, 252c, 252d of reference device 252). At least part of the catheter navigation system 260A (or catheter navigation system 260B discussed below) may form at least part of a medical system, such as medical system 100 in FIG. 1. In some embodiments, the display device system 332, the medical device 200, 300, or 400, the catheter navigation system 260A (or catheter navigation system 260B discussed below), or a combination thereof may be included as part of an input-output device system (e.g., input-output device system 320 or input-output device system 120) of a medical system, such as medical system 100 in FIG. 1.

Figure 3:
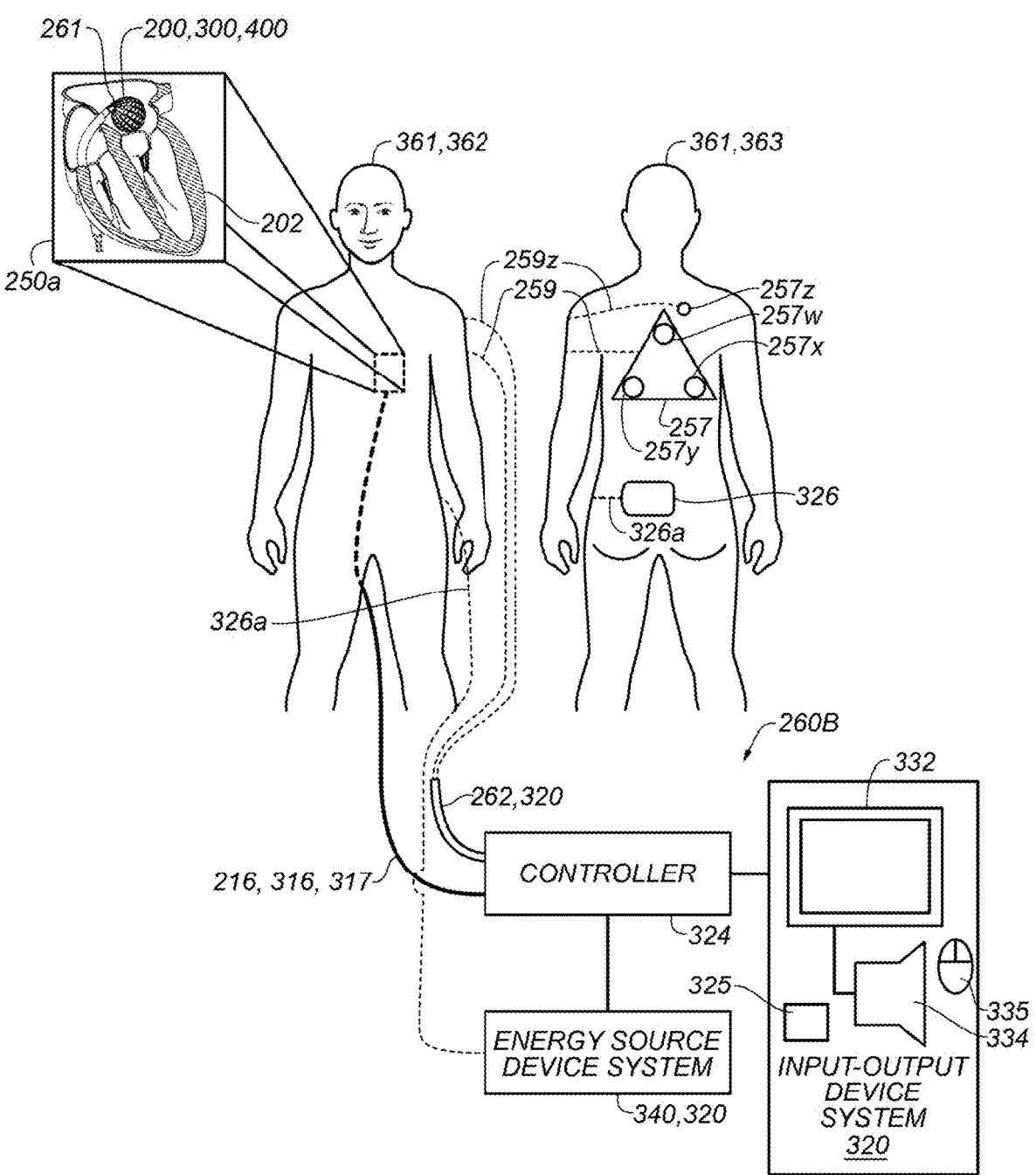
FIG. 3 includes a partially schematic representation of some particular implementations of a catheter navigation system implementing a magnetic-field-based location system, according to various example embodiments.

FIG. 3 includes a partially schematic representation of some particular implementations of the catheter navigation system 260B implementing a magnetic-field-based location system, according to various example embodiments. In this regard, FIG. 3 corresponds to FIG. 2, except that a magnetic-field-based location system is illustrated instead of an electric-field-based location system. All or part of the catheter navigation system 260B may form all or part of a medical system, such as medical system 100 shown in FIG. 1, according to some embodiments. As noted above with respect to FIG. 2, controller 324 also shown in FIG. 3 may be a particular implementation of the data processing device system 110 shown in FIG. 1.

Instead of electrodes 256a, 256b, 256c, 256d, 256e, and 256f shown in FIG. 2, FIG. 3 illustrates three magnetic field generation sources 257w, 257x, and 257y, such as coils, each of which respectively generates a magnetic field, according to some embodiments. The magnetic field generation sources 257w, 257x, and 257y may be integrally formed within a package or frame 257 located beneath the patient 361. Magnetic field generation sources 257w, 257x, and 257y may respectively be connected to the controller 324 via a set of one or more conductors 259, which may or may not be located within the same cable 262. Similarly, the reference device 257z may be connected to the controller 324 via a set of one or more conductors 259z, which may or may not be included in conductor set 259, and which may or may not be located within the same cable 262. Although shown in thin broken lines, the conductors 259, 259z typically reside outside the body of the patient 361. The medical device 200, 300, or 400 may include one or more magnetic field transducers 261 (shown on at least a portion of the medical device 200, 300, or 400 shown in the cut-out illustration window 250a in FIG. 3) configured to sense the strengths of the magnetic fields generated by magnetic field generation sources 257w, 257x, and 257y. As with some embodiments associated with FIG. 2, the magnetic field generation sources 257w, 257x, and 257y need not generate magnetic fields at different frequencies, but may instead generate the magnetic fields at the same frequency in a time-multiplexed manner such that the magnetic fields are sensed in sequence over time by the one or more magnetic field transducers 261. In some embodiments, the one or more magnetic field transducers 261 may sense the magnetic field strengths with respect to a reference device 257z, which may be akin to the reference device 252 in the electric field context of FIG. 2. With the three magnetic field strengths detected by the one or more magnetic field transducers 261 for a given time or time period, the distance(s) between the one or more transducers 261 and the magnetic field generation sources 257w, 257x, and 257y may be determined, and the three-dimensional location of the one or more transducers 261 may be determined according to triangulation as per some embodiments. With the location of the one or more transducers 261 in three-dimensional space known, and the geometry of the medical device 200, 300, or 400 (e.g., including the locations of the transducers on the medical device) relative to transducers 261 also known, the locations of the transducers of the medical device 200, 300, or 400 for the given time or time period may be determined, according to some embodiments. U.S. Patent Application Publication No. 2007/0265526 (Govari et al.), published on Nov. 15, 2007, provides examples of how to determine a three-dimensional location of a catheter in a magnetic-field-based system.

Figure 4:
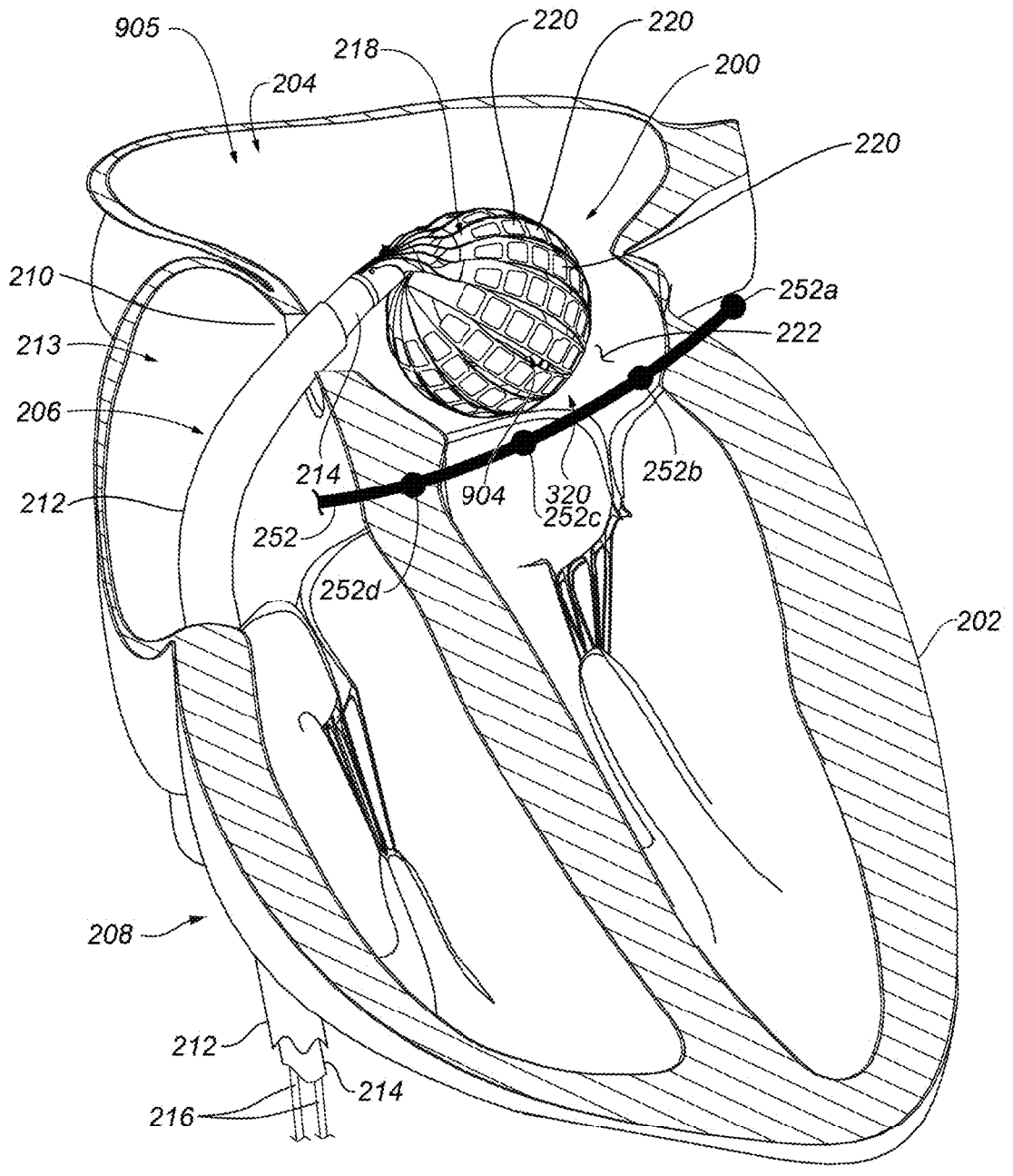
FIG. 4 includes a cutaway diagram of a heart showing a catheter navigation system including a reference device and a transducer-based device of a medical system, the reference device part of a catheter-device-location tracking system and percutaneously placed at least proximate a heart cavity, and the transducer-based device percutaneously placed in a left atrium of the heart, according to various example embodiments.

FIG. 4 is a representation of a medical device 200 useful in investigating or treating a bodily organ, for example, a heart 202, according to some embodiments. In some embodiments, the medical device 200 may form part of a tissue ablation system or sensing system. All or part of the medical device 200 may form all or part of a medical system, such as part of medical system 100 shown in FIG. 1, according to some embodiments.

Medical device 200 may be percutaneously or intravascularly inserted into a portion of the heart 202, such as an intracardiac cavity, like left atrium 204. In this example, the medical device 200 is, or is part of a catheter 206 inserted via the inferior vena cava 208 and penetrating through a bodily opening in transatrial septum 210 from right atrium 213. (In this regard, medical devices, medical systems, or medical device systems described herein that include a catheter may also be referred to as catheter devices, catheter systems, or catheter device systems, or catheter-based devices, catheter-based systems, or catheter-based device systems, according to some embodiments.) In other embodiments, other paths may be taken.

Catheter 206 includes an elongated flexible rod or shaft member 214 appropriately sized to be delivered percutaneously or intravascularly. Various portions of catheter 206 may be steerable. For example, a structure 218 supporting transducers 220 may be controlled via various manipulations to advance outwardly, to retract, to rotate clockwise, to rotate counterclockwise, and to have a particular deployment plane orientation, such as a plane in which the structure 218 progresses from a delivery configuration (e.g., described below with respect to at least FIG. 5) to or at least toward a deployed configuration (e.g., as shown in FIG. 4 and as described in more detail below with respect to at least FIG. 6), according to some embodiments. One or more other portions of the medical device 200 may be steerable. For example, a catheter sheath 212, which encompasses or surrounds at least part of an elongate shaft member 214 to which the structure 218 is physically coupled, may be steerable. In some embodiments, the catheter sheath 212 may be controlled via various manipulations to advance outwardly, retract, rotate clockwise, rotate counterclockwise, bend, release a bend, and have a particular bending plane orientation, according to some embodiments.

Catheter 206 may include one or more lumens. The lumen(s) may carry one or more communications or power paths, or both. For example, the lumens(s) may carry one or more electrical conductors 216 (two shown). Electrical conductors 216 provide electrical connections to medical device 200 and transducers 220 thereof that are accessible externally from a patient in which the medical device 200 is inserted.

Medical device 200 may include a frame or structure 218 which assumes an unexpanded configuration (e.g., described below with respect to at least FIG. 5) for delivery to left atrium 204, according to some embodiments, such frame or structure 218 supporting transducers. Structure 218 is expanded (e.g., shown in a deployed or expanded configuration in at least FIGS. 4 and 6) upon delivery to left atrium 204 to position a plurality of transducers 220 (three called out in FIG. 4) proximate the interior surface formed by tissue 222 of left atrium 204. In some embodiments, at least some of the transducers 220 may be configured to sense a physical characteristic of a fluid (e.g., blood) or tissue 222, or both, that may be used to determine tissue contact. In some embodiments, at least some of the transducers 220 may be configured to selectively ablate portions of the tissue 222. For example, some of the transducers 220 may be configured to ablate a pattern around one or more of the bodily openings, ports, or pulmonary vein ostia, for instance, to reduce or eliminate the occurrence of atrial fibrillation. In some embodiments, at least some of the transducers 220 are configured to ablate cardiac tissue. In some embodiments, at least some of the transducers 220 are configured to sense or sample intracardiac voltage data or sense or sample intracardiac electrogram data. In some embodiments, at least some of the transducers 220 are configured to sense or sample intracardiac voltage data or sense or sample intracardiac electrogram data while at least some of the transducers 220 are concurrently ablating cardiac tissue. In some embodiments, at least one of the sensing or sampling transducers 220 is provided by at least one of the ablating transducers 220. In some embodiments, at least a first one of the transducers 220 senses or samples intracardiac voltage data or intracardiac electrogram data at a location at least proximate a tissue location ablated by at least a second one of the transducers 220. In some embodiments, the first one of the transducers 220 is other than the second one of the transducers 220.

Figure 5:
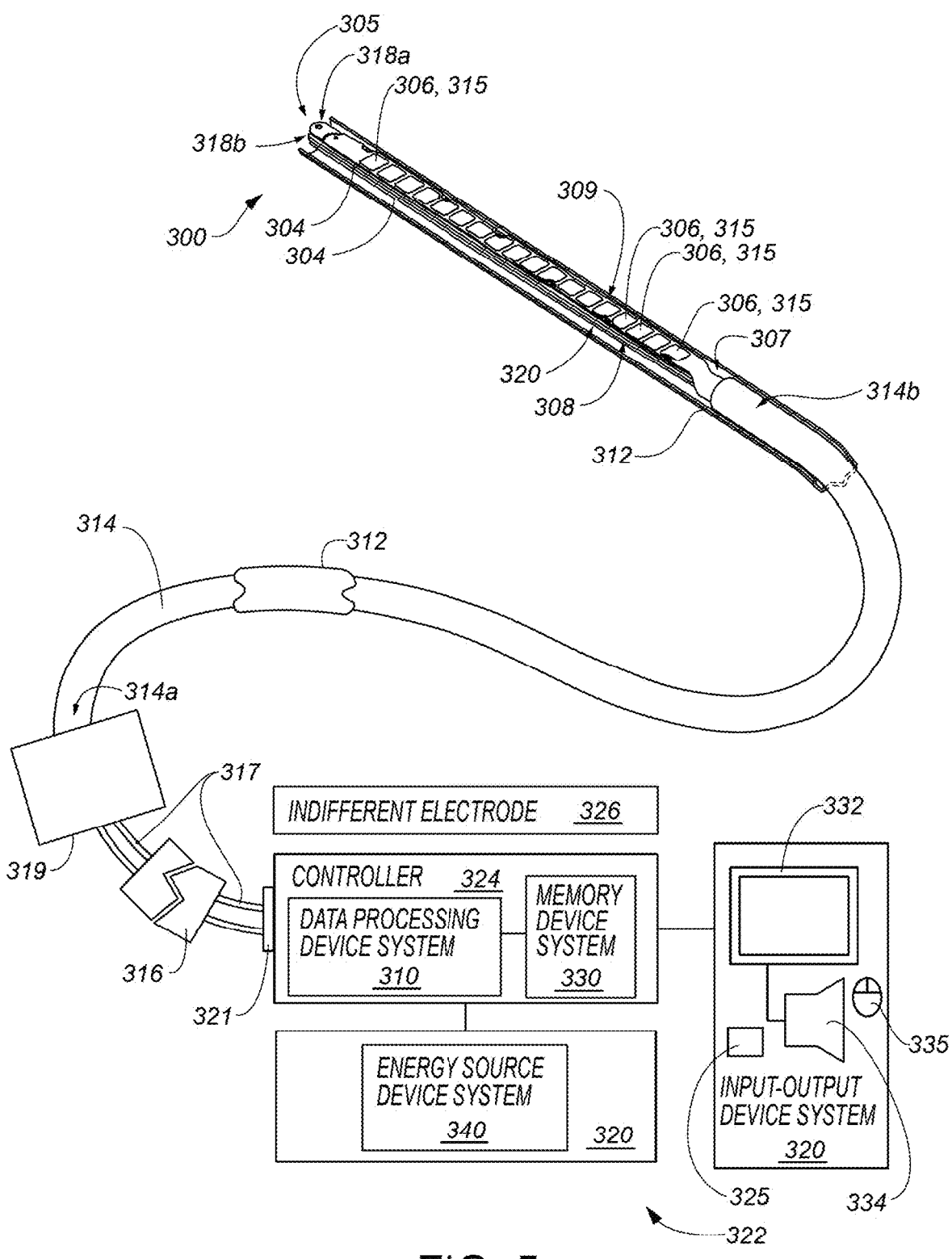
FIG. 5 includes a partially schematic representation of at least a portion of a medical system according to various example embodiments, the medical system including a data processing device system, an input-output device system, a memory device system, and may include a transducer-based device, the transducer-based device including a plurality of transducers and an expandable structure shown in a delivery or unexpanded configuration, according to various example embodiments.
Figure 6:
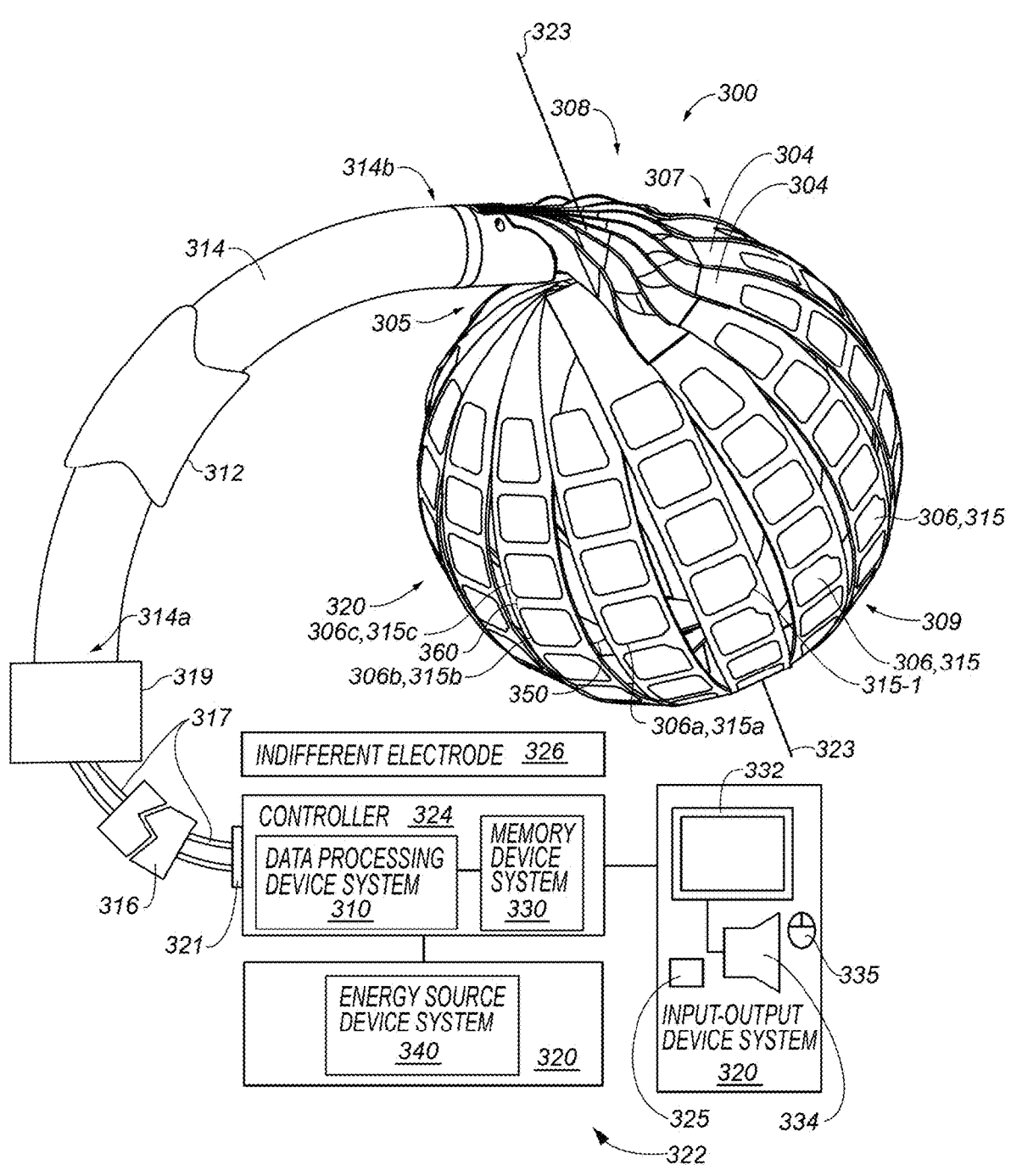
FIG. 6 includes the representation of the portion of the medical system of FIG. 5 with the expandable structure shown in a deployed or expanded configuration, according to various example embodiments.

FIGS. 5 and 6 include a catheter device system (e.g., a portion thereof shown schematically) that includes a medical device 300, according to some embodiments. All or part of such catheter device system may be all, or part of, a tissue ablation system or sensing system, according to various embodiments. All or part of such catheter device system may be all or part of a medical system, such as medical system 100 shown in FIG. 1, according to various embodiments. As noted above, the controller 324 may be a particular implementation of the data processing device system 110 shown in FIG. 1.

The medical device 300 may be the same as the medical device 200, although different sizes, numbers of transducers, or types of medical devices, such as balloon catheters, may be implemented. In this regard, medical device 300 includes a plurality of elongate members 304 (not all of the elongate members are called out in FIGS. 5 and 6) and a plurality of transducers 306 (not all of the transducers are called out in FIGS. 5 and 6; some of the transducers 306 are called out in FIG. 6 as 306a, 306b, and 306c). FIG. 5 includes a representation of a portion of the medical device 300 in a delivery or unexpanded configuration. FIG. 6 includes a representation of a portion of the medical device 300 in an expanded or deployed configuration. It is noted that, for clarity of illustration, all of the elongate members shown in FIG. 6 are not represented in FIG. 5. As will become apparent, the plurality of transducers 306 is positionable within a bodily cavity, such as with the medical device 200. For example, in some embodiments, the transducers 306 are able to be positioned in a bodily cavity by movement into, within, or into and within the bodily cavity, with or without a change in a configuration of the plurality of transducers 306. In some embodiments, the transducers of the plurality of transducers 306 are arranged to form a two- or three-dimensional distribution, grid or array of the transducers capable of mapping, ablating, or stimulating an inside surface of a bodily cavity or lumen without requiring mechanical scanning. As shown, for example, in FIG. 5, the plurality of transducers 306 are arranged in a distribution receivable in a bodily cavity. In FIGS. 5 and 6, each of at least some of transducers 306 includes a respective electrode 315 (not all of the electrodes 315 are called out in FIGS. 5 and 6).

The elongate members 304 are arranged in a frame or structure 308 that is selectively moveable between an unexpanded or delivery configuration (e.g., as shown in FIG. 5) and an expanded or deployed configuration (e.g., as shown in at least FIG. 6) that may be configured to position elongate members 304 against a tissue surface within the bodily cavity or position the elongate members 304 in the vicinity of the tissue surface. In some embodiments, structure 308 has a size in the unexpanded or delivery configuration suitable for delivery through a bodily opening (e.g., via catheter sheath 312) to the bodily cavity. In various embodiments, catheter sheath 312 typically includes a length sufficient to allow the catheter sheath to extend between a location at least proximate a bodily cavity into which the structure 308 is to be delivered and a location outside a body comprising the bodily cavity. In some embodiments, structure 308 has a size in the expanded or deployed configuration too large for delivery through a bodily opening (e.g., via catheter sheath 312) to the bodily cavity. The elongate members 304 may form part of a flexible circuit structure (e.g., also known as a flexible printed circuit board (PCB) circuit, examples of which are described with respect to FIG. 7, below). The elongate members 304 may include a plurality of different material layers. Each of the elongate members 304 may include a plurality of different material layers. The structure 308 may include a shape memory material, for instance, Nitinol. The structure 308 may include a metallic material, for instance, stainless steel, or non-metallic material, for instance, poly-imide, or both a metallic and non-metallic material by way of non-limiting example. The incorporation of a specific material into structure 308 may be motivated by various factors including the specific requirements of each of the unexpanded or delivery configuration and expanded or deployed configuration, the required position or orientation (e.g., pose), or both of structure 308 in the bodily cavity, the requirements for successful ablation of a desired pattern, or the effect that the material may have on electric or magnetic fields to be sensed by the device (e.g., by one or more transducers 306 or one or more magnetic field transducers 261).

Figure 7:
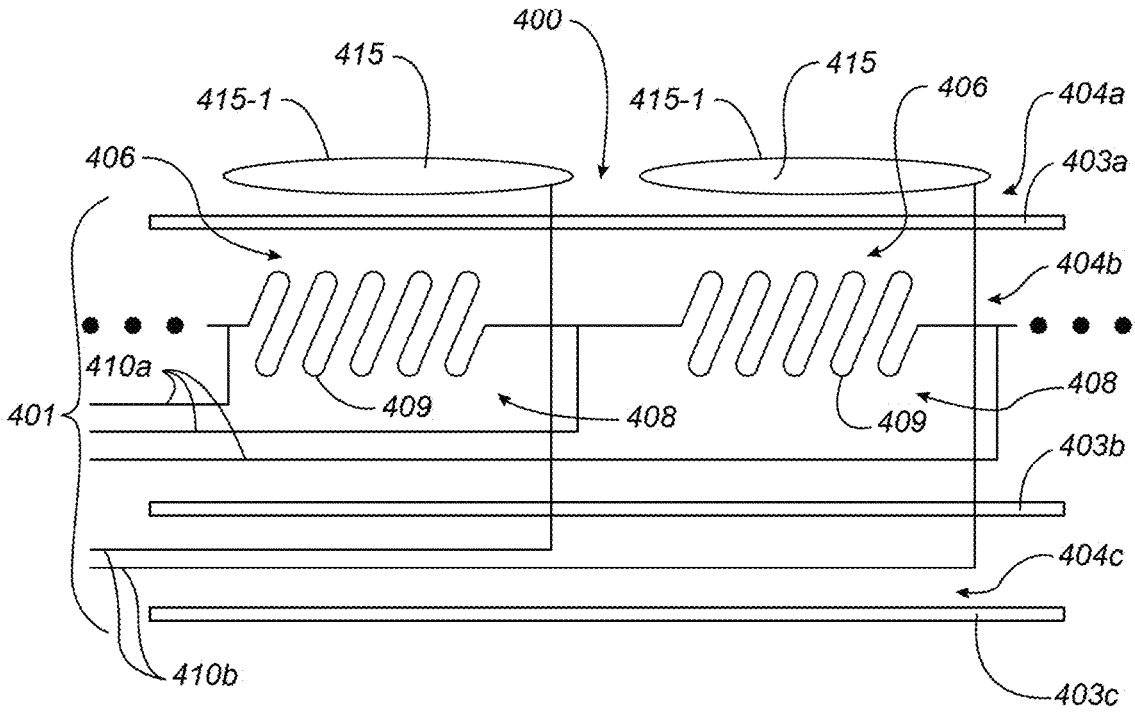
FIG. 7 includes a schematic representation of a transducer-based device that includes a flexible circuit structure, according to various example embodiments.

FIG. 7 is a schematic side elevation view of at least a portion of a medical device 400 that includes a flexible circuit structure 401 that is configured to provide a plurality of transducers 406 (two called out), according to some embodiments. All or part of such medical device 400 may form all or part of a medical system, such as part of medical system 100 shown in FIG. 1, according to various embodiments. In some embodiments, the flexible circuit structure 401 may form part of a structure (e.g., structure 218 or 308) that is selectively moveable between a delivery configuration sized for percutaneous delivery and expanded or deployed configurations sized too large for percutaneous delivery. In some embodiments, the flexible circuit structure 401 may be located on, or form at least part of, a structural component (e.g., elongate member 304) of a transducer-based device system.

The flexible circuit structure 401 may be formed by various techniques including flexible printed circuit techniques. In some embodiments, the flexible circuit structure 401 includes various layers including flexible layers 403a, 403b, and 403c (e.g., collectively flexible layers 403). In some embodiments, each of flexible layers 403 includes an electrical insulator material (e.g., polyimide). One or more of the flexible layers 403 may include a different material than another of the flexible layers 403. In some embodiments, the flexible circuit structure 401 includes various electrically conductive layers 404a, 404b, and 404c (collectively electrically conductive layers 404) that are interleaved with the flexible layers 403. In some embodiments, each of the electrically conductive layers 404 is patterned to form various electrically conductive elements. For example, electrically conductive layer 404a may be patterned to form a respective electrode 415 of each of the transducers 406. Electrodes 415 may have respective electrode edges 415-1 that form a periphery of an electrically conductive surface associated with the respective electrode 415. It is noted that other electrodes employed in other embodiments may have electrode edges arranged to form different electrode shapes (for example, as shown by electrode edge 315-1 in FIG. 6).

Electrically conductive layer 404b is patterned, in some embodiments, to form respective temperature sensors 408 for each of the transducers 406, as well as various leads 410a arranged to provide electrical energy to the temperature sensors 408. In some embodiments, each temperature sensor 408 includes a patterned resistive member 409 (two called out) having a predetermined electrical resistance. In some embodiments, each resistive member 409 includes a metal having relatively high electrical conductivity characteristics (e.g., copper). In some embodiments, electrically conductive layer 404c is patterned to provide portions of various leads 410b arranged to provide an electrical communication path to electrodes 415. In some embodiments, leads 410b are arranged to pass though vias in flexible layers 403a and 403b to connect with electrodes 415. Although FIG. 7 shows flexible layer 403c as being a bottom-most layer, some embodiments may include one or more additional layers underneath flexible layer 403c, such as one or more structural layers, such as a steel or composite layer. These one or more structural layers, in some embodiments, are part of the flexible circuit structure 401 and can be part of, e.g., elongate member 304. In some embodiments, the one or more structural layers may include at least one electrically conductive surface (e.g., a metallic surface) exposed to blood flow. In addition, although FIG. 7 shows only three flexible layers 403a-403c and only three electrically conductive layers 404a-404c, it should be noted that other numbers of flexible layers, other numbers of electrically conductive layers, or both, may be included.

In some embodiments, electrodes 415 are employed to selectively deliver thermal ablation energy (e.g., RF energy) to various tissue structures within a bodily cavity (not shown in FIG. 7) (e.g., an intracardiac cavity or chamber). In some embodiments, the thermal energy may be delivered in the form of a continuous waveform. In some embodiments, the thermal ablation energy may be delivered in the form of plurality of discrete energy applications (e.g., in the form of a duty-cycled waveform). The thermal energy delivered to the tissue may be delivered to cause monopolar thermal tissue ablation, bipolar thermal tissue ablation, or blended monopolar-bipolar thermal tissue ablation by way of non-limiting example.

In some embodiments, electrodes 415 are employed to selectively deliver discrete energy applications in the form of PFA high voltage pulses to various tissue structures within a bodily cavity (not shown in FIG. 7) (e.g., an intracardiac cavity or chamber). The PFA high voltage pulses delivered to the tissue structures may be sufficient for ablating portions of the tissue structures. The PFA high voltage pulses delivered to the tissue may be delivered to cause monopolar pulsed field tissue ablation, bipolar pulsed field tissue ablation, or blended monopolar-bipolar pulsed field tissue ablation by way of non-limiting example. The energy that is delivered by each high voltage pulse may be dependent upon factors including the electrode location, size, shape, relationship with respect to another electrode (e.g., the distance between adjacent electrodes that deliver the PFA energy), the presence, or lack thereof, of various material between the electrodes, the degree of electrode-to-tissue contact, and other factors.

In some embodiments, each electrode 415 is configured to sense or sample an electric potential in the tissue proximate the electrode 415 at a same or different time than delivering energy sufficient for tissue ablation. In some embodiments, each electrode 415 is configured to sense or sample intracardiac voltage data in the tissue proximate the electrode 415. In some embodiments, each electrode 415 is configured to sense or sample data in the tissue proximate the electrode 415 from which an electrogram (e.g., an intracardiac electrogram) may be derived. In some embodiments, each resistive member 409 is positioned adjacent a respective one of the electrodes 415. In some embodiments, each of the resistive members 409 is positioned in a stacked or layered array with a respective one of the electrodes 415 to form a respective one of the transducers 406. In some embodiments, the resistive members 409 are connected in series to allow electrical current to pass through all of the resistive members 409. In some embodiments, leads 410*a* are arranged to allow for a sampling of electrical voltage in between each resistive member 409. This arrangement allows for the electrical resistance of each resistive member 409 to be accurately measured. The ability to accurately measure the electrical resistance of each resistive member 409 may be motivated by various reasons including determining temperature values at locations at least proximate the resistive member 409 based at least on changes in the resistance caused by convective cooling effects (e.g., as provided by blood flow). The resistance data can thus be correlated to the degree of presence of blood flow between the electrode 415 and tissue, thereby allowing the degree of contact between the electrode 415 and the tissue to be determined. Other methods of detecting transducer-to-tissue contact or degrees of transducer-to-tissue contact may be employed according to various example embodiments.

Referring to FIGS. 5 and 6, medical device 300 can communicate with, receive power from or be controlled by a transducer-activation device system 322 according to some embodiments. In some embodiments, at least part of the transducer-activation device system 322 represents one or more particular implementations of the system 100 illustrated in FIG. 1. In some embodiments, elongate members 304 include transducers 306 that are communicatively connected to a data processing device system 310 via electrical connections running within elongate shaft member 314 that are communicatively connected to one or more of electrical leads 317 (e.g., control leads, data leads, power leads or any combination thereof) within elongated cable 316 (only a portion of which is shown in FIGS. 5 and 6 to reveal other structures) terminating at a connector 321 or other interface. The leads 317 may correspond to the electrical conductors 216 in FIG. 4 in some embodiments and, although only two leads 317 are shown for clarity, more may be present. The transducer-activation device system 322 may include a controller 324 that includes the data processing device system 310 (e.g., which may be a particular implementation of data processing device system 110 from FIG. 1) and a memory device system 330 (e.g., which may be a particular implementation of the memory device system 130 from FIG. 1) that stores data and instructions that are executable by the data processing device system 310 to process information received from medical device 300 or to control operation of medical device 300, for example, activating various selected transducers 306 to ablate tissue and control a user interface (e.g., of input-output device system 320) according to various embodiments. Controller 324 may include one or more controllers.

Transducer-activation device system 322 includes an input-output device system 320 (e.g., which may be a particular implementation of the input-output device system 120 from FIG. 1) communicatively connected to the data processing device system 310 (e.g., via controller 324 in some embodiments). Input-output device system 320 may include a user-activatable control that is responsive to a user action. Input-output device system 320 may include one or more user interfaces or input/output (I/O) devices, for example, one or more display device systems 332, speaker device systems 334, one or more keyboards, one or more mice (e.g., mouse 335), one or more joysticks, one or more track pads, one or more touch screens or other transducers to transfer information to, from, or both to and from a user, for example a care provider such as a physician or technician. For example, output from a mapping process may be displayed by a display device system 332. Input-output device system 320 may include one or more user interfaces or input/output (I/O) devices, for example, one or more display device systems 332, speaker device systems 334, keyboards, mice, joysticks, track pads, touch screens or other transducers employed by a user to indicate a particular selection or series of selections of various graphical information. Input-output device system 320 may include a sensing device system 325 configured to detect various characteristics including, but not limited to, at least one of tissue characteristics (e.g., electrical characteristics such as tissue impedance, electric potential of a tissue surface, tissue conductivity, tissue type, tissue thickness) and thermal characteristics such as temperature. In this regard, the sensing device system 325 may include one, some, or all, of the transducers 306 (or 220 in FIG. 4 or 406 of FIG. 7) of the medical device 300, including the internal components of such transducers shown in FIG. 7, such as the electrodes 415 and temperature sensors 408.

Transducer-activation device system 322 may also include an energy source device system 340 including one or more energy source devices connected to transducers 306. In this regard, although FIGS. 5 and 6 show a communicative connection between the energy source device system 340 and the controller 324 (and its data processing device system 310), the energy source device system 340 may also be connected to the transducers 306 via a communicative connection that is independent of the communicative connection with the controller 324 (and its data processing device system 310). For example, the energy source device system 340 may receive control signals via the communicative connection with the controller 324 (and its data processing device system 310), and, in response to such control signals, deliver energy to, receive energy from, or both deliver energy to and receive energy from one or more of the transducers 306 via a communicative connection with such transducers 306 (e.g., via one or more communication lines through catheter body or elongate shaft member 314, elongated cable 316 or catheter sheath 312) that does not pass through the controller 324. In this regard, the energy source device system 340 may provide results of its delivering energy to, receiving energy from, or both delivering energy to and receiving energy from one or more of the transducers 306 to the controller 324 (and its data processing device system 310) via the communicative connection between the energy source device system 340 and the controller 324.

The energy source device system 340 may, for example, be connected to various selected transducers 306 to selectively provide energy in the form of electrical current or power, light, low temperature fluid, or another form to the various selected transducers 306 to cause ablation of tissue. The energy source device system 340 may, for example, selectively provide energy in the form of electrical current to various selected transducers 306 and measure a temperature characteristic, an electrical characteristic, or both at a respective location at least proximate each of the various transducers 306. The energy source device system 340 may include various electrical current sources or electrical power sources as energy source devices. In some embodiments, an indifferent electrode 326 is provided to receive at least a portion of the energy transmitted by at least some of the transducers 306. Consequently, although not shown in FIGS.

5 and 6, the indifferent electrode 326 may be communicatively connected to the energy source device system 340 via one or more communication lines in some embodiments. In addition, although shown separately in each of FIGS. 5 and 6, indifferent electrode 326 may be considered part of the energy source device system 340 in some embodiments. In various embodiments, indifferent electrode 326 is positioned on an external surface (e.g., a skin-based surface) of a body that comprises the bodily cavity into which at least transducers 306 are to be delivered.

It is understood that input-output device system 320 may include other systems. In some embodiments, input-output device system 320 may optionally include energy source device system 340, medical device 300 or both energy source device system 340 and medical device 300 by way of non-limiting example. Input-output device system 320 may include the memory device system 330 in some embodiments.

Structure 308 may be delivered and retrieved via a catheter member, for example, a catheter sheath 312. In some embodiments, a structure provides expansion and contraction capabilities for a portion of the medical device (e.g., an arrangement, distribution or array of transducers 306). The transducers 306 may form part of, be positioned or located on, mounted or otherwise carried on the structure and the structure may be configurable to be appropriately sized to slide within catheter sheath 312 in order to be deployed percutaneously or intravascularly. FIGS. 5 and 6 show one embodiment of such a structure. In some embodiments, each of the elongate members 304 includes a respective distal end 305 (only one called out in each of FIGS. 5 and 6), a respective proximal end 307 (only one called out in each of FIGS. 5 and 6) and a respective intermediate portion 309 (only one called out in each of FIGS. 5 and 6) positioned between the proximal end 307 and the distal end 305. The respective intermediate portion 309 of each elongate member 304 includes a first or front surface 318a that is positionable to face an interior tissue surface within a bodily cavity and a second or back surface 318b opposite across a thickness of the intermediate portion 309 from the front surface 318a. In some embodiments, the elongate members 304 are arranged front surface 318a toward back surface 318b in a stacked array during an unexpanded or delivery configuration similar to that described in International Publication No. WO 2012/100184, published Jul. 26, 2012 (Lopes et al.) and International Publication No. WO 2012/100185, published Jul. 26, 2012 (Lopes et al.). In many cases, a stacked array allows the structure 308 to have a suitable size for percutaneous or intravascular delivery. In some embodiments, the elongate members 304 are arranged to be introduced into a bodily cavity distal end 305 first. An elongate shaft member 314 is configured to deliver structure 308 through catheter sheath 312, according to some embodiments. According to various embodiments, the elongate shaft member 314 includes a proximal end portion 314a and a distal end portion 314b, the distal end portion 314b physically coupled to structure 308. According to various embodiments, the elongate shaft member 314 may include a length to position distal end portion 314b (and structure 308 in some embodiments) at a desired location within a patient's body while maintaining the proximal end portion 314a at a location outside the patient's body. In some embodiments, the proximal end portion 314a may be coupled to a housing 319. Housing 319 may include or enclose various actuators that may be configured to manipulate various portions of the catheter, including, but not limited to, (a) portions of the elongate shaft member 314, portions of structure 308, or both (a) and (b). According to various embodiments, housing 319 may take the form of a handle that is directly manipulable by a user. U.S. Pat. No. 9,452,016, issued Sep. 27, 2016 (Moisa et al.), provides possible examples of a housing and accompanying actuators that may be utilized as housing 319.

The transducers 306 can be arranged in various distributions or arrangements in various embodiments. In some embodiments, various ones of the transducers 306 are spaced apart from one another in a spaced apart distribution in the delivery configuration shown in FIG. 5. In some embodiments, various ones of the transducers 306 are arranged in a spaced apart distribution in the deployed configuration shown in at least FIG. 6. In some embodiments, various pairs of transducers 306 are spaced apart with respect to one another. In some embodiments, various regions of space are located between various pairs of the transducers 306. For example, in FIG. 6, the medical device 300 includes at least a first transducer 306a, a second transducer 306b, and a third transducer 306c (all collectively referred to as transducers 306). In some embodiments, each of the first, the second, and the third transducers 306a, 306b, and 306c are adjacent transducers in the spaced apart distribution. In some embodiments, the first and the second transducers 306a, 306b are located on different elongate members 304, while the second and the third transducers 306b, 306c are located on a same elongate member 304. In some embodiments, a first region of space 350 is between the first and the second transducers 306a, 306b. In various embodiments, a first region of space 350 is between the respective electrodes 315a, 315b of the first and the second transducers 306a, 306b. In some embodiments, the first region of space 350 is not associated with any physical portion of structure 308. In some embodiments, a second region of space 360 associated with a physical portion of medical device 300 (e.g., a portion of an elongate member 304) is between the second and the third transducers 306b, 306c (and their respective electrodes 315b, 315c). In various embodiments, the second region of space 360 is between the respective electrodes 315b, 315c of the second and the third transducers 306b, 306c. In some embodiments, each of the first and the second regions of space 350, 360 does not include a transducer of medical device 300. In some embodiments, each of the first and the second regions of space 350, 360 does not include any transducer. It is noted that other embodiments need not employ a group of elongate members 304 as employed in the illustrated embodiment. For example, other embodiments may employ a structure having one or more surfaces, at least a portion of the one or more surfaces defining one or more openings in the structure. In these embodiments, a region of space not associated with any physical portion of the structure may extend over at least part of an opening of the one or more openings. In some embodiments, the transducers of the plurality of transducers (e.g., at least a group of the transducers 306) may be circumferentially arranged about an axis (e.g., axis 323, FIG. 6) of the structure 308 at least in the state in which the structure 308 is in the deployed configuration. In other example embodiments, other structures may be employed to support or carry transducers of a transducer-based device such as a transducer-based catheter. For example, an elongated catheter member may be used to distribute the transducers in a linear or curvilinear array. Basket catheters or balloon catheters may be used to distribute the transducers in a two-dimensional or three-dimensional array.

According to some embodiments, a system is provided that may include an input-output device system (e.g., input-output device system 120, 320) that may, in some embodiments, include a catheter that includes a plurality of transducers (e.g., transducers 220, 306, 406). The catheter may include the catheter body to which the plurality of transducers (or the structure on which the transducers reside) is physically coupled (e.g., catheter 206, and elongate shaft member 314). In some embodiments, the catheter may also include other components such as catheter sheath 312. According to various embodiments, different portions of the catheter are manipulable to in turn manipulate various ones of the plurality of transducers (e.g., transducers 220, 306, 406) into various degrees of contact with a tissue wall within a patient's body (e.g., patient 361). According to various embodiments, at least some transducers (e.g., at least some of the transducers 220, 306, 406), such as a first set of transducers, of the plurality of transducers of the catheter device system are arranged in a first spatial distribution (e.g., the spaced apart distribution associated with the deployed configuration of FIG. 6), the distribution positionable in a bodily cavity of a patient. The bodily cavity is defined by at least a tissue wall, and, according to various embodiments, each transducer of the at least some transducers, such as at least the first set of transducers of the plurality of transducers, is configured at least to sense a degree of contact between the transducer and the tissue wall. In some embodiments, each particular transducer of the at least some transducers (e.g., at least the first set of transducers) of the plurality of transducers of the catheter may be configured to sense or detect a degree of transducer-to-tissue contact between at least a portion of the particular transducer and the tissue wall. Various methods may be executed to determine the degree of transducer-to-tissue contact including, by way of non-limiting example, techniques including sensing impedance, sensing permittivity, sensing the presence or absence of flow of a fluid (e.g., a bodily fluid), or by sensing contact force or pressure. U.S. Pat. No. 8,906,011, issued Dec. 9, 2014 (Gelbart et al.), describes example transducer sensing techniques. In some embodiments, the tissue-contacting portion of the transducer itself directly senses the degree of tissue contact. In some embodiments, a portion of the transducer other than the tissue-contacting portion of the transducer is configured to sense the degree of contact between the tissue wall and the tissue-contacting portion of the transducer. In some embodiments, the tissue-contacting portion of the transducer is provided by an electrode.

According to some embodiments, the at least some transducers (e.g., at least the first set of transducers) of the plurality of transducers of the catheter (e.g., medical device 200 or medical device 300) may be configured to provide a plurality of contact signal sets to the controller 324 or its data processing device system 310. Each contact signal set may indicate a degree of transducer-to-tissue contact between each transducer (e.g., a transducer 220, 306, 406) and a tissue surface in the bodily cavity.

In some embodiments, at least some transducers (e.g., at least some of the transducers 220, 306, 406), such as a second set of transducers, of the plurality of transducers of the catheter are configured to sense one or more electrical properties or characteristics of or generated at least in part by a body (e.g., the body of the patient 361) including the bodily cavity. In some embodiments, such transducers (e.g., at least the second set of transducers) may be configured to provide a plurality of tissue-electrical-information signal sets to the controller 324 or its data processing device system 310. In some embodiments, such transducers (e.g., at least the second set of transducers) may be configured to provide a plurality of tissue-electrical-information signal sets (e.g., electrophysiological signal sets) to the controller 324 or its data processing device system 310 throughout movement of at least a portion of the catheter (e.g., medical device 200 or medical device 300) among a sequence of locations of the at least the portion of the catheter in the bodily cavity. In some embodiments, the plurality of tissue-electrical-information signal sets indicate an electrical property set of or associated at least in part with a body including the bodily cavity and detected by at least the second set of transducers. The electrical property set may be tissue electrical characteristics as discussed above, possibly including different electrical property types, such as electric potential or electrical impedance, e.g., as detected by the respective transducers (e.g., transducers 220, 306, 406). In some embodiments, the plurality of tissue-electrical-information signal sets are generated by and provided to (and consequently, are received by) the controller 324 or its data processing device system 310 at least in a state representative of the second set of transducers being located in the bodily cavity. The state associated with the second set of transducers being located in the bodily cavity may be a state in which the second set of transducers are actually located in the bodily cavity, or may be, e.g., a simulation state in which it is simulated, e.g., for quality-control, training, or testing, that the second set of transducers are located in the bodily cavity, although they are not actually so located. In some embodiments, the second set of transducers (which may be configured to sense one or more electrical properties or characteristics of or generated at least in part by a body) and the first set of transducers (which may be configured to sense or detect a degree of transducer-to-tissue contact between at least a portion of the respective transducer and the tissue wall) may be the same one or more transducers (e.g., transducers 220, 306, 406). In other embodiments, the first set of transducers, the second set of transducers, or the first and second sets of transducers include at least one transducer not included in the other set. Transducer-to-tissue contact between at least a portion of the respective transducer and the tissue wall may be determined via various techniques, including those described above in this disclosure.

In some embodiments, one or more devices of the catheter-device-location tracking system or catheter navigation system shown in at least FIG. 2 or FIG. 3 is or are configured to provide location information derived from a plurality of location signal sets to (and consequently, received by) the controller 324 or its data processing device system 310. According to various embodiments, the location information may indicate a plurality of locations in a bodily cavity in response to movement of at least a portion of a medical device (e.g., medical device 200, 300, or 400 in some embodiments) in the bodily cavity. In some embodiments, each location signal set may be indicative of a respective location of the plurality of locations. In some embodiments, the location information may indicate movement of at least a portion of a medical device (e.g., medical device 200, 300, or 400 in some embodiments) through or between a plurality of locations in a bodily cavity. In some embodiments, each location signal set may be indicative of a respective location of the plurality of locations. In some embodiments, each location signal set may be indicative of a respective location in a sequence of locations at which at least a portion of a medical device (e.g., catheter) has been sequentially located in a bodily cavity, according to some embodiments. For example, with respect to at least FIG. 2 or FIG. 3, at least a portion of the catheter or medical device (e.g., medical device 200, 300, or 400) may be moved or progressed through a sequence of locations in a chamber of the heart or other bodily cavity of a patient 361 (or through a quality-control, training, or testing environment) in the presence of an electric field set (e.g., one or more electric fields generated by the external electrodes 256a, 256b, 256c, 256d, 256e, 256f) or a magnetic field set (e.g., one or more magnetic fields generated by magnetic field generation sources 257w, 257x, 257y). As the portion of the catheter is moved through the sequence of locations, at least some of the catheter's transducers (e.g., transducers 220, 306, 406 (or, e.g., 261 in the case of magnetic-field-based systems)) may be configured to generate each location signal set as detected voltage(s) or strength(s) of the respective field(s), which the controller 324 or its data processing device system 310 may then be configured to utilize to generate a three-dimensional location of the at least the portion of the medical device 200, 300, or 400) or its transducers (e.g., transducers 220, 306, 406 (or, e.g., 261 in the case of magnetic-field-based systems)) for the respective location in the sequence of locations, according to some embodiments. In this regard, in some embodiments, the navigation system may be deemed to include the respective transducer(s) (e.g., transducers 220, 306, 406 (or, e.g., 261 in the case of some magnetic-field-based systems)) that detected voltage(s) or the field strength(s), the field-generating devices (e.g., the external electrodes 256a, 256b, 256c, 256d, 256e, 256f in the case of electric field(s); and, e.g., magnetic field generation sources 257w, 257x, 257y in the case of magnetic field(s)), or both the respective transducers and the field-generating devices. In some embodiments, the controller 324 or its data processing device system 310 may be considered at least part of the navigation system.

At least in light of the above discussion, in some embodiments, the navigation system is configured to generate location information that may be derived from one or more location signal sets at least in response to one or more electric or magnetic fields producible by one or more devices of the navigation system. In some embodiments, the one or more devices that generate the one or more electric or magnetic fields may be configured to operate outside a body including the bodily cavity, such as the external electrodes 256a, 256b, 256c, 256d, 256e, 256f in the case of electric field(s), and magnetic field generation sources 257w, 257x, 257y in the case of magnetic field(s). According to some embodiments, the electric or magnetic field sensing devices of the medical device (e.g., transducers 220, 306, 406 or one or more magnetic field transducers 261) are configured to generate location information at least in response to the one or more electric or magnetic fields producible by one or more devices of the navigation system. In this regard, the navigation system, in some embodiments, may include the transducers 220, 306, 406 (or, e.g., 261 in the case of magnetic-field-based systems) of the medical device that sense the one or more electric or magnetic fields and consequently generate the plurality of location signal sets. According to some embodiments, each transducer of at least some of the transducers of the medical device (e.g., medical device 200, 300, or 400 in some embodiments) is configured to not only sense an electric field for location determination purposes, but also to perform one or more other functions (e.g., ablation, pacing, tissue electric potential detecting or measuring, transducer-to-tissue contact detecting or measuring, etc.). In some embodiments, the navigation system may be configured to provide location information to (which is, consequently, received by) the controller 324 or its data processing device system 310, the location information indicating locations of at least a portion of a medical device (e.g., medical device 200, 300, or 400).

For example, in some embodiments, the location information may be based at least on, or include (a) a location of the at least the portion of the medical device from sensed electric or magnetic fields generated by the navigation system, and (b) transducer-to-tissue-contact sensing results provided by transducers of the transducer-based device. However, in some embodiments, a location of the at least the portion of the medical device may be indicated at least by (a), and not (b), for example, when (a) is determined with respect to a 3D model of the bodily cavity. In some embodiments, the location information indicates locations of at least a portion of a medical device (e.g., medical device 200, 300, or 400) relative to a tissue surface in a bodily cavity. In some embodiments, the location information indicates locations of at least a portion of a medical device (e.g., medical device 200, 300, or 400) relative to a reference device (e.g., reference device 252 (FIG. 2) or reference device 257z (FIG. 3), in some embodiments) of a navigation system.

In various embodiments, movement of at least a portion of a medical device (e.g., medical device 200, 300, 400) in the bodily cavity occurs during a treatment or diagnostic procedure. This movement may be motivated for different reasons. For example, a volume of space occupied by the at least the portion of the medical device in the bodily cavity is typically smaller than the volume of space that is occupied by the bodily cavity itself. Accordingly, movement of the at least the portion of the medical device may be necessitated in order to interact with different parts of the bodily cavity. For example, movement of the at least the portion of the medical device may be required to sample electrophysiological information in different regions of a cardiac cavity. In ablation procedures, movement of the at least the portion of the medical device may occur between, during, or between and during the transmission of tissue ablative energy at each of at least some of a plurality of locations in the bodily cavity. Movement of the at least the portion of the medical device may be motivated for different reasons. For example, movement of the at least the portion of the medical device between different locations can allow for the formation of a larger ablated region (e.g., a larger lesion) than would be possible if tissue ablative energy was transmitted only while the at least the portion of the medical device remained at a single location in the bodily cavity. In some embodiments, movement of the at least the portion of the medical device between a plurality of locations may be employed to form relatively long, or relatively long and continuous lesions in bodily tissue under the effects of the transmitted tissue ablative energy. In some embodiments, the continuous lesions may take the form of closed circumferential lesions (e.g., circumferential lesions surrounding an anatomical feature, such as a pulmonary vein). In some embodiments, the continuous lesions may take the form of continuous lesions connecting various anatomical features or connecting various ablated regions (for example, lesions connecting to circumferential lesions in a Cox-Maze procedure).

In some embodiments, movement of the at least the portion of the medical device (e.g., medical device 200, 300, 400, in some embodiments) in the bodily cavity may be required to generate a map or model of the bodily cavity. According to some embodiments, a catheter-device-location tracking system (e.g., catheter navigation system 260A or catheter navigation system 260B, in some embodiments) provides a plurality of location signal sets to a data processing device system (e.g., data processing device system 110, 310, in some embodiments), and a plurality of transducers (e.g., transducers 220, 306, 406) of a medical device (e.g., medical device 200, 300, 400), which may be part of the catheter-device-location tracking system, provide a plurality of contact signal sets to the data processing device system, which also may be part of the catheter-device-location tracking system. The plurality of location signal sets may be generated as a result of an interaction between transducers of the medical device, a reference device (e.g., reference device 252, 257*z*), and a generated electric or magnetic field. The plurality of location signal sets may be provided by the catheter-device-location tracking system while the at least the portion of the medical device is moving throughout the bodily cavity in real time, informing the data processing device system of a sequence of three-dimensional locations of the at least the portion of the medical device and its transducers in real time. The plurality of contact signal sets may be generated based on an interaction of the transducers with a tissue surface of the bodily cavity to detect a degree of contact between each respective transducer and the tissue surface. Such contact signal sets may also be provided to the data processing device system in real time, informing it of respective degrees of tissue contact detected by the respective transducers in real time. With the stream of location signal sets and the contact signal sets, the data processing device system may be configured to generate a graphical representation of at least a portion of an envelope representing an interior volume of the bodily cavity as the at least the portion of the medical device moves throughout the bodily cavity. In this regard, the envelope may be a three-dimensional graphical representation of an interior surface region of the bodily cavity, as well as one or more regions where one or more ports lead into or out of the bodily cavity. As the at least the portion of the medical device continues to explore new locations in the bodily cavity, the envelope is enlarged (e.g., added to) or refined in the graphical representation to represent new or revised surface regions of the bodily cavity revealed by the location signal sets and the contact signal sets from the at least the portion of the medical device's progression into the new locations, according to some embodiments. In this regard, an interior volume of the bodily cavity can be displayed to an operator in real time as it is being mapped, thereby allowing treatment to occur during the mapping process without having to wait until the entire bodily cavity is mapped prior to performing treatment, according to some embodiments. In some embodiments, treatment occurs after the mapping process is completed.

According to various embodiments, it is typically desired to manipulate the at least the portion of the medical device (e.g., medical device 200, 300, 400) back to the vicinity of a previously visited location. This may be motivated for different reasons. For example, in ablation procedures, a previously ablated tissue region in the bodily cavity may be determined to have not been effectively ablated (e.g., due to gaps in the formed lesions or inadequate transmurality). This circumstance may necessitate a repositioning of the at least the portion of the medical device back to a location in close proximity to particular ones of its several previously visited locations that correspond to the formation of the previously ablated regions. This movement to a previously ablated region typically is difficult to do for various reasons. For example, the generation of the map or the model from location and tissue contact data is typically dependent on the degree of contact between the at least the portion of the medical device and a tissue surface in the bodily cavity. Excessive amounts of contact can cause distortion of the tissue surface and, consequently, can cause distortions in the generated model. If the at least the portion of the medical device 200, 300, 400 is repositioned at what is believed (e.g., based on a visual analysis of the model) to be a previously visited location, but under a different set of tissue contact conditions, deviations in the required repositioning may occur. Further, visually ascertaining an accurate relative positioning between a model of the at least the portion of the medical device 200, 300, 400 and the model of the bodily cavity may be challenging due to the graphical three-dimensional nature of the models, viewing perspective conditions or limitations, and possible viewing obstructions due to overlapping of the models along a viewing perspective.

FIGS. 8A-8B illustrate respective programmed configurations of a data processing device system (e.g., data processing device system 110 or 310) that at least provide enhanced capabilities for identifying a particular location within a body (whether a living patient during a therapeutic or diagnostic procedure or an inanimate non-living body in a quality control or testing environment), such as a location within a bodily cavity, locating at least a portion of a medical device in a bodily cavity, identifying a relative positioning between at least a portion of a medical device and a particular location within a body, or a combination of some or all of these benefits, according to various embodiments and contexts. Such programmed configurations may be implemented by the data processing device system being communicatively connected to an input-output device system (e.g., input-output device system 120 or 320) and a memory device system (e.g., memory device system 130 or 330), and being configured by a program stored by the memory device system at least to perform one or more actions (e.g., such as at least one, more, or all of the actions described in any one or more of FIGS. 8A-8B or otherwise herein). In some embodiments in which the one or more of the programmed configurations illustrated in FIGS. 8A-8B actually is or are executed at least in part by the data processing device system, such actual execution may be considered a respective method executed by the data processing device system. In this regard, FIGS. 8A-8B may be considered to represent one or more methods in some embodiments and, for ease of communication, such one or more methods may be referred to simply as 'the method of FIG. 8A', and 'the method of FIG. 8B'. The blocks shown in each of FIGS. 8A-8B may be associated with computer-executable instructions of a program that configures the data processing device system to perform the actions described by the respective blocks. According to various embodiments, not all of the actions or blocks shown in each of FIGS. 8A-8B are required, and different orderings of the actions or blocks shown in each of FIGS. 8A-8B may exist. In this regard, in some embodiments, a subset of the blocks shown in each of FIGS. 8A-8B or additional blocks, may exist. In some embodiments, a different sequence of various ones of the blocks in each of FIGS. 8A-8B or actions described therein may exist. In FIG. 8A, some blocks are nested within other blocks, like block 802*a* in FIG. 8A is nested within block 802. Such an arrangement may indicate that the interior nested block (such as block 802*a*) may be a specific implementation of the parent, exterior block (such as block 802), in some embodiments. For instance, block 802*a* may be considered a particular implementation of block 802, in some embodiments. Also, in FIG. 8A, multiple blocks may be nested within a parent block, such as blocks 802*a*, 802*b* both being nested within block 802. In this regard, blocks 802*a* and 802*b* may be considered specific implementations of block 802, and such specific implementations may or may not coexist according to various embodiments, and the actions of such blocks, such as blocks 802*a*, 802*b* may or may not occur in the order shown in FIG. 8A, according to various embodiments. Also, in FIG. 8A, some blocks are shown in broken line to stress or highlight that the actions of such blocks are optional in some embodiments. While any block, whether illustrated in broken line or in solid line, may be optional in various embodiments, the broken line illustration merely stresses or highlights that the associated block is optional in some embodiments.

In some embodiments, a memory device system (e.g., memory device system 130 or 330, or a computer-readable medium system) stores the program(s) represented by each of FIGS. 8A-8B, and, in some embodiments, the memory device system is communicatively connected to the data processing device system as a configuration thereof. In this regard, in various example embodiments, a memory device system is communicatively connected to a data processing device system (e.g., data processing device systems 110 or 310) and stores a program executable by the data processing device system to cause the data processing device system to execute various actions described by, or otherwise associated with, the blocks illustrated in each of FIGS. 8A-8B for performance of some or all of the corresponding method(s) via interaction with at least, for example, a medical device (e.g., medical device 200, 300, or 400, in some embodiments). In these various embodiments, the program may include instructions configured to perform, or cause to be performed, various ones of the block actions described by or otherwise associated with one, or more, or all of the blocks illustrated in each of FIGS. 8A-8B for performance of some, or all, of the corresponding method(s).

FIG. 8A shows a respective data generation and flow diagram, which may implement various embodiments of method 800A by way of associated computer-executable instructions provided by a program, according to some example embodiments. According to some embodiments, block 802 is associated with computer-executable instructions provided by the program and configured to cause the data processing device system (e.g., 110, 310) to cause, via the input-output device system (e.g., 120, 320), display of a particular graphical representation. A sequence of FIGS. 9A-9K shows, according to some embodiments, an example of a such a particular graphical representation 900, the particular graphical representation 900 undergoing changes that may be caused, in some embodiments, at least in part in response to movement of at least a portion of a medical device within a bodily cavity or a simulated bodily cavity in quality control, training, or testing environments. The particular graphical representation 900 may be produced at least in part by a data processing device system (e.g., 110, 310) and presented, e.g., by one or more display devices of an input output device system (e.g., 120, 320) communicatively connected to the data processing device system.

In some embodiments, the changes made to the particular graphical representation through the sequence of FIGS. 9A-9K may highlight, enhance the visibility of, or otherwise call a user's attention to a location of a portion of the medical device, a location in a patient, such as a location in a bodily cavity in some embodiments, or a relative positioning between a portion of the medical device and the location within the patient. In some embodiments, the location within the patient is a location of an anatomical feature of the bodily cavity. In some embodiments, the changes made to the particular graphical representation through the sequence of FIGS. 9A-9K are not based on or in response to movement of the medical device.

According to various embodiments associated with FIGS. 9A-9K, the particular graphical representation 900 includes various graphical representations of one or more particular volumes within a bodily cavity (e.g., a cardiac cavity) of a patient. For instance, in some embodiments, with respect to FIG. 4, such a particular volume may be all or a portion of a volume 905 of the left atrium 204 or may be all or a portion of a volume 904 encompassed by the structure 218 of the medical device 200 when the structure 218 is in an expanded configuration in a state in which the structure 218 is located within the left atrium 204. The graphical representations of the particular volumes within the bodily cavity may be representative of different volumes within the bodily cavity and may be depicted in different manners according to various embodiments. It is noted that, while the particular graphical representations 900 in each of FIGS. 9A-9K includes different portions (e.g., 902A, 902B), each portion including a graphical representation of at least one particular volume within the bodily cavity, these portions of the particular graphical representation 900 need not be displayed collectively on a single display device, but may be displayed separately on different display devices. In some embodiments, not all of the different portions (e.g., 902A, 902B) of the particular graphical representations 900 in each of FIGS. 9A-9K need to be included. In some embodiments associated with FIGS. 9A-9K and block 802*a* in FIG. 8A, various volumes within the bodily cavity are depicted three-dimensionally as shown by the portion 902A of the particular graphical representation 900. In this regard, according to some embodiments, block 802*a* is associated with computer-executable instructions provided by the program and configured to cause the data processing device system (e.g., 110, 310) to cause, via the input-output device system (e.g., 120, 320), display of a particular graphical representation including a three-dimensional graphical representation of a first volume within a bodily cavity. In some embodiments, block 802*a* is associated with computer-executable instructions provided by the program and configured to cause the data processing device system (e.g., 110, 310) to cause, via the input-output device system (e.g., 120, 320), display of a three-dimensional graphical representation of a first volume within a bodily cavity. For example, FIG. 9A includes a graphically depicted three-dimensional graphical representation 904A of a volume that corresponds to or represents a volume occupied by at least a portion of the medical device 200, 300, 400. For example, such volume occupied by the at least the portion of the medical device may be akin to the volume 904 of medical device 200 shown in the example of FIG. 4, in some embodiments. Although FIGS. 9A-9K graphically represent medical device 200, 300, 400 as a medical device in a bodily cavity, it should be noted that other types of medical devices may be utilized in other embodiments.

Figure 9A:
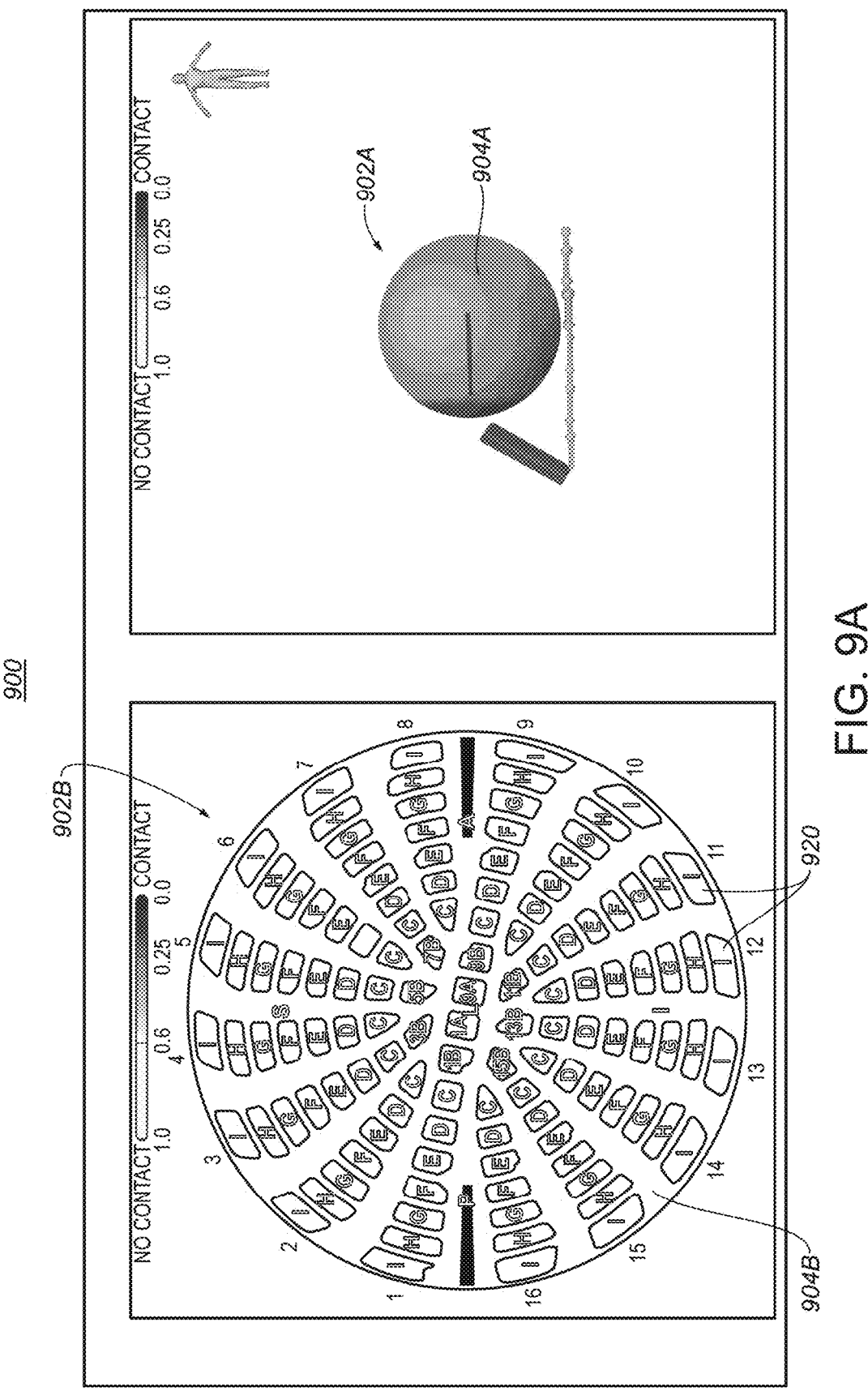

According to various embodiments, FIG. 9A corresponds to a first state in a mapping process (e.g., the mapping process including the progression depicted in the sequence of FIGS. 9A-9K as an example of instructions that may be associated with block 802*a*) in which a three-dimensional graphical representation of an envelope 906 (shown in various ones of FIGS. 9A-9K) is generated, the envelope representing at least a portion of an interior first volume of a bodily cavity (e.g., first volume 905 of heart 202 shown in the example of FIG. 4, in some embodiments). For example, according to some embodiments, block 802*a* may include computer-executable instructions provided by the program and configured to cause the data processing device system (e.g., 110, 310), via a display device system (e.g., display device system 332) and based on and throughout reception of at least a plurality of location signal sets (e.g., provided by a navigation system such as navigation system 260A, 260B), to progressively visually represent an evolution or enlarging of at least a portion of an envelope 906. The envelope 906 may represent at least some of an interior first volume (e.g., first volume 905) of the bodily cavity, but as the envelope 906 is enlarged by movement of the medical device throughout the bodily cavity, the envelope 906 may come to represent some or an entirety of the interior first volume of the bodily cavity. At least part of the sequence of FIGS. 9A-9K provides an example of a sequence of states of a graphical user interface including a particular graphical representation 900 that may be visually presented by the display device system 332 according to block 802*a*, such sequence visually representing the evolution and enlargement of at least a portion of the envelope 906 and movement of a medical device (such as medical device 200, 300, 400) within a region of space corresponding to the interior first volume (e.g., first volume 905 shown in the example of FIG. 4, in some embodiments) of the bodily cavity, according to some embodiments.

Figure 9B:
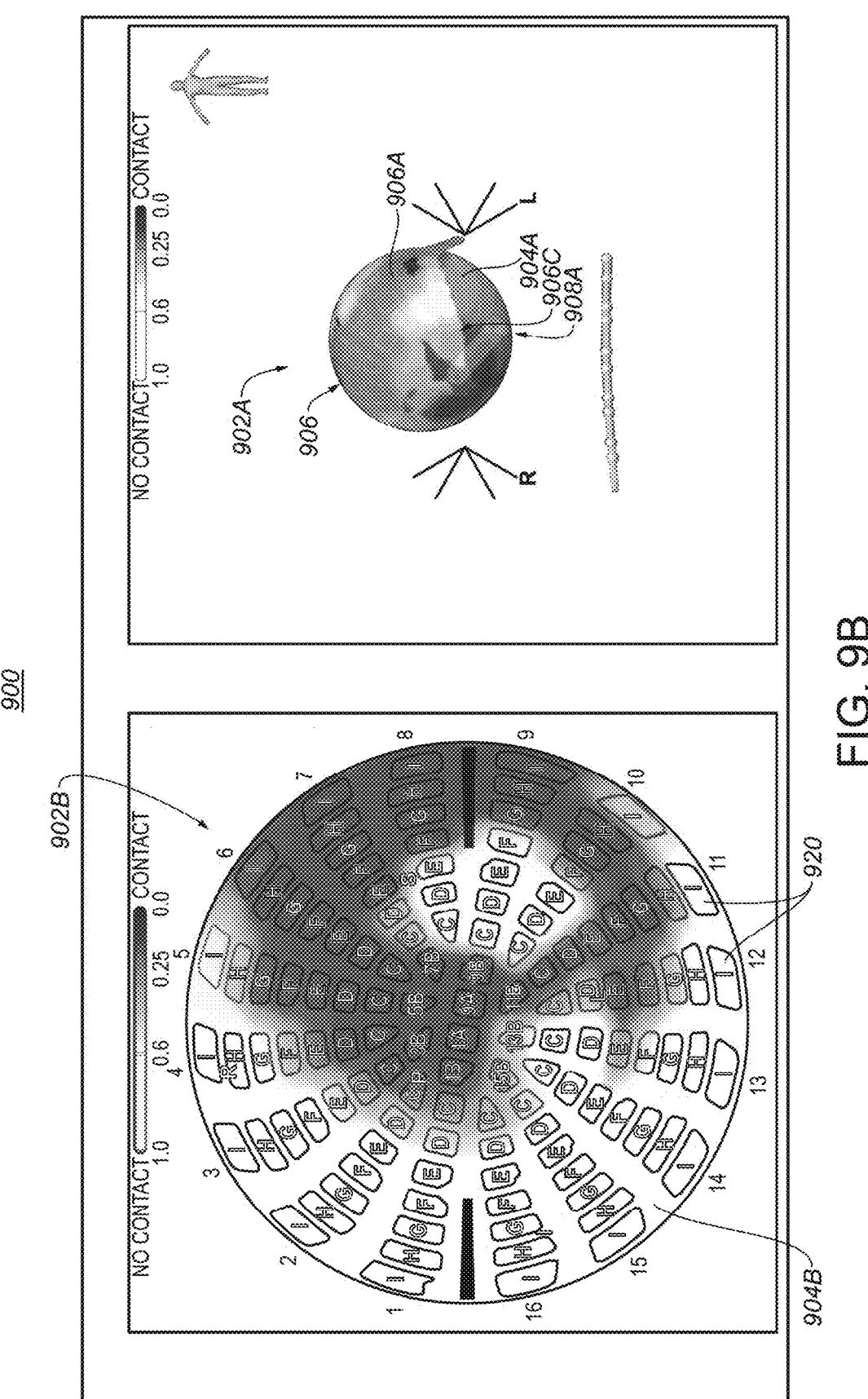
Figure 9C:
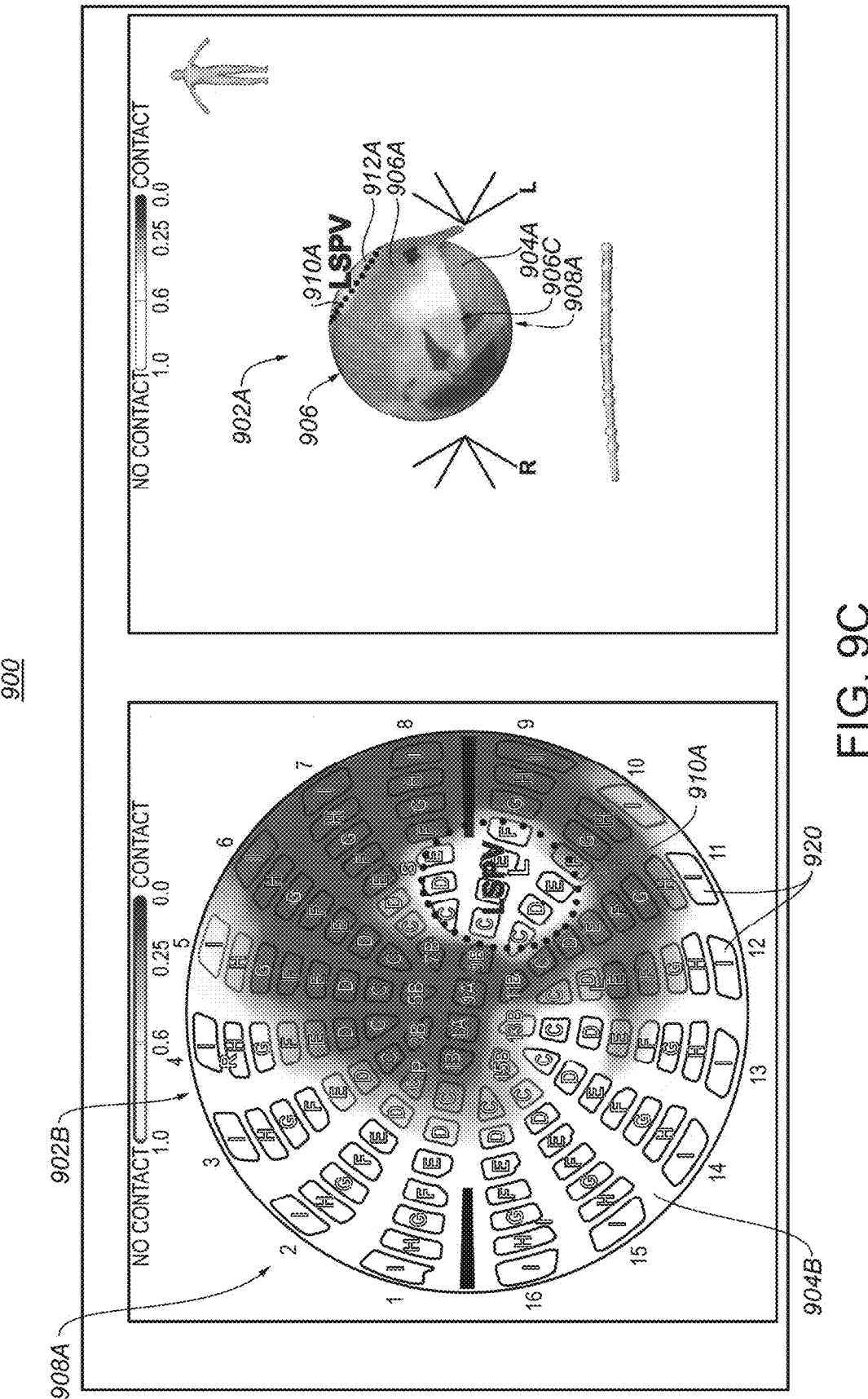
Figure 9D:
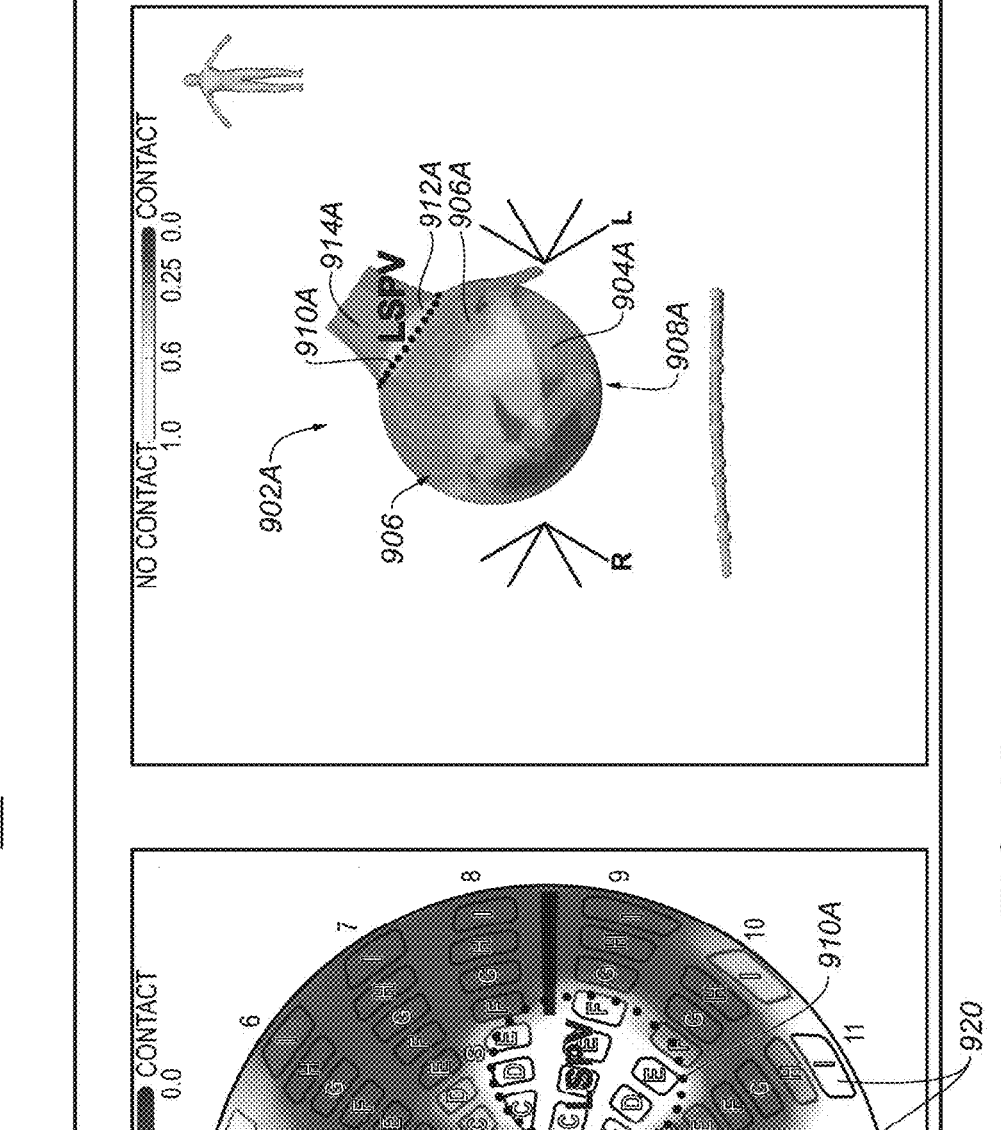

In this regard, FIGS. 9A and 9B represent part of a sequence of states of the particular graphical representation 900, e.g., according to block 802*a*, through which a visual representation of a portion 906A of the envelope 906 is generated, according to some embodiments, from a location signal set indicating a location in the bodily cavity to which the at least the portion of the medical device (e.g., corresponding to at least three-dimensional graphical representation 904A in FIG. 9B) has been moved (from the state of FIG. 9A) to engage a tissue surface in the bodily cavity (in the state of FIG. 9B). In FIG. 9B, the engagement of the transducers (e.g., transducers 220, 306, 406) with the tissue surface of the bodily cavity is represented by the varying levels of grayscale shading in portion 906C of the envelope 906. The state corresponding to FIG. 9B includes a representation of portion 906A as a first progressive enlargement of the envelope 906. The three-dimensional graphical representation of portion 906A as the first progressive enlargement of the envelope corresponds to a first location of at least a portion of the medical device 200, 300, or 400 in the sequence of locations (e.g., corresponding to the sequence of FIGS. 9A-9K) at which the at least the portion of the medical device, corresponding to at least graphical representation 904A, is sequentially located in the bodily cavity. FIGS. 9C and 9D represent the medical device in a same or a substantially same location as in the state of FIG. 9B. In the state corresponding to FIG. 9E, the visual representation of the portion of the envelope 906 includes a representation of portion 906B as a second progressive enlargement of the envelope 906, the representation of portion 906B as the second progressive enlargement of the envelope 906 corresponding to a second location of the at least the portion of the medical device in the sequence of locations. This sequential enlargement of the envelope 906 continues in at least FIGS. 9F-9I, according to an example of block 802*a* in some embodiments.

According to some embodiments, in a state in which the at least the portion of the medical device (e.g., medical device 200, 300, or 400) is at the first location in the sequence of locations (e.g., corresponding to FIGS. 9B, 9C, and 9D), the data processing device system 110, 310 receives (e.g., from a navigation system, such as navigation system 260A or 260B) three-dimensional location information of the at least the portion of the medical device. With such information, the data processing device system 110, 310 is configured, according to some embodiments, to at least plot a three-dimensional shell (e.g., which may represent at least a portion of the envelope 906) that has the shape of at least the portion of the medical device on the surface of the shell, resulting in visual representation of at least a portion of the envelope 906. In this regard, if a medical device like that shown in FIGS. 4 and 6 is used, the initial generation of the envelope or shell may likely have a spherical-like shape to match the shape of the medical device itself shown in FIGS. 4 and 6. Such is the case in the example of FIG. 9A to FIG. 9B.

Figure 9E:
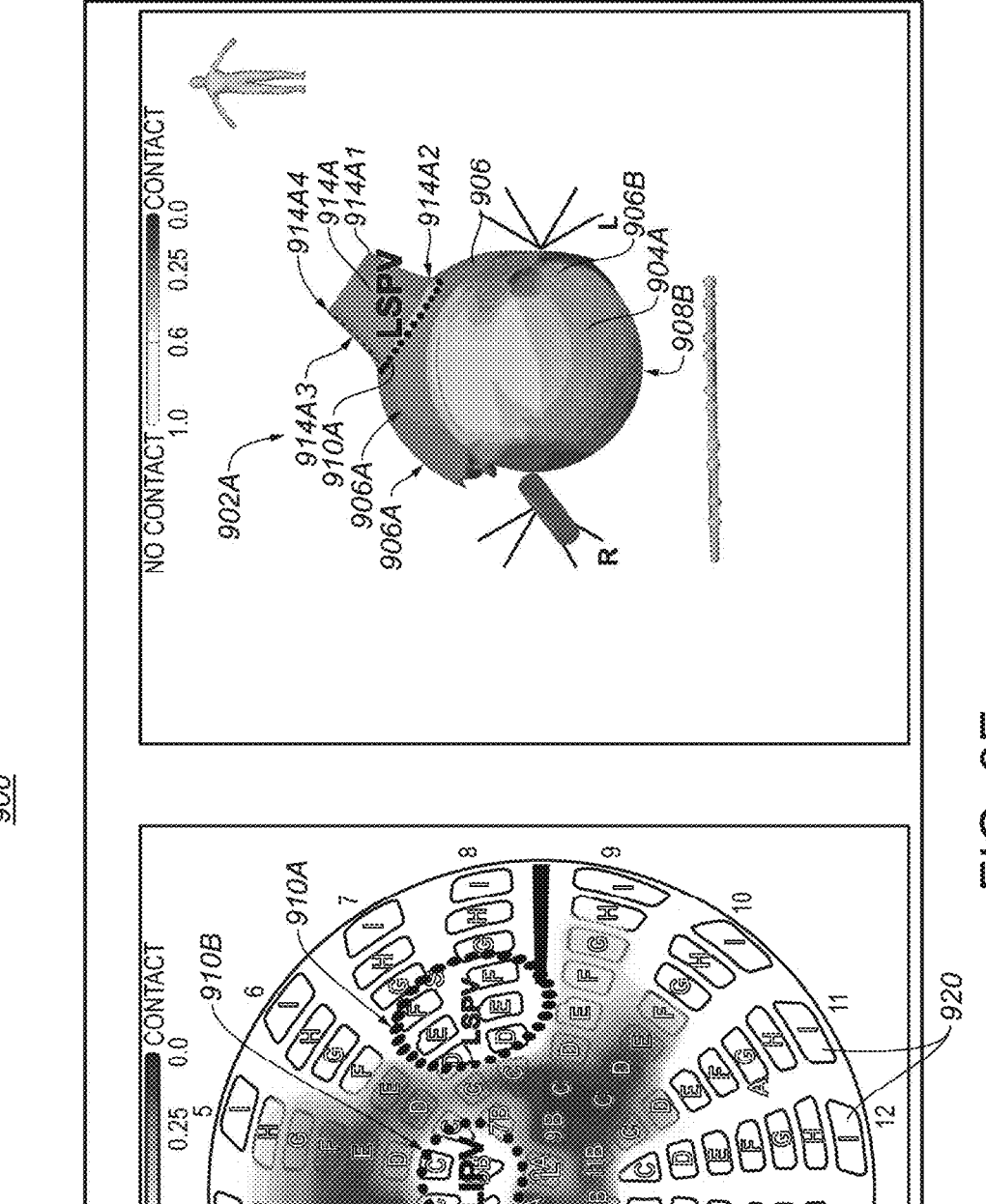

As the at least the portion of the medical device moves to the second location (e.g., corresponding to FIG. 9E) in the sequence of locations, the data processing device system 110, 310 receives (e.g., from a navigation system), additional three-dimensional location information of the at least the portion of the medical device. With such information, the data processing device system 110, 310 is configured, according to some embodiments, to plot a three-dimensional enlargement of the shell generated in association with the first location, the plotted enlargement forming an expansion region of the shell, resulting in a progressively enlarged visual representation of the at least a portion of the envelope. FIG. 9E shows an example of such an enlargement arising from a movement of a portion of the at least the portion of the medical device from a first location (e.g., corresponding to FIGS. 9B, 9C, and 9D) within a bodily cavity to a second location (e.g., corresponding to FIG. 9E) within the bodily cavity, according to some embodiments. The remnant, in FIG. 9E, of the shell or envelope 906 from the states of FIGS. 9B-9D is illustrated by representation of portion 906A in FIG. 9E, according to some embodiments. The resulting shape of the expanded envelope or shell, e.g., as shown in the example of FIG. 9E, may be determined or generated by the controller 324 including in the expanded envelope or shell only the outermost three-dimensional transducer locations from both the first location (e.g., corresponding to FIGS. 9B-9D) in the sequence of locations and the second location (e.g., corresponding to FIG. 9E) in the sequence of locations, according to some embodiments. Examples of how to generate a three-dimensional representation of a chamber based on recorded locations can be found in U.S. Patent Application Publication No. 2017/0330487 (Harlev et al.), published Nov. 16, 2017, which is hereby incorporated herein by reference.

The resulting shape of the expanded envelope or shell may be completed or smoothed by the controller 324 generating additional positions by interpolating between actual detected transducer positions, according to some embodiments. In some embodiments, interpolation may be utilized to improve stitching a newly expanded region of the envelope to a previously existing portion of the envelope, since the interpolation may provide estimates of stitching locations where actual measurement data may not exist.

It is noted that in some embodiments, the display of a graphical representation of a first volume within the bodily cavity as per block 802*a* need not be displayed as a progressively enlarging volume as described above with respect to envelope 906, and may be displayed as a volume retaining a same shape or substantially a same shape (e.g., as shown at least in two-dimensional portion 902B of the particular graphical representation 900 shown in FIGS. 9A-9K, according to some embodiments). Further in this regard, in some embodiments, a three-dimensional graphical representation of a first volume within the bodily cavity as per block 802*a* may retain a same or a substantially same shape, as may be the case, for example, if the first volume is represented from a pre-acquired image, such as, a computed tomography ("CT") scan or image or a magnetic resonance imaging ("MRI") scan or image. FIG. 9L illustrates an embodiment of three-dimensional portion 902A of particular graphical representation 900, where the envelope 906 representing first volume 905 is pre-generated based on a CT image 907 and, therefore, need not be produced by the envelope expansion process illustrated by FIGS. 9A-9K.

According to some embodiments, block 804 is associated with computer-executable instructions provided by the program and configured to cause the data processing device system (e.g., 110, 310) to cause, via the input-output device system (e.g., input-output device system 120, 320), the particular graphical representation (e.g., particular graphical representation 900) to be annotated to include a graphical annotation set. For example, according to some embodiments, block 804a is associated with computer-executable instructions provided by the program and configured to cause the data processing device system (e.g., 110, 310) to cause, via the input-output device system (e.g., input-output device system 120, 320), the three-dimensional graphical representation of the first volume (e.g., represented by envelope 906 and may be all or part of first volume 905) within the bodily cavity to be annotated to include a graphical annotation set. According to various embodiments, the three-dimensional graphical representation of the first volume within the bodily cavity is annotated per at least block 804a to include a graphical annotation set at least in a state in which at least a portion of a medical device (e.g., medical device 200, 300, 400) is located or simulated to be located within the bodily cavity. For example, in the state of FIG. 9C, the envelope 906 is annotated with a graphical annotation set 910A (e.g., a first annotation set), according to some embodiments.

The annotation set may take various forms according to various embodiments. In some embodiments associated with FIG. 9C, the graphical annotation set 910A includes a graphical dotted line and a graphical identifier "LSPV". It is noted that this particular annotation set is exemplary in nature and other embodiments may employ other forms and types of one or more annotations. According to some embodiments, at least a portion of the graphical annotation set included in the three-dimensional graphical representation of the first volume (e.g., represented by envelope 906 and may be all or part of first volume 905) within the bodily cavity graphically surrounds, in three-dimensional graphical space, a first particular region 912A of the three-dimensional graphical representation of the first volume within the bodily cavity. For example, in FIG. 9C, the dotted line of the graphical annotation set 910A surrounds a first particular region 912A of the three-dimensional graphical representation of the envelope 906. In some embodiments, at least a portion of the graphical annotation set included in the three-dimensional graphical representation of the first volume within the bodily cavity graphically surrounds, in three-dimensional graphical space, a first particular region 912A of the three-dimensional graphical representation of the first volume (e.g., represented by envelope 906 and may be all or part of first volume 905) within the bodily cavity that corresponds to a particular anatomical feature in the bodily cavity (e.g., a left superior pulmonary vein in the example of FIG. 9C, as described below in more detail in this disclosure).

In some embodiments, the graphical annotation set 910A is added to the particular graphical representation 900 to identify, highlight, enhance the visibility of, or otherwise call a user's attention to a first particular region 912A of the three-dimensional graphical representation of the first volume within the bodily cavity corresponding to a region within the bodily cavity that is to undergo a diagnostic or treatment procedure. In some embodiments, the graphical annotation set 910A is added to the particular graphical representation 900 prior to the commencement of the diagnostic or treatment procedure to the corresponding region within the bodily cavity. In some embodiments, the graphical annotation set 910A is added to the particular graphical representation 900 during the application of the diagnostic or treatment procedure to the corresponding region within the bodily cavity. In some embodiments, the graphical annotation set 910A is added to the particular graphical representation 900 after the completion of the diagnostic or treatment procedure to the corresponding region within the bodily cavity. In some embodiments, the graphical annotation set 910A is added to the particular graphical representation 900 to indicate a result of the diagnostic or treatment procedure. For example, in some embodiments associated with tissue ablation procedures, the graphical annotation set 910A may include lesion markers that may (a) indicate which particular regions within the bodily cavity were ablated, (b) a predicted, measured, or estimated quality value of the ablation process or resulting lesions, or both (a) and (b). In some embodiments, the lesion markers may be annotated to the particular graphical representation 900 either in response to a user-based input or a machine-based input. For instance, in the case of user-based input, a user may use an input device, such as a mouse or keyboard associated with input-output device system 120, 320, to identify where a lesion marker or other graphical annotation set should be placed in or on the graphical models of the medical device or bodily cavity. In the case of machine-based input, for example, location signal sets from, e.g., a catheter navigation system 260A, 260B may be analyzed by the data processing device system 110, 310 to determine the location(s) of one or more transducers 220, 306, 406 during or after conclusion of an ablation procedure performed by such transducer(s) in order to associate a lesion marker or other graphical annotation set with such location(s).

In some embodiments, the three-dimensional graphical representation of the first volume (e.g., represented by envelope 906 and may be all or part of first volume 905) within the bodily cavity is directly annotated to include the graphical annotation set. For example, the data processing device system 110, 310 may, in some embodiments, be configured by the program at least to receive, via the input-output device system (e.g., input-output device system 120, 320), user input defining at least part of the graphical annotation set, and cause, via the input-output device system, direct updating of the three-dimensional graphical representation of the first volume (e.g., represented by envelope 906 and may be all or part of first volume 905) within the bodily cavity to be annotated to include the graphical annotation set, at least in response to the received user input. This approach, however, can be challenging due at least in part to difficulties in viewing specific regions of the three-dimensional graphical representation of the first volume (e.g., represented by envelope 906 and may be all or part of first volume 905) within the bodily cavity in three-dimensional graphical space as well as difficulties in indicating graphical three-dimensional annotations (e.g., the dotted line of graphical annotation set 910A).

In some embodiments, the three-dimensional graphical representation of the first volume (e.g., represented by envelope 906 and may be all or part of first volume 905) within the bodily cavity is indirectly annotated to include the graphical annotation set. For example, in some embodiments, block 802b in FIG. 8A is associated with computer-executable instructions provided by the program and configured to cause the data processing device system (e.g., data processing device system 110, 310) to cause, via the input-output device system (e.g., input-output device system 120, 320), display of a two-dimensional graphical representation of at least part of a second volume within the bodily cavity. In some embodiments, the data processing device system may be configured by the program (e.g., per program instructions associated with block 804b) at least to cause, via the input-output device system, the two-dimensional graphical representation of the at least part of the second volume within the bodily cavity to be annotated to include the graphical annotation set. According to various embodiments, the two-dimensional graphical representation of the at least part of the second volume within the bodily cavity may be annotated per block 804b to include the graphical annotation set at least in a state in which the at least the portion of the medical device 200, 300, 400 is located at a first location (e.g., corresponding to graphical location 908A in at least FIGS. 9B-9D) within the bodily cavity. According to various embodiments, the graphical annotation set included in the two-dimensional graphical representation of the at least part of the second volume within the bodily cavity is displayed in a two-dimensional graphical manner. In some embodiments, the data processing device system 110, 310 may be configured by the program (e.g., per program instructions associated with block 804a) at least to cause, via the input-output device system 120, 320, the three-dimensional graphical representation of the first volume within the bodily cavity to be annotated to include the graphical annotation set at least in response to the data processing device system 110, 310 causing, per block 804b and via the input-output device system 120, 320, the two-dimensional graphical representation of the at least part of the second volume within the bodily cavity to be annotated to include the graphical annotation set. According to various embodiments, the graphical annotation set included in the three-dimensional graphical representation of the first volume within the bodily cavity is displayed in a three-dimensional manner.

At least some of such embodiments may be exemplified in FIG. 9 in which a second portion 902B of the particular graphical representation 900 includes a two-dimensional graphical representation 904B of at least a part of a second volume within the bodily cavity, the two-dimensional graphical representation 904B of the at least part of the second volume within the bodily cavity displayed in a two-dimensional graphical manner. According to various embodiments, the at least part of the second volume includes a three-dimensional outer or exterior portion of the second volume within the bodily cavity. Accordingly, in some embodiments, the two-dimensional graphical representation 904B graphically displays the three-dimensional outer or exterior portion of the second volume within the bodily cavity in a two-dimensional manner. According to various embodiments, the second volume within the bodily cavity corresponds to at least part of a volume occupied by the at least the portion of the medical device 200, 300, 400, as, for example, indicated by the transducer graphical elements 920 in at least FIG. 9A (two called out), which may correspond to transducers 220, 306, 406 in some embodiments. For instance, in some embodiments, such second volume may be akin to second volume 904 occupied by medical device 200 illustrated in FIG. 4. In various embodiments, the two-dimensional graphical representation (e.g., two-dimensional graphical representation 904B) of the at least part of the second volume within the bodily cavity corresponds to the three-dimensional graphical representation (e.g., three-dimensional graphical representation 904A) of the second volume. In some embodiments, the second volume within the bodily cavity forms some, but not all, of the first volume within the bodily cavity. For example, in embodiments in which the second volume within the bodily cavity corresponds to a volume (such as volume 904 in the example of FIG. 4) occupied by the at least a portion of a particular medical device located within a bodily cavity having a first volume (such as volume 905 of heart 202 in the example of FIG. 5), the volume of the at least the portion of the particular medical device is typically smaller than the first volume of the bodily cavity. Various two-dimensional graphical representations of the at least part of the second volume are possible in various embodiments. For instance, in some embodiments, the two-dimensional graphical representation of the at least part of the second volume within the bodily cavity maps three-dimensional surface portions of the at least the portion of the medical device onto a two-dimensional coordinate frame. For example, in some embodiments associated with FIGS. 9, the surface portions of the at least the portion of the medical device 200, 300, 400, may include surface portions (e.g., electrodes 315, 415) of various transducers 306,406 provided by the at least the portion of the medical device. In FIGS. 9, transducer graphical elements 920 representative of the transducers are arranged graphically in a two-dimensional distribution in the second portion 902B of the particular graphical representation 900. In this regard, in some embodiments in which the at least the portion of the medical device 200, 300, 400 includes a plurality of transducers, the two-dimensional graphical representation of the at least the portion of the second volume within the bodily cavity may map information indicating a three-dimensional spatial distribution of the plurality of transducers projected onto a two-dimensional coordinate frame. In some embodiments, a plurality of transducer graphical elements (e.g., 920) may be arranged in the particular graphical representation 900 in a particular spatial distribution representing the three-dimensional distribution of transducers (e.g., 220, 306, 406) of the at least the portion of the medical device distorted onto a two-dimensional plane to form the two-dimensional graphical representation. In this regard, in some embodiments, the two-dimensional graphical representation 904B of the three-dimensional distribution of transducers (e.g., 220 or 306) distorted onto a two-dimensional plane is not merely an isometric or other perspective view of the three-dimensional distribution of transducers, because such an isometric or other perspective view may be considered a three-dimensional graphical representation. Accordingly, in some embodiments, the two-dimensional graphical representation 904B may represent a map including spatial distortion caused by mapping, e.g., a curved three-dimensional surface onto a flat two-dimensional surface. In the example of at least FIG. 9A, such distortion is viewable by the distorted electrode sizes of some of the electrode graphical elements 920 along the outer edge of the two-dimensional graphical representation 904B. Three-dimensional graphical representation 904A may be of a volume corresponding to or representing a volume occupied by the at least a portion of the medical device 200, 300, 400. In some embodiments, such volume may be akin to volume 904 occupied by medical device 200 illustrated in FIG. 4.

The two-dimensional graphical representation 904B may be generated according to the display instructions associated with block 802b, in some embodiments, according to a conformal map or projection, such as a Mercator map or projection, a transverse Mercator map or projection (also known as Cassini projection), or other three-dimensional-to-two-dimensional mapping or projection, known in the art, according to some embodiments. See, e.g., U.S. Pat. No. 10,368,936, issued Aug. 6, 2019 (Brewster et al.) in relation to various mapping techniques. According to various embodiments, a conformal mapping is a function that preserves local angles. For example, according to some embodiments, when a particular spatial relationship between the plurality of transducers 220, 306, 406 is conformally mapped to the particular graphical representation 900, an angle defined between a group of transducers (e.g., 220, 306) according to the particular spatial relationship is preserved between the corresponding group of transducer graphical elements 920. In FIGS. 9, the transducer graphical elements 920 are mapped in a two-dimensional projection that approximates a Lambert Azimuthal projection. In this two-dimensional projection the transducer graphical elements 920 representing all of the transducers 306, 406 radiate at least in part along a radial line from a center of the projection. According to various embodiments associated with FIGS. 9, transducers 220, 306 are distributed over each of two hemispherical regions provided by the at least the portion of the medical device and the transducer graphical elements 920 representing all of the transducers 220, 306 are graphically depicted in a two-dimensional distribution in which all the transducer graphical elements 920 are radially distributed from a particular region in the two-dimensional distribution that corresponds to a pole of one of the two hemispherical regions. In some embodiments, the two-dimensional graphical representation need not be a projection or mapping from a three-dimensional model, and may merely be any two-dimensional graphical representation, e.g., including an arrangement of transducers.

According to some embodiments, various features that are mapped onto the two-dimensional graphical representation may have a distorted appearance (for example, at least some of the transducer graphical elements 920). In this regard, in some embodiments, annotations that are mapped or projected onto the two-dimensional graphical representation from three-dimensional space may have a distorted appearance. In some embodiments, the two-dimensional graphical representation 904B of the at least part of the second volume within the bodily cavity may, in some embodiments, map three-dimensional tissue surface portions corresponding to or associated with the at least part of the second volume within the bodily cavity onto a two-dimensional coordinate frame. Such may be the case, in some embodiments, when the second volume represents a volume of the medical device, like volume 904 in the example of FIG. 4, and the medical device is in contact with a tissue surface portion, and the two-dimensional graphical representation 904B maps results of such tissue contact. In some embodiments, the second volume may be a volume enclosed or surrounded by a three-dimensional tissue surface (e.g., the first volume) and the two-dimensional graphical representation of the at least part of the second volume within the bodily cavity may map three-dimensional tissue surface portions enclosing or surrounding the second volume within the bodily cavity onto a two-dimensional coordinate frame in a manner similar to that described by Raymond E. Ideker, M.D., Ph.D., et al. in the document "A Computerized Method for the Rapid Display of Ventricular Activation During the Intraoperative Study of Arrhythmias", in the journal Circulation, vol. 59, No. 3, pages 449-458 (Mar. 1, 1979). In this document, Ideker et al. disclose various two-dimensional surface maps in which a total heart surface is depicted two-dimensionally as if the ventricles were folded out after an imaginary cut was made from the crux to the apex. In some particular embodiments in which the at least the portion of the medical device (e.g., medical device 200, 300, 400) includes a plurality of transducers (e.g., transducers 220, 306, 406), the two-dimensional graphical representation (e.g., two-dimensional graphical representation 904B) of the at least part of the second volume within the bodily cavity maps information indicating a three-dimensional spatial distribution of transducer-to-tissue contact information onto a two-dimensional coordinate frame. In at least some particular embodiments in which the at least the portion of the medical device (e.g., medical device 200, 300, 400) includes a plurality of transducers (e.g., transducers 220, 306, 406), the two-dimensional graphical representation (e.g., two-dimensional graphical representation 904B) of the at least part of the second volume within the bodily cavity maps information indicating a three-dimensional spatial distribution of the plurality of transducers onto a two-dimensional coordinate frame.

According to various embodiments, in FIGS. 9B, 9C, and 9D (among others of FIG. 9), the two-dimensional graphical representation 904B of the second volume within the bodily cavity includes such a spatial distribution of transducers and degree of transducer-to-tissue contact information presented in a grayscale manner with darker regions indicating relatively greater degrees of transducer-to-tissue contact (e.g., electrode-to-tissue contact). FIGS. 9B, 9C, and 9D correspond to a state in which the at least the portion of the medical device 200, 300, 400 is located at a first location within the bodily cavity. In FIGS. 9B, 9C, and 9D, the graphically depicted three-dimensional graphical representation 904A of a volume corresponding to or representing the volume occupied by the at least the portion of the medical device 200, 300, 400 is graphically depicted three-dimensionally at a location 908A in the portion 902A of the particular graphical representation 900, the location 908A corresponding to the first location within the bodily cavity. In some embodiments, the location 908A may be determined from a location signal set provided by a navigation system (e.g., 260A, 260B). According to various embodiments, at least some parts of the at least the portion of the medical device (e.g., medical device, 200, 300, 400) are in contact with a tissue surface in the bodily cavity at least in a state in which the at least the portion of the medical device is located at the first location within the bodily cavity. This tissue contact may be determined in various manners including those described in this disclosure. According to various embodiments, the graphically displayed transducer-to-tissue contact information may include interpolated values derived from the transducer-to-tissue contact information sampled by multiple ones of the transducers. It is noted that portions of the graphically displayed transducer-to-tissue contact information are associated with the presence of respective portions of the tissue surface in the bodily cavity, and as such, may be considered a map of the tissue surface portions.

FIG. 9C shows, according to some embodiments, the annotation of the two-dimensional graphical representation 904B of the at least part of the second volume (e.g., which may be akin to second volume 904 illustrated in the example of FIG. 4, in some embodiments) within the bodily cavity per block 804b in FIG. 8A. Such annotation causes the two-dimensional graphical representation 904B to include the graphical annotation set 910A. As described above, in some embodiments, the three-dimensional graphical representation of the first volume (e.g., represented by envelope 906 and which, for example, may be akin to first volume 905 illustrated in the example of FIG. 4, in some embodiments) within the bodily cavity is annotated per block 804*a* in FIG. 8A to include the graphical annotation set 910A at least in response to the data processing device system 110, 310 causing, per block 804*b* in FIG. 8A and via the input-output device system 120, 320, the two-dimensional graphical representation 904B of the at least part of the second volume within the bodily cavity to be annotated to include the graphical annotation set 910A. In this regard, in some embodiments, the two-dimensional graphical representation 904B may first be annotated per block 804*b* in FIG. 8A to produce the graphical annotation set 910A in such two-dimensional graphical representation 904B, and such annotation of the two-dimensional graphical representation 904B may cause (e.g., automatically cause by way of a resulting machine-based annotation, in some embodiments) the three-dimensional graphical representation 904A to be correspondingly annotated with graphical annotation set 910A. For instance, in some embodiments, such a configuration may allow a user to cause (e.g., via user input) an annotation of the two-dimensional graphical representation 904B, and then, the three-dimensional graphical representation 904A may automatically be correspondingly annotated to allow both graphical representations 904A, 904B to be annotated by a single user annotation action. Of course, in other embodiments, the three-dimensional graphical representation 904A may be annotated first to cause a corresponding machine or automatic annotation of the two-dimensional graphical representation 904B, and, in some embodiments, user input is not needed to perform any annotation.

In some contexts, the case of initially annotating the two-dimensional graphical representation 904B may be preferable at least because the annotation of the two-dimensional graphical representation 904B of the at least part of the second volume within the bodily cavity may be relatively easier to perform (as compared to annotating the three-dimensional graphical representation 904A), since the entirety or the majority of the outer or exterior portion of the second volume may be graphically displayed at one time by the two-dimensional graphical representation 904B. Unlike a three-dimensional graphical representation that may be unable, due to potential viewing perspective limitations, to concurrently display all of its modeled three-dimensional space, a two-dimensional graphical representation like representation 904B that displays its entire modeled space may facilitate the ability to select any particular portion of the modeled space at any time. Of course, in some embodiments, multiple three-dimensional models may be graphically displayed so that a user can view all of the modeled three-dimensional space at a time to provide a similar benefit.

Per the above discussion, a machine-based or automatic annotation of the three-dimensional graphical representation of a volume, such as the first volume that may be graphically represented by envelope portion 906A or the second volume that may be graphically represented by three-dimensional graphical representation 904A, in response to annotation of a two-dimensional graphical representation (e.g., two-dimensional graphical representation 904B) of at least part of a volume (e.g., the second volume) within the bodily cavity may be relatively easier to accomplish in some embodiments than if the three-dimensional graphical representation was to be directly manually annotated (e.g., via received user input). On the other hand, according to some embodiments, annotation of a graphically depicted three-dimensional graphical representation of a volume does not occur in response to annotation of a two-dimensional graphical representation of a volume. For instance, in some embodiments, annotation of a graphically depicted three-dimensional graphical representation (e.g., three-dimensional graphical representation 904A) of a volume corresponding to or representing the volume occupied by the at least the portion of the medical device 200, 300, 400 does not occur in response to annotation of the two-dimensional graphical representation (e.g., two-dimensional graphical representation 904B) of the at least part of the second volume within the bodily cavity.

For example, in the state of FIG. 9E, which corresponds to a movement of the at least the portion of the medical device 200, 300, 400 away from the first location within the bodily cavity, the graphically depicted three-dimensional graphical representation 904A of a second volume corresponding to or representing the volume occupied by the at least the portion of the medical device 200, 300, 400 appears in a manner indicating that it is not annotated by the graphical annotation set 910A, although the two-dimensional graphical representation 904B of the second volume is annotated with graphical annotation set 910A, according to various embodiments. However, in the state of FIG. 9E, the three-dimensional graphical representation of the first volume (e.g., graphically represented by envelope portion 906A in the state of FIG. 9C) is annotated with the graphical annotation set 910A in a manner corresponding to the annotation of the two-dimensional graphical representation 904B of the second volume with graphical annotation set 910A. In this regard, in some embodiments, the annotation of a two-dimensional graphical representation of at least part of a volume (e.g., the second volume) within the bodily cavity may lead to, cause, or result in no corresponding annotation of any three-dimensional graphical representation of the volume (or any volume), or may lead to, cause, or result in a corresponding annotation of a three-dimensional graphical representation of another volume (e.g., the first volume).

In some embodiments, the two-dimensional graphical representation 904B of the at least part of the second volume within the bodily cavity is annotated to include the graphical annotation set 910A at least in a state in which the at least the portion of the medical device 200, 300, 400 is located at the first location within the bodily cavity. In some embodiments, the three-dimensional graphical representation of the first volume (e.g., represented by envelope 906 and may be all or part of first volume 905) within the bodily cavity is annotated to include the graphical annotation set 910A in a state in which the at least the portion of the medical device 200, 300 is located at the first location within the bodily cavity. In this regard, the annotation of the three-dimensional graphical representation of the first volume (e.g., represented by envelope 906 and may be all or part of first volume 905) within the bodily cavity may occur very shortly after (e.g., instantaneous and merely restricted by computer processing time) the annotation of the two-dimensional graphical representation 904B of the at least part of the second volume.

In some embodiments, the data processing device system (e.g., data processing device system 110, 310) may be configured by the program (e.g., via program instructions associated with some embodiments of block 804) at least to receive, via the input-output device system (e.g., input-output device system 120, 320), user input defining at least part of the graphical annotation set, and cause, via the input-output device system, updating of the two-dimensional graphical representation (e.g., two-dimensional graphical representation 904B) of the at least part of the second volume within the bodily cavity to be annotated to include the graphical annotation set (e.g., graphical annotation set 910A), at least in response to the received user input. For example, the dotted line of the graphical annotation set 910A may, in some embodiments, be accomplished at least in part by execution of such instructions by the data processing device system in response to various user instructions, inputs, or actions. For instance, in some embodiments, a user instruction, input or action may originate from a user clicking a mouse button over a particular region or regions of the two-dimensional graphical representation 904B of the at least part of the second volume within the bodily cavity. In this case, various instructions may configure the data processing device system to recognize this user instruction when it is received via an input-output device system (e.g., 120, 320) as a user instruction to form or define at least a portion of the graphical path (e.g., by dragging a cursor around a path to define the dotted line or other graphical annotation element). Alternatively, a user instruction, input or action may originate from a user clicking a mouse button over a selection menu to select a particular annotation that is to be applied to the two-dimensional graphical representation 904B of the at least part of the second volume within the bodily cavity. In some embodiments, the definition of the graphical annotation set need not be defined according to user input and, in some embodiments, may be automatically defined.

In various embodiments, the graphical annotation set (e.g., graphical annotation set 910A) may be annotated to (a) the two-dimensional graphical representation 904B of the at least part of the second volume (e.g., which may be akin to second volume 904 in the example of FIG. 4) within the bodily cavity, (b) the three-dimensional graphical representation of the first volume (e.g., which may be akin to first volume 905, or in some embodiments, also second volume 904, in the example of FIG. 4 and may be represented by envelope 906 and may be all or part of first volume 905) within the bodily cavity, or to each of (a) and (b) to indicate, identify, highlight, enhance the visibility of, or otherwise call a user's attention to a location of a portion of the medical device, a location in a patient or bodily cavity within a patient (such as a location of an anatomical feature), or a relative positioning between a portion of the medical device and the location within the patient, in various embodiments. For example, in FIG. 9C, the displayed two-dimensional graphical representation 904B of the at least part of the second volume within the bodily cavity and the three-dimensional graphical representation of the first volume within the bodily cavity correspond to a positioning of the at least the portion of the medical device 200, 300, 400 at a first location in the bodily cavity (graphically represented in the portion 902A of the particular graphical representation 900 by location 908A), the first location in the bodily cavity associated with a state in which at least a portion of the medical device contacts a tissue surface in the bodily cavity. In this regard, for example, at least in some embodiments where the two-dimensional graphical representation and the three-dimensional graphical representation correspond to a same first location in the bodily cavity (e.g., in which the medical device contacts tissue), the graphical annotation set (e.g., graphical annotation set 910A) may be concurrently annotated to both the two-dimensional graphical representation and the three-dimensional graphical representation. According to various embodiments, the graphically displayed transducer-to-tissue contact information in the displayed two-dimensional graphical representation 904B (in various states through FIGS. 9A-9K) of the at least part of the second volume within the bodily cavity includes shaded regions surrounding a non-shaded region in FIG. 9C. This surrounded non-shaded region in FIG. 9C indicates no transducer-to-tissue contact since it overlies the port of a pulmonary vein of a cardiac cavity. According to various embodiments, the dotted line provided by the graphical annotation set 910A is configured to visually indicate that this region corresponds to a particular anatomical feature (e.g., a pulmonary vein in this example embodiment). The identifier "LSPV" provided by the graphical annotation set 910A indicates that the identified pulmonary vein is the left superior pulmonary vein of the cardiac cavity.

Referring back to the method 800A of FIG. 8A, block 806 is associated, according to some embodiments, with computer-executable instructions provided by the program, and configured to cause the data processing device system (e.g., 110, 310) to cause, via the input-output device system 120, 320, the three-dimensional graphical representation of the first volume (e.g., represented by envelope 906 and may be all or part of first volume 905) within the bodily cavity to add an anatomical feature graphical representation extending away from a first particular region (e.g., first particular region 912A) of the three-dimensional graphical representation of the first volume within the bodily cavity. In some embodiments, the actions of block 806 occur at least in response to the three-dimensional graphical representation of the first volume within the bodily cavity being annotated to include the graphical annotation set 910A (e.g., as per block 804*a*), and occur at least in a state in which the at least the portion of the medical device (e.g., medical device 200, 300, 400) is located within the bodily cavity. According to various embodiments, the added anatomical feature graphical representation extends away from the first particular region (e.g., first particular region 912A) of the three-dimensional graphical representation of the first volume within the bodily cavity. For example, in FIG. 9D, an anatomical feature graphical representation 914A has been generated as per some embodiments of block 806. In this regard, the added anatomical feature graphical representation 914A is shown extending away from the first particular region 912A of the three-dimensional graphical representation of the first volume within the bodily cavity. According to various embodiments, the added anatomical feature graphical representation 914A graphically extends away from the first particular region 912A of the three-dimensional graphical representation of the first volume within the bodily cavity in a direction extending outwardly from the three-dimensional graphical representation of the first volume within the bodily cavity.

According to various embodiments, the anatomical feature graphical representation 914A extending away from the first particular region 912A of the three-dimensional graphical representation of the first volume (e.g., represented by envelope 906 and may be all or part of first volume 905) within the bodily cavity is added to the three-dimensional graphical representation of the first volume within the bodily cavity at least in a state in which the at least the portion of the medical device (e.g., medical device 200, 300, 400) is located at a particular location within the bodily cavity. For example, FIG. 9D indicates that the anatomical feature graphical representation 914A has been added to the three-dimensional graphical representation of the first volume within the bodily cavity when the graphically depicted volume (e.g., graphically depicted at least by three-dimensional graphical representation 904A in some embodiments) corresponding to the at least the portion of the medical device is located graphically at location 908A which may correspond to such particular location.

According to some embodiments, the data processing device system (e.g., data processing device system 110, 310) is configured by the program at least to cause, via the input-output device system (e.g., input-output device system 120, 320), display of a three-dimensional graphical representation 904A of a volume corresponding to a volume of the portion of the medical device graphically depicted as located at least in part within the three-dimensional graphical representation of the first volume (e.g., represented by envelope 906 and may be all or part of first volume 905) within the bodily cavity (for example, as shown in FIG. 9D). According to some embodiments, the data processing device system (e.g., data processing device system 110, 310) is configured by the program at least to cause, via the input-output device system (e.g., input-output device system 120, 320), display of a three-dimensional graphical representation 904A of a volume corresponding to a volume of the portion of the medical device graphically depicted as located at least in part within the three-dimensional graphical representation of the first volume (e.g., represented by envelope 906 and may be all or part of first volume 905) within the bodily cavity (for example, as shown in FIG. 9D). According to various embodiments, a first relative graphical positioning between the three-dimensional graphical representation 904A of the volume corresponding to the volume of the portion of the medical device and the three-dimensional graphical representation of the first volume within the bodily cavity corresponds to a second relative positioning between the at least the portion of the medical device (e.g., medical device 200, 300, 400) and the bodily cavity at least in a state in which the at least the portion of the medical device is located at the particular location within the bodily cavity (for example, as described above). According to some embodiments, the added anatomical feature graphical representation 914A extends away from the first particular region (e.g., first particular region 912A) of the three-dimensional graphical representation of the first volume within the bodily cavity in a direction away from the three-dimensional graphical representation 904A of the volume corresponding to the volume of the portion of the medical device in a state in which the first relative graphical positioning exists between the three-dimensional graphical representation 904A of the volume corresponding to the volume of the portion of the medical device and the three-dimensional graphical representation of the first volume within the bodily cavity. In some embodiments, the state in which the first relative graphical positioning exists between the three-dimensional graphical representation 904A of the volume corresponding to the volume of the portion of the medical device and the three-dimensional graphical representation of the first volume within the bodily cavity is associated with contact between at least a part of the portion of the medical device (e.g., medical device 200, 300, 400) and a tissue surface within the bodily cavity.

Employing three-dimensional graphical representation 904A of the volume corresponding to the volume of the portion of the medical device to help define a desired extension direction for the added anatomical feature graphical representation 914A may be beneficial when only a relatively small portion (e.g., portion 906A) of the three-dimensional graphical representation of the first volume within the bodily cavity has been defined, the relatively small portion making it difficult to define a direction inwardly or outwardly from the first particular region 912A. The three-dimensional graphical representation 904A of the volume corresponding to the volume of the portion of the medical device is more fully defined to provide a better indication of how the desired extension direction should be oriented, especially in the presence of tissue contact. In this regard, according to some embodiments, the anatomical feature graphical representation 914A is added to the three-dimensional graphical representation of the first volume within the bodily cavity in a state in which the at least the portion of the medical device 200, 300, 400 is located at the first location (e.g., corresponding to graphical location 908A) within the bodily cavity.

It is noted that, in some embodiments, the three-dimensional graphical representation of the first volume (e.g., represented by envelope 906 and may be all or part of first volume 905) within the bodily cavity is annotated to include the graphical annotation set 910A in the state in which the first relative graphical positioning exists (e.g., in the state of FIG. 9D) between the three-dimensional graphical representation 904A of the volume corresponding to the volume of the portion of the medical device and the three-dimensional graphical representation of the first volume within the bodily cavity.

The addition of the anatomical feature graphical representation 914A to the three-dimensional graphical representation of the first volume (e.g., represented by envelope 906 and may be all or part of first volume 905) within the bodily cavity may be motivated for different reasons. In some embodiments, the anatomical feature graphical representation is added at least to highlight, enhance the visibility of, or otherwise call a user's attention to a location of the anatomical feature or a relative positioning between a portion of the medical device and a location of the anatomical feature. For example, in some embodiments, the anatomical feature graphical representation 914A corresponds to an anatomical feature in the bodily cavity that is difficult to represent by the process that is used to define the three-dimensional graphical representation of the first volume within the bodily cavity. For instance, in some embodiments, the bodily cavity is a cardiac cavity, and the added anatomical feature graphical representation 914A corresponds to a pulmonary vein. In particular embodiments in which a navigation system is used to help define the three-dimensional graphical representation of the first volume, the at least the portion of the medical device may be too large, or otherwise ill-suited to map relatively small features such as a pulmonary vein. The addition of the anatomical feature graphical representation 914A in accordance with various embodiments may be employed at least to highlight, enhance the visibility of, or otherwise call a user's attention to the corresponding anatomical feature or a relative positioning between a portion of the medical device and the location of the anatomical feature.

In FIG. 9E, according to some embodiments, the added anatomical feature graphical representation 914A is displayed in a three-dimensional manner. In FIG. 9E, according to some embodiments, the added anatomical feature graphical representation 914A includes a graphical representation (e.g., a three-dimensional graphical representation) of a shape. According to various embodiments, the shape includes an outer side surface 914A3 between a first end region 914A1 of the shape and a second end region 914A2 of the shape opposing the first end region 914A1 of the shape. According to some embodiments, the outer side surface 914A3 of the shape is curved along a geodesic 914A4 of the outer side surface 914A3 spanning from the first end region 914A1 to the second end region 914A2. It is noted that geodesic 914A4 is represented as a dashed line for the purposes of illustration. According to various embodiments, the outer side surface 914A3 of the shape is curved inwardly along the geodesic 914A4 toward an interior or innermost portion of the shape. Various shapes whose outer side surfaces 914A3 are curved inwardly along a geodesic 914A4 may be employed according to various embodiments. For example, in some embodiments, the added anatomical feature graphical representation 914A includes a graphically represented pseudosphere shaped portion.

Added anatomical feature graphical representations having other forms of shapes may be employed in other embodiments. For example, in some embodiments, the added anatomical feature graphical representation includes a graphically represented cylindrical portion. In some embodiments, the added anatomical feature graphical representation includes a graphically represented conical frustum shaped portion. It is noted that some of the shapes described above, as well as others, need not be bodies of revolution, and in this regard, (a) the first end region 914A1, (b) the second end region 914A2, or each of (a) and (b) may have a non-circular shape, according to various embodiments. According to some embodiments, the first end region 914A1 has a shape defined by at least part of the graphical annotation set 910A. For example, in some embodiments, a shape of the first end region 914A1 may be defined by a region enclosed or surrounded by the dotted line.

According to some embodiments, the data processing device system (e.g., data processing device system 110, 310) is configured by the program (e.g., per some embodiments of block 802a) at least to cause, via the input-output device system (e.g., input-output device system 120, 320), display of a three-dimensional graphical representation 904A of a volume corresponding to a volume of the portion of the medical device graphically depicted as located at least in part within the three-dimensional graphical representation of the first volume (e.g., represented by envelope 906 and may be all or part of first volume 905) within the bodily cavity. In some embodiments, the data processing device system is configured by the program (e.g., per some embodiments of block 802a) at least to cause, via the input-output device system and in response to a change in a relative positioning between the at least the portion of the medical device (e.g., medical device 200, 300, 400) with respect to or within the bodily cavity, varying of a relative graphical positioning between the three-dimensional graphical representation 904A of the volume corresponding to the volume of the portion of the medical device and the three-dimensional graphical representation of the first volume within the bodily cavity. For example, according to some embodiments, FIG. 9E (i.e., as compared with FIG. 9D) shows the three-dimensional graphical representation 904A of a volume corresponding to a volume of the portion of the medical device graphically depicted as located at second graphical location 908B corresponding to second location in the bodily cavity spaced from the first location. In this regard, the change from the state of FIG. 9D to the state of FIG. 9E illustrates a varying of a relative graphical positioning between the three-dimensional graphical representation 904A of the volume corresponding to the volume of the portion of the medical device and the three-dimensional graphical representation of the first volume (e.g., represented by different states of the envelope 906 in FIG. 9D (with at least portion 906A) and FIG. 9E (with at least portions 906A, 906B) within the bodily cavity. Such varying occurs in response to a corresponding change in a relative positioning between the at least the portion of the medical device with respect to or within the bodily cavity, in some embodiments. A representation of portion 906B (which may be referred to as a representation of a second portion) of the envelope 906 has been formed in a manner similar to, or the same as that described above with respect to portion 906A.

Figure 9F:
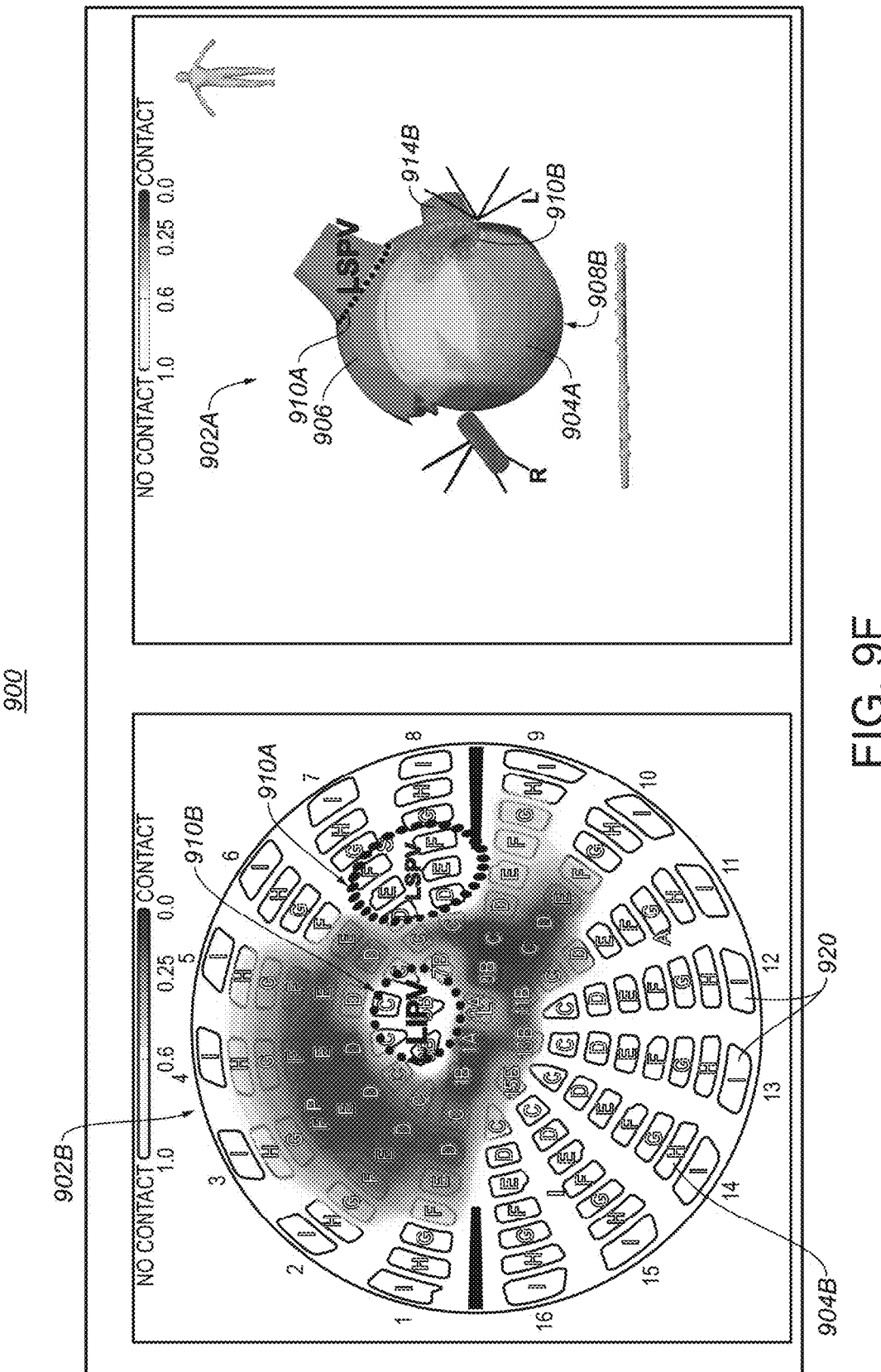

In FIG. 9F, a second anatomical feature graphical representation 914B has been added (e.g., as per some embodiments of method 800A, block 806) after the three-dimensional graphical representation 904A of a volume corresponding to a volume of the portion of the medical device is graphically depicted as located at second graphical location 908B. It is noted, however, that the addition of any anatomical feature graphical representation (e.g., 914A, 914B) in other methods described in this disclosure need not occur in at least some embodiments of such other methods, such as method 800B described below with respect to FIG. 8B.

FIG. 8B shows a respective data generation and flow diagram, which may implement various embodiments of method 800B by way of associated computer-executable instructions provided by a program, according to some example embodiments. According to some embodiments, block 822 is associated with computer-executable instructions configured to cause the data processing device system (e.g., 110, 310) to cause, via the input-output device system (e.g., 120, 320), display of a particular graphical representation including a graphical representation of a particular volume within a bodily cavity, which, in some embodiments, may be a cardiac cavity of a patient or may be a simulated cardiac or other bodily cavity in quality control, training, or testing environments. Some embodiments of block 822 may correspond to block 802 in FIG. 8A, and vice versa, according to some embodiments. As described above with reference to method 800A, the sequence of FIGS. 9A-9K shows, according to some embodiments, an example of a sequence of states of such a particular graphical representation 900. According to various embodiments associated with FIGS. 9A-9K, the particular graphical representation 900 includes various graphical representations of particular volumes within a cardiac cavity of a patient. The graphical representations of the particular volumes within the bodily cavity may be representative of different volumes within the bodily cavity and may be depicted in different manners according to various embodiments associated with method 800B. For example, in some embodiments associated with FIGS. 9A-9K, various volumes within the bodily cavity are depicted three-dimensionally as described above in this disclosure with respect to portion 902A of the particular graphical representation 900 or two-dimensionally as described above in this disclosure with respect to portion 902B of the particular graphical representation 900. The graphically represented volumes may take different forms according to various embodiments. For example, in some embodiments, one graphically represented volume may include the three-dimensionally represented envelope 906 (and portions thereof, e.g., 906A, 906B) described above in this disclosure. In some embodiments, one graphically represented volume may include the three-dimensional graphical representation 904A of a volume that, in some embodiments, represents at least a portion of a medical device (e.g., medical device 200, 300, 400). It is noted that some embodiments need not graphically represent a volume in a progressively enlarging manner as envelope 906 is in FIGS. 9A-9K, and the graphically represented volume may have a substantially constant form or a pre-generated form, as may be the case, for example, with usage of a CT image of the cardiac cavity like that shown in FIG. 9L, in some embodiments. In some embodiments, one graphically represented particular volume (which may be referred to as a second volume in some embodiments) within the bodily or cardiac cavity corresponds to at least part of a volume (e.g., which may be akin to volume 904 shown in the example of FIG. 4, in some embodiments) occupied by the at least the portion of the medical device.

In some embodiments, one graphically represented volume may include the two-dimensionally represented volume of two-dimensional graphical representation 904B that, in some embodiments, represents at least part of the least the portion of the medical device (e.g., medical device 200, 300, 400) and that, in some embodiments, may represent the bodily cavity (e.g., cardiac cavity). In some embodiments, the graphical representation of the particular volume within the cardiac cavity includes a map including a two-dimensional graphical representation of at least part of the particular volume within the cardiac cavity (for example, the two-dimensional map shown in portion 902B of the particular graphical representation 900 shown in FIGS. 9A-9K). In some embodiments, the graphical representation of the particular volume within the cardiac cavity includes a map that maps three dimensional spatial coordinates of at least part of the particular volume within the cardiac cavity onto a two-dimensional coordinate frame (for example, the two-dimensional map shown in portion 902B of the particular graphical representation 900 shown in FIGS. 9A-9K).

As described above in this disclosure, the at least the part of the particular volume within the bodily cavity may include outer or exterior portions of the particular volume. In this regard, in some embodiments, the particular graphical representation includes a map that maps three-dimensional spatial coordinates of various sub-portions (e.g., outer or exterior sub-portions) of the at least the portion of the medical device onto a two-dimensional coordinate frame. In some embodiments, the graphical representation of the particular volume within the cardiac cavity includes a three-dimensional graphical representation of the particular volume within the cardiac cavity mapped onto a two-dimensional coordinate frame. For example, in some embodiments associated with FIGS. 9A-9K, the three-dimensional graphical representation 904A of a volume (e.g., corresponding of volume of the at least the portion of the medical device) shown in portion 902A of the particular graphical representation 900 may, in some embodiments, be mapped on the two-dimensional coordinate frame of the two-dimensionally graphically represented second volume (e.g., two-dimensional graphical representation 904B) shown in portion 902B of the particular graphical representation 900. In a similar manner, three-dimensional graphical representations of the bodily cavity (e.g., cardiac cavity) may, in some embodiments, be mapped onto a two-dimensional coordinate frame of a two-dimensional graphical map.

Referring back to FIG. 8B, according to some embodiments, block 824 is associated with computer-executable instructions provided by the program and configured to cause the data processing device system (e.g., data processing device system 110, 310) to cause, via the input-output device system (e.g., input-output device system 120, 320), the particular graphical representation (e.g., particular graphical representation 900) to be annotated to include a graphical annotation set having a particular graphical attribute set at least in a state in which at least a portion of a medical device (e.g., medical device 200, 300, 400) is located at a first location within the bodily cavity (e.g., cardiac cavity). Some embodiments of block 824 may correspond to block 804 in FIG. 8A, and vice versa, according to some embodiments. According to various embodiments, the first location within the bodily cavity (e.g., cardiac cavity) is a location where the at least the portion of the medical device contacts a tissue surface in the bodily cavity (e.g., cardiac cavity). According to various embodiments, different portions of the particular graphical representation may be annotated in accordance with block 824. According to some embodiments of block 824, the data processing device system may be configured by the program at least to cause, via the input-output device system, the particular graphical representation to be annotated to include the graphical annotation set having the particular graphical attribute set at least in a state in which the at least the portion of the medical device is located at the first location within the bodily cavity (e.g., cardiac cavity) at least by causing, via the input-output device system, the graphical representation of the particular volume within the bodily cavity (e.g., cardiac cavity) to be annotated to include the graphical annotation set. The particular volume within the bodily cavity (e.g., cardiac cavity) may take different forms as per various embodiments (for example, as described above in this disclosure). In some embodiments, the data processing device system 110, 310 is configured by the program at least to cause, via the input-output device system 120, 320, the particular graphical representation to be annotated to include the graphical annotation set having the particular graphical attribute set at least in a state in which the at least the portion of the medical device is located at the first location within the cardiac cavity at least by causing, via the input-output device system 120, 320, a three-dimensional graphical representation of the at least part of the particular volume within the cardiac cavity to be annotated to include the graphical annotation set. For example, in FIG. 9C, the three-dimensional graphical representation of the first volume (e.g., represented by envelope 906 and may be all or part of first volume 905) within the bodily cavity is annotated to include a graphical annotation set 910A.

According to various embodiments, the first volume may correspond to at least a portion of a volume encompassed or otherwise defined by a tissue surface in the bodily cavity (e.g., cardiac cavity). In some embodiments, the graphical representation of the particular volume within the cardiac cavity includes a map including a two-dimensional graphical representation of at least part of the particular volume within the cardiac cavity. In some embodiments, the data processing device system (e.g., data processing device system 110, 310) is configured by the program at least to cause, via the input-output device system (e.g., input-output device system 120, 320), the particular graphical representation to be annotated to include the graphical annotation set having the particular graphical attribute set at least in a state in which the at least the portion of the medical device is located at the first location within the cardiac cavity at least by causing, via the input-output device system, the two-dimensional graphical representation of the at least part of the particular volume within the cardiac cavity to be annotated to include the graphical annotation set. For example, in FIG. 9C, the two-dimensional graphical representation 904B of the second volume within the bodily cavity is annotated to include a graphical annotation set 910A.

In some embodiments, the two-dimensional graphical representation 904B of the second volume within the bodily cavity corresponds to a volume occupied by the at least a portion of the medical device (e.g., medical device 200, 300, 400) located within the bodily cavity (e.g., cardiac cavity). In some embodiments, the second volume may correspond to at least a portion of a volume encompassed or otherwise defined by a tissue surface in the bodily cavity (e.g., cardiac cavity). In some embodiments, each of at least a three-dimensional graphical representation of a first particular volume within the bodily cavity (e.g., cardiac cavity) and a two-dimensional graphical representation of a second particular volume within the bodily cavity (e.g., cardiac cavity) are annotated (for example, as described above in this disclosure). In some embodiments, the annotation of one of the three-dimensional graphical representation of a first particular volume within the bodily cavity (e.g., cardiac cavity) and the two-dimensional graphical representation of a second particular volume within the bodily cavity (e.g., cardiac cavity) may lead to a subsequent action (e.g., in some embodiments, a machine-based action) that leads to a further annotation of the other of the three-dimensional graphical representation of a first particular volume within the bodily cavity (e.g., cardiac cavity) and the two-dimensional graphical representation of a second particular volume within the bodily cavity (e.g., cardiac cavity) (for example, as described above in this disclosure).

As described above in this disclosure, the annotation set may take various forms according to various embodiments. In some embodiments associated with FIG. 9C, the graphical annotation set 910A includes a graphical dotted line and an identifier "LSPV". According to some embodiments, the identifier "LSPV" is an identifier for a left superior pulmonary vein. It is noted that this particular annotation set is exemplary in nature and other embodiments may employ other forms and types of one or more annotations. In some embodiments, the data processing device system 110, 310 is configured by the program at least to cause, via the input-output device system 120, 320, the graphical representation of the particular volume within the cardiac cavity to include a graphical depiction of an anatomical feature of the cardiac cavity at least in a state in which the at least the portion of the medical device 200, 300, 400 is located at the first location within the cardiac cavity. In this regard, in some embodiments, the data processing device system 110, 310 is configured by the program at least to cause, via the input-output device system 120, 320, the graphical representation of the particular volume within the bodily cavity (e.g., cardiac cavity) to include a graphical depiction of at least a part of a tissue surface in the cardiac cavity at least in a state in which the at least the portion of the medical device 200, 300, 400 is located at the first location within the cardiac cavity. For example, according to some embodiments, the three-dimensionally displayed envelope 906 (and portions thereof e.g., 906A, 906B) provide a graphical depiction of at least a part of a tissue surface in the cardiac cavity. The two-dimensional graphical representation 904B of the at least part of the second volume within the bodily (e.g., cardiac) cavity described above in this disclosure shown at least in FIGS. 9B, 9C, 9D, 9E, 9F, 9G, 9H, 9J, and 9K show tissue contact information in a mapped format that graphically depicts or correspond to various tissue surfaces in a bodily cavity (e.g., a cardiac cavity), according to various embodiments.

The presence of a particular anatomical feature may, in some embodiments, be ascertainable from the depictions of various tissue surfaces. In some embodiments, at least a portion of the graphical annotation set included in the particular graphical representation graphically surrounds at least a portion of the graphical depiction of the anatomical feature at least in a state in which the at least the portion of the medical device is located at the first location within the cardiac cavity. For example, in FIG. 9C, the graphical annotation set 910A includes a dotted line that surrounds a particular graphically represented region corresponding to a left superior pulmonary vein of a cardiac cavity, according to various embodiments. In FIG. 9C, this particular form of annotation occurs in each of the three-dimensional graphical representation of the first volume (e.g., represented by envelope 906 and may be all or part of first volume 905) within the bodily cavity and the two-dimensional graphical representation 904B of the second volume within the bodily cavity. In some embodiments, the graphical annotation set identifies an anatomical feature of the bodily cavity (e.g., the cardiac cavity). For example, the surrounding dotted line of the graphical annotation set 910A provided in FIG. 9C identifies, according to some embodiments, a pulmonary vein of a cardiac cavity. In some embodiments associated with FIG. 9C, the identifier "LSPV" of the graphical annotation set 910A identifies the pulmonary vein as a left superior pulmonary vein, according to some embodiments.

Annotation of the particular graphical representation (e.g., particular graphical representation 900) to include the graphical annotation set 910A having the particular graphical attribute set may occur in response to various actions. In some embodiments, the data processing device system 110, 310 is configured by the program (e.g., per some embodiments of block 824) at least to receive, via the input-output device system 120, 320, user input defining at least part of the graphical annotation set (e.g., graphical annotation set 910A), and cause, via the input-output device system 120, 320, the particular graphical representation to be annotated to include the graphical annotation set, at least in response to the received user input. For instance, a user may utilize some form of input device, such as a mouse or keyboard of input-output device system 120, 320 to specify a location in a graphical model and an identifier or label of a graphical annotation set, as well as to specify color, font size, or other graphical attribute(s) of the graphical annotation set. In some embodiments, annotation of the particular graphical representation to include the graphical annotation set 910A having the particular graphical attribute set may occur in response to a machine-based action. For instance, the data processing device system 110, 310 may be configured to receive and analyze information from a catheter navigation system to determine a location of an anatomical feature and place a marker or graphical annotation set in a model of the bodily cavity at a location and having graphical attributes that identify a distance between at least a portion of the medical device and a location of the anatomical feature.

According to various embodiments, the particular graphical attribute set of the graphical annotation set (e.g., graphical annotation set 910A) can include one or more of various graphical attributes such as size (e.g., line size, font size), line type, font type, color, brightness, hue, degree of transparency, by way of non-limiting example. In some embodiments, the particular graphical attribute set may define particular graphical elements that are to be included in the graphical annotation set, while, in some embodiments, the particular graphical attribute set may define the particular attributes (e.g., shape, shape, size, color) of an annotation in the graphical annotation set.

According to some embodiments, block 826 in FIG. 8B is associated with computer-executable instructions provided by the program and configured to cause the data processing device system (e.g., data processing device system 110, 310) to cause, via the input-output device system (e.g., input-output device system 120, 320) and at least in response to a movement of the at least the portion of the medical device (e.g., medical device 200, 300, 400) within the bodily cavity (e.g., cardiac cavity) from the first location within the bodily cavity (e.g., cardiac cavity), a changing of the particular graphical attribute set of the graphical annotation set (e.g., graphical annotation set 910A) while the graphical annotation set, which is annotated to the particular graphical representation, graphically remains in correspondence with a same location within the patient (or simulated patient in quality control, training, or testing environments). According to various embodiments, the graphical annotation set, which is annotated to the particular graphical representation (e.g., particular graphical representation 900), graphically remains in correspondence with a same location within the patient at least during, or after, the movement of the at least the portion of the medical device within the bodily cavity. In some embodiments, at least in a state in which the particular graphical representation is caused to be annotated to include the graphical annotation set having the particular graphical attribute set, the graphical annotation set having the particular graphical attribute set corresponds to a second location within the patient, and the changing of the particular graphical attribute set of the graphical annotation set occurs while the graphical annotation set, which is annotated to the particular graphical representation, graphically remains in correspondence with the second location within the patient. According to various embodiments, the graphical annotation set (e.g., graphical annotation set 910A), which is annotated to the particular graphical representation, graphically remains in correspondence with a same location within the patient when a graphical location of the graphical annotation set in the particular graphical representation is derived from, based on, or otherwise linked to, a same location within the patient when the at least the portion of the medical device (e.g., medical device 200, 300, 400) is located at the first location within the bodily cavity (e.g., cardiac cavity) and when the at least the portion of the medical device has moved away from the first location within the bodily cavity (e.g., cardiac cavity).

For example, in some embodiments, when the at least the portion of the medical device 200, 300, 400 is located at the first location within the bodily cavity (e.g., cardiac cavity), the graphical annotation set 910A having the particular graphical attribute set corresponds to (e.g., is derived from, based on, or otherwise linked to) a second location within the patient, and, the changing of the particular graphical attribute set of the graphical annotation set (e.g., 910A) occurs while the graphical annotation set 910A, which is annotated to the particular graphical representation, graphically remains in correspondence with the second location within the patient. In some embodiments, the second location within the patient is a location within or of the cardiac cavity of the patient, such as a tissue surface in the cardiac cavity or a pulmonary vein of the cardiac cavity. In some embodiments, the input-output device system 120, 320 includes a catheter-device-location tracking system (e.g., catheter-device-location tracking system 260A, 260B). In some embodiments, the first location within the cardiac cavity is indicated by a location signal set provided by the catheter-device-location tracking system. In some embodiments, when the particular graphical representation is caused to be annotated to include the graphical annotation set (e.g., graphical annotation set 910A) having the particular graphical attribute set, the graphical annotation set having the particular graphical attribute set corresponds to a second location indicated by a location signal set provided by the catheter-device-location tracking system. According to various embodiments, the changing of the particular graphical attribute set of the graphical annotation set occurs while the graphical annotation set, which is annotated to the particular graphical representation, graphically remains in correspondence with the second location. According to various embodiments, the same location within the patient (e.g., the second location within the patient) is a location within the bodily cavity (e.g., a cardiac cavity). In some embodiments, the same location within the patient (e.g., the second location within the patient) is a location on a tissue surface in the bodily cavity (e.g., a cardiac cavity).

In some embodiments, the bodily cavity is a cardiac cavity, and the same location within the patient (e.g., the second location within the patient) is a location of a pulmonary vein of the cardiac cavity. For example, FIGS. 9C-9G show the annotation of a graphical region of the particular graphical representation 900 corresponding to a pulmonary vein with a graphical annotation set 910A, a graphical attribute set of the graphical annotation set 910A changing in response to movement of the at least the portion of the medical device 200, 300, 400 in the cardiac cavity. In FIG. 9C (and FIG. 9D in some embodiments), both the three-dimensional graphical representation of the first volume (e.g., represented by envelope 906 and may be all or part of first volume 905) within the bodily cavity (e.g., cardiac cavity) and the two-dimensional graphical representation 904B of at least a part of a second volume within the bodily cavity (e.g., cardiac cavity) have been annotated with a graphical annotation set 910A having a particular graphical attribute set in accordance with some embodiments of block 824 and as described above in this disclosure, for example, with respect to various embodiments of block 804. This particular example graphical annotation set 910A was made when the at least the portion of the medical device 200, 300, 400 was located at a first location within the bodily cavity (e.g., cardiac cavity, the first location corresponding to the graphical location 908A of the graphically depicted three-dimensional graphical representation 904A of a volume corresponding to or representing a volume occupied by the at least a portion of the medical device 200, 300, 400, as shown in the portion 902A of the particular graphical representation 900 in FIG. 9C. The graphical annotation set 910A is shown having a particular graphical attribute set (e.g., size (such as line size, font size), line type, font type, color, brightness, hue, degree of transparency) in FIG. 9C. According to some embodiments, the particular graphical attribute set of the graphical annotation set 910A is linked to or unique to the positioning of the at least the portion of the medical device 200, 300, 400 at the first location in the bodily cavity. According to some embodiments, the particular graphical attribute set of the graphical annotation set 910A is a particular graphical attribute set imparted on graphical annotation set 910A at the time of annotation. In some embodiments, at least one graphical attribute of the particular graphical attribute set is user-defined. For example, in FIG. 9C, the identifier or label "LSPV" may be selected by a user via interacting with a pop-up menu or dropdown list, or by manually inputting (e.g., via a keyboard) the content of the identifier or label upon an identification of the anatomical feature as a left superior pulmonary vein, according to various embodiments. By way of further example, a size, shape, or both size and shape of the dotted line may be user-defined according to various embodiments. In some embodiments, at least one graphical attribute of the particular graphical attribute set that is user-defined is a predetermined attribute (e.g., a predetermined attribute stored in memory device system 130, 330), according to various embodiments. In some embodiments, at least one graphical attribute of the particular graphical attribute set is machine-defined. For example, a color or a font size of the identifier or label may be machine-defined based on, e.g., the data processing device system determining a characteristic associated with a location linked to the graphical annotation set, such color or font size indicating such determined characteristic. For instance, the determined characteristic may be a degree of tissue contact experienced between one or more transducers 220, 306, 406 and a tissue surface at the location associated with the graphical annotation set, and the data processing device system may assign a particular graphical attribute set (e.g., color, font, etc.) to the graphical annotation set to indicate such degree of tissue contact. For another example, a color or a font size of the identifier or label may be machine-defined based on, e.g., the data processing device system determining a distance or direction between a location in the bodily cavity associated with the particular graphical attribute set and a location of at least a portion of the medical device in the bodily cavity, such color or font size indicating such determined distance, direction, or both. Such examples are elaborated upon below, according to some embodiments.

In FIG. 9E (and FIG. 9F in some embodiments), both the displayed three-dimensional graphical representation of the first volume (e.g., represented by envelope 906 and may be all or part of first volume 905) within the bodily cavity (e.g., cardiac cavity) and the displayed two-dimensional graphical representation 904B of at least a part of a second volume within the bodily cavity (e.g., cardiac cavity) correspond to a state in which the at least the portion of the medical device 200, 300, 400 has moved away from the first location within the bodily cavity. According to some embodiments, the state in which the at least the portion of the medical device 200, 300, 400 has moved away from the first location within the bodily cavity is exemplified in the portion 902A of the particular graphical representation 900 shown in FIG. 9E by the graphically depicted three-dimensional graphical representation 904A of a volume corresponding to or representing a volume occupied by the at least the portion of the medical device 200, 300, 400 being graphically positioned at second graphical location 908B corresponding to a second location in the bodily cavity (e.g., cardiac cavity) other than the first location (e.g., corresponding to graphical location 908A in at least FIG. 9D).

According to various embodiments, the particular graphical attribute set of the graphical annotation set 910A displayed in each of the three-dimensional graphical representation of the first volume (e.g., represented by envelope 906 and may be all or part of first volume 905) within the bodily cavity (e.g., cardiac cavity) and the two-dimensional graphical representation 904B of at least a part of a second volume within the bodily cavity (e.g., cardiac cavity) has changed in response to the movement of the at least the portion of the medical device 200, 300, 400 away from the first location within the bodily cavity in manner that visually and graphically indicates, via the graphically represented graphical annotation set 910A, that such movement of the at least the portion of the medical device 200, 300, 400 away from the first location within the bodily cavity has occurred. For example, a font size of at least label (e.g., "LSPV") indicating an anatomical feature may be increased when the medical device (e.g., 200, 300, 400) is closer to the anatomical feature, as compared to when the medical device is further from the anatomical feature, to allow the graphical annotation set of the label for the anatomical feature to provide the user with a graphical sense of movement of the medical device relative to the anatomical feature and also a distance between the medical device and the anatomical feature. In this regard, an illustrated change of distance may provide an example of how a change in a graphical attribute set of a graphical annotation set may visually and graphically indicate that movement of at least a portion of a medical device has occurred. FIGS. 9C, 9D, 9E, 9F, 9J, and 9K show examples of a usage of font size for the label "LSPV" in the two-dimensional graphical representation 904B at least to indicate that movement of the medical device has occurred. In these examples, a font size of the label "LSPV" is inversely correlated with distance between the at least the portion of the medical device and the anatomical feature, with a larger font size indicating a shorter distance between the at least the portion of the medical device 200, 300, 400 and the anatomical feature. This type of approach can efficiently provide an additional indication of distance, i.e., in an additional dimension not otherwise available to the two-dimensional map. This type of approach is also useful to help a user better understand distance between a location in a patient and a portion of a medical device in a three-dimensional graphical representation, where overlapping models (e.g., a model of a medical device overlapping a region of a model of a bodily cavity) and viewing perspectives can obscure such a distance.

The above-discussed font size change example to illustrate distance change between the at least the portion of the medical device and a location in the bodily cavity, other embodiments utilize other graphical attribute set changes to illustrate changes other than distance. For instance, a color of a graphical attribute set (e.g., a color of the label "LSPV") may indicate a direction between the at least the portion of the medical device and an anatomical feature. For example, one color may indicate that the anatomical feature is anterior the at least the portion of the medical device and another color may indicate that the anatomical feature is posterior the at least the portion of the medical device. Such color changes may be used in lieu of or in addition to other graphical attribute set changes, like the font size changes discussed above, according to various embodiments. In this regard, changes of multiple different graphical attributes can be illustrated concurrently to provide the user with multiple types of information concurrently (e.g., at least distance, direction), according to various embodiments. In some embodiments, a change of the particular graphical attribute set of the graphical annotation set (e.g., graphical annotation set 910A) from a first determined or predetermined particular graphical attribute set to a second determined or predetermined particular graphical attribute set is employed to graphically indicate the movement of the at least the portion of the medical device (e.g., medical device 200, 300, 400) away from the first location (e.g., associated with graphical location 908A) within the bodily cavity. In some embodiments, the act of changing the particular graphical attribute set of the graphical annotation set is employed to graphically indicate the movement of the at least the portion of the medical device away from the first location within the bodily cavity. According to some embodiments, the data processing device system (e.g., data processing device system 110, 310) may be configured by the program at least to cause the changing of the particular graphical attribute set of the graphical annotation set at least in response to the movement of the at least the portion of the medical device within the bodily cavity (e.g., cardiac cavity) from the first location in the bodily cavity at least by changing a size, a color, or a degree of transparency of at least a first graphical annotation in the graphical annotation set. Such a changing involving a font size is illustrated for example, as discussed above, with respect to the "LSPV" label in the two-dimensional graphical representation 904B in FIGS. 9C, 9D, 9E, 9F, 9J, and 9K, where changing of the font size among the various states illustrated by these figures occurs in response to the corresponding movements of the medical device 200, 300, 400.

In this regard, in a state in which the movement of the at least the portion of the medical device (e.g., medical device 200, 300, 400) within the bodily cavity (e.g., cardiac cavity) from the first location (e.g., associated with graphical location 908A) within the bodily cavity is a movement of the at least the portion of the medical device within the bodily cavity (e.g., cardiac cavity) from the first location to the second location (e.g., associated with graphical location 908B) within the cardiac cavity, the data processing device system (e.g., data processing device system 110, 310) is configured by the program at least to cause, via the input-output device system (e.g., input-output device system 120, 320) and in response to at least the movement of the at least the portion of the medical device within the bodily cavity (e.g., cardiac cavity) from the first location to the second location within the bodily cavity, the graphical annotation set (e.g., graphical annotation set 910A) to have a different visual appearance when the at least the portion of the medical device is located at the second location within the bodily cavity than when the at least the portion of the medical device is located at the first location within the bodily cavity. As with the above-discussed examples of the changing of the font size of the "LSPV" label in FIGS. 9C, 9D, 9E, 9F, 9J, and 9K, the font size of such "LSPV" label in the two-dimensional graphical representation 904B is larger in the state of FIG. 9D (associated with the first location represented by graphical location 908A) than compared to its size in the state of FIG. 9E (associated with the second location represented by graphical location 908B). It is noted that a change in viewing orientation of the displayed graphical annotation set (e.g., graphical annotation set 910A) does not constitute a change in a visual appearance of the graphical annotation set caused by or in response to a movement of at least a portion of the medical device. For example, in some embodiments, if a user merely rotates the three-dimensional or two-dimensional models in the graphical representations in portions 902A, 902B, respectively, of particular graphical representation 900 while the medical device is not moved or relatively moved, such a rotation in the model(s) may cause changes in how or where the graphical annotation set is graphically displayed in such model(s). However, such change(s) would not be considered to occur in response to movement of the medical device.

In some embodiments, the data processing device system (e.g., data processing device system 110, 310) is configured by the program at least to cause, via the input-output device system (e.g., input-output device system 120, 320), the graphical representation of the particular volume within the bodily cavity (e.g., cardiac cavity) to remain graphically stationary in the particular graphical representation (e.g., particular graphical representation 900) at least in a state in which the movement of the at least the portion of the medical device (e.g., medical device 200, 300, 400) within the cardiac cavity from the first location within the bodily cavity occurs. In some embodiments, the data processing device system is configured by the program at least to cause, via the input-output device system, the graphical annotation set (e.g., graphical annotation set 910A) to remain graphically stationary in the particular graphical representation at least in a state in which the movement of the at least the portion of the medical device within the bodily cavity from the first location within the cardiac cavity occurs. For example, in some embodiments, the graphical representation of the particular volume within the bodily cavity (e.g., cardiac cavity) is a three-dimensional graphical representation of the particular volume within the bodily cavity as exemplified in FIGS. 9C and 9E by the displayed three-dimensional graphical representation of the first volume (e.g., represented by envelope 906 and may be all or part of first volume 905) within the bodily cavity. A comparison of FIGS. 9C and 9E indicates that the three-dimensional graphical representation of the first volume within the bodily cavity (e.g., cardiac cavity) remains graphically stationary in the particular graphical representation 900 at least in a state in which the movement (e.g., represented by movement of the medical device between the states of FIGS. 9C and 9E) of the at least the portion of the medical device 200, 300, 400 within the bodily cavity away from the first location within the bodily cavity has occurred as per various embodiments. A comparison of FIGS. 9C and 9E also indicates that the graphical annotation set 910A annotated to the three-dimensional graphical representation of the first volume within the bodily cavity (e.g., cardiac cavity) remains graphically stationary in the particular graphical representation 900 at least in a state in which the movement of the at least the portion of the medical device 200, 300, 400 within the bodily cavity (e.g., cardiac cavity) away from the first location within the bodily cavity (e.g., cardiac cavity) has occurred as per various embodiments. A comparison of FIGS. 9C and 9E also indicates the changes in the particular graphical attribute set of the graphical annotation set 910A (e.g., per the change in font size of label "LSPV" in two-dimensional graphical representation 904B, three-dimensional graphical representation 904A or 906, or some or all of these graphical representations) made in response to the movement of the at least the portion of the medical device 200, 300, 400 within the bodily cavity (e.g., cardiac cavity) away from the first location within the bodily cavity (e.g., cardiac cavity) as per various embodiments.

The two-dimensional graphical representation 904B of at least a part of a second volume within the bodily cavity (e.g., cardiac cavity) shown in FIG. 9 corresponds, according to some embodiments, to at least a portion of the medical device 200, 300, 400 within the bodily cavity, or corresponds to the three-dimensional graphical representation 904A of a volume corresponding to or representing a volume occupied by at least a portion of the medical device 200, 300, 400 within the bodily cavity, according to some embodiments. (Note that a reference herein to a portion of the medical device within the bodily cavity need not refer to all of the portion of the medical device that is within the bodily cavity and may instead refer to a portion of the medical device that is less than all of the part of the medical device that is within the bodily cavity, according to some embodiments.) In some embodiments, various features graphically represented in the two-dimensional graphical representation 904B of at least a part of a second volume within the bodily cavity (e.g., cardiac cavity) may be graphically represented or mapped based on a particular reference frame of at least a portion of the medical device 200, 300, 400 or the three-dimensional graphical representation 904A of a volume corresponding to or representing a volume occupied by at least a portion of the medical device 200, 300, 400. Since at least a portion of the medical device 200, 300, 400 is configured to move within the bodily cavity (e.g., cardiac cavity), or the three-dimensional graphical representation 904A of volume corresponding to or representing a volume occupied by the at least a portion of the medical device 200, 300, 400 is configured to graphically move relatively to the three-dimensional graphical representation of the first volume (e.g., represented by envelope 906 and may be all or part of first volume 905) within the bodily cavity (e.g., cardiac cavity), the particular reference frame need not be a fixed reference frame, but rather, may be a moveable reference frame. Accordingly, the spatial positioning of various features graphically represented in the two-dimensional graphical representation 904B of at least a part of a second volume within the bodily cavity (e.g., cardiac cavity), or the appearance of the various features themselves may change in response to movement of at least a portion of the medical device 200, 300, 400 within the bodily cavity (e.g., cardiac cavity).

As described above in this disclosure, the data processing device system (e.g., data processing device system 110, 310) may be configured by the program (e.g., per some embodiments of block 822) at least to cause, via the input-output device system (e.g., input-output device system 120, 320), the graphical representation of the particular volume within the bodily cavity (e.g., cardiac cavity) to include a graphical depiction of information indicating various degrees of contact between at least a part of the medical device (e.g., medical device 200, 300, 400) and a tissue surface in the bodily cavity (e.g., cardiac cavity) at least in a state in which the at least the portion of the medical device is located at the first location within the bodily cavity (e.g., cardiac cavity). For example, the two-dimensional graphical representation 904B of at least a part of a second volume within the bodily cavity (e.g., cardiac cavity) shown in FIG. 9 includes a graphical depiction of information indicating various degrees of contact between at least a part of the medical device and a tissue surface in the bodily cavity (e.g., cardiac cavity). In FIG. 9C, the two-dimensional graphical representation 904B of at least a part of a second volume within the bodily cavity (e.g., cardiac cavity) includes a first grayscale pattern of information indicating various degrees of contact between at least a part of the medical device and a tissue surface in the bodily cavity in a state in which the at least the portion of the medical device, is located at the first location (e.g., corresponding to graphical location 908A) within the bodily cavity. In FIG. 9E, the two-dimensional graphical representation 904B of at least a part of a second volume within the bodily cavity (e.g., cardiac cavity) includes a second grayscale pattern of information indicating various degrees of contact between at least a part of the medical device and a tissue surface in the bodily cavity in a state in which the at least the portion of the medical device, is located at the second location within the bodily cavity (e.g., corresponding to graphical location 908B). According to various embodiments, graphical differences between the first grayscale pattern of information and the second grayscale pattern of information exist at least in part from the part of the medical device contacting different tissue regions when the at least the portion of the medical device is located at each of the first location and the second location within the bodily cavity (e.g., cardiac cavity).

According to various embodiments, in a state in which the movement of the at least the portion of the medical device (e.g., medical device 200, 300, 400) within the bodily cavity (e.g., cardiac cavity) from the first location within the bodily cavity is a movement of the at least the portion of the medical device within the bodily cavity from the first location to the second location within the bodily cavity, the data processing device system (e.g., data processing device system 110, 310) may be configured by the program (e.g., per some embodiments of block 826 in FIG. 8B) at least to cause, via the input-output device system (e.g., input-output device system 120, 320) and in response to at least the movement of the at least the portion of the medical device within the bodily cavity from the first location (e.g., associated with graphical location 908A) to the second location (e.g., associated with graphical location 908B) within the bodily cavity, the graphical annotation set (e.g., graphical annotation set 910A) to have a different visual appearance when the at least the portion of the medical device is located at the second location within the bodily cavity than when the at least the portion of the medical device is located at the first location within the bodily cavity. For example, a comparison of the two-dimensional graphical representation 904B of at least a part of a second volume within the bodily cavity (e.g., cardiac cavity) in FIGS. 9C and 9E shows, for example, the different font sizes of the label "LSPV" of the graphical annotation set 910A corresponding to a positioning of the at least the portion of the medical device 200, 300, 400 at the first location in the bodily cavity (i.e., FIG. 9C) and a positioning of the at least the portion of the medical device 200, 300, 400 at the second location in the bodily cavity (i.e., FIG. 9E), as discussed above. For another example, according to various embodiments, the dotted line in the graphical annotation set 910A, as shown in the two-dimensional graphical representation 904B of at least a part of a second volume within the bodily cavity (e.g., cardiac cavity) of FIG. 9E (i.e., corresponding to a state of a positioning at the second location), has a different size and shape than it does in FIG. 9C (i.e., corresponding to a state of a positioning at the first location).

According to various embodiments, the data processing device system (e.g., data processing device system 110, 310) is configured by the program at least to cause, via the input-output device system (e.g., input-output device system 120, 320), relative graphical movement between the graphical annotation set (e.g., graphical annotation set 910A) and the graphical representation of the particular volume within the bodily cavity (e.g., cardiac cavity) at least in response to movement of the at least the portion of the medical device (e.g., medical device 200, 300, 400) within the bodily cavity from the first location within the bodily cavity. For example, according to various embodiments, the graphical annotation set 910A as shown in FIG. 9E (i.e., corresponding to a state of a positioning at the second location) has a different positioning in the two-dimensional graphical representation 904B of at least a part of a second volume within the bodily cavity (e.g., cardiac cavity) than it does in FIG. 9C (i.e., corresponding to a state of a positioning at the first location).

According to some embodiments (e.g., as described above in this disclosure), the graphical annotation set (e.g., graphical annotation set 910A) is posted to or displayed on or in the two-dimensional graphical representation 904B of at least a part of a second volume within the bodily cavity (e.g., cardiac cavity). In this regard, the location of the graphical annotation set (e.g., 910A) may be determined in or mapped (e.g., from a three-dimensional frame of reference) to the reference frame of the two-dimensional graphical representation 904B of at least a part of a second volume within the bodily cavity, which, in some embodiments, is a moving reference frame associated with the at least the portion of the medical device (e.g., medical device 200, 300, 400). According to various embodiments, the determination of the location of the graphical annotation set (e.g., 910A) in the reference frame of the two-dimensional graphical representation 904B of at least a part of a second volume within the bodily cavity (e.g., cardiac cavity) occurs at least in a state in which the at least the portion of the medical device is located at the first location in the bodily cavity. According to various embodiments, the position of the graphical annotation set (e.g., 910A) in this moveable reference frame may be transformed into absolute coordinates. For example, the absolute coordinates may be those defined by the coordinate system of a navigation system (e.g., catheter navigation system 260A, 260B), according to some embodiments. In some embodiments, the absolute coordinates may be defined in the coordinate system of the three-dimensional graphical representation of the first volume (e.g., represented by envelope 906 and may be all or part of first volume 905) within the bodily cavity (e.g., cardiac cavity). According to various embodiments, this transformation is accomplished using positional information indicating the location and orientation of the at least the portion of the medical device 200, 300, 400, for example, as provided by catheter navigation system 260A or 260B.

According to various embodiments, the data processing device system (e.g., data processing device system 110, 310) may be configured by the program at least to cause, via the input-output device system (e.g., input-output device system 120, 320), a graphical repositioning of the graphical annotation set (e.g., graphical annotation set 910A) from a first location in the particular graphical representation (e.g., particular graphical representation 900) to a second location in the particular graphical representation at least in response to movement of the at least the portion of the medical device (e.g., medical device 200, 300, 400) within the bodily cavity (e.g., cardiac cavity) from the first location within the bodily cavity, each of the first location in the particular graphical representation and the second location in the particular graphical representation corresponding to the same location within the patient. In some embodiments, each of the first location in the particular graphical representation and the second location in the particular graphical representation is a location in the graphical representation of the particular volume within the cardiac cavity.

For example, the graphical annotation set 910A as shown in FIG. 9C is positioned at a first location in the two-dimensional graphical representation 904B of at least a part of a second volume within the bodily cavity (e.g., cardiac cavity) and is positioned as shown in FIG. 9E at a second location in the two-dimensional graphical representation 904B of at least a part of a second volume within the bodily cavity (e.g., cardiac cavity) in response to movement of the at least the portion of the medical devices 200, 300, 400 within the bodily cavity away from the first location (e.g., corresponding to graphical location 908A) within the bodily cavity. According to various embodiments, each of the first location in the two-dimensional graphical representation 904B of at least a part of a second volume within the bodily cavity (e.g., cardiac cavity) and the second location in the two-dimensional graphical representation 904B of at least a part of a second volume within the bodily cavity (e.g., cardiac cavity) correspond to the same location within the patient. For example, once "posted to" (e.g., graphically placed onto, graphically pinned to, or displayed on or in) the two-dimensional graphical representation 904B of at least a part of a second volume within the bodily cavity, the graphical annotation set (e.g., graphical annotation set 910A) may, in some embodiments, be linked to, pinned to, or correspond to a particular location within the patient. For example, in FIG. 9C, the graphical annotation set 910A having the particular graphical attribute set was posted at a first location, referred to in this example as a first graphical location, in the two-dimensional graphical representation 904B of at least a part of a second volume within the bodily cavity (e.g., cardiac cavity) during a state in which the at least the portion of the medical device 200, 300, 400 is located at a first location within the bodily cavity. According to various embodiments, the first graphical location in the two-dimensional graphical representation 904B of at least a part of a second volume within the bodily cavity (e.g., cardiac cavity) defines a particular location on the at least the portion of the medical device 200, 300, 400 that can be transposed into a set of absolute coordinates associated with a particular location within the patient, in some embodiments. According to some embodiments, such particular location may be where a portion of an anatomical feature within the patient's bodily cavity (e.g., cardiac cavity) existed at the time of posting or pinning of the graphical annotation set, according to some embodiments. The set of absolute coordinates may be determined from location signals provided by a navigation system (e.g., catheter navigation system 260A, 260B) or from a combination of the location signals and pre-determined or determined spatial relationships between sensed (e.g., by the navigation system) and non-sensed (e.g., not sensed by the navigation system) parts of the at least the portion of the medical device 200, 300, 400. When the at least the portion of the medical device 200, 300, 400 moves away from the first location within the bodily cavity, a new position of the graphical annotation set 910A may be defined at a second location, referred to in this example as a second graphical location, in the two-dimensional graphical representation 904B of at least a part of a second volume within the bodily cavity (e.g., cardiac cavity). While the second graphical location of the graphical annotation set 910A in the two-dimensional graphical representation 904B is different from the first graphical location of the graphical annotation set 910A in the two-dimensional graphical representation 904B due to the movement of the medical device, the graphical annotation set 910A, having been posted to or pinned to the set of absolute coordinates remains in correspondence with the set of absolute coordinates, which may be associated with the particular location within the patient.

For example, in some embodiments, the data processing device system (110, 310) may be configured by the program to determine a ray or vector from the second location within the patient defining the location of the graphical annotation set 910A in the absolute coordinate system to a particular location on the at least the portion of the medical device 200, 300, 400. For example, in some embodiments, the ray or vector may extend from the second location within the patient defining the location of the graphical annotation set 910A to a center-of-mass of the volume occupied by the at least the portion of the medical device. For instance, in some embodiments in which the at least the portion of the medical device 200, 300, 400 has an essentially spheroid shape of arrayed elongate members 304, such center-of-mass might be a centroid of such essentially spheroid shape. An intersection by the ray or vector of a physical region or a virtual region (e.g., a region over an opening) of the at least the portion of the medical device 200, 300, 400 may, in some embodiments, be employed to define a third location of the graphical annotation set 910A in the absolute coordinate system, the third location within the patient corresponding to the second location within the patient via a projection of the second location within the patient along the ray or vector. According to various embodiments, such a ray or vector may be determined from navigation system (e.g., catheter navigation system 260A, 260B) data. According to various embodiments, the third location within the patient may be transposed from the absolute coordinate system to the coordinate system of the two-dimensional graphical representation 904B of at least a part of a second volume within the bodily cavity (e.g., cardiac cavity) to define the second graphical location in the two-dimensional graphical representation 904B of at least a part of a second volume within the bodily cavity (e.g., cardiac cavity).

Other methods of projecting the second location within the patient defining the location of the graphical annotation set 910A onto the at least the portion of the medical device 200, 300, 400 that has moved away from the first location within the bodily cavity (e.g., cardiac cavity) may be employed according to various embodiments. For example, in some embodiments, the ray or vector may have a different orientation than that described above in this disclosure. For example, the second location within the patient as defined in the absolute coordinate frame may be located on a region of a tissue surface in the bodily cavity (e.g., cardiac cavity), and the ray or vector may be selected to have, at the second location within the patient, a normal orientation to the region of the tissue surface, according to some embodiments. In some embodiments, the second location within the patient as defined in the absolute coordinate frame may be located in a bodily opening, such as a pulmonary vein, and the ray or vector may be selected to have, at the second location within the patient, an orientation parallel to an axis of or an extension of an axis of the bodily opening. In some embodiments, the at least the portion of the medical device 200, 300, 400, may be translating along a particular direction, and the ray or vector may be selected to have, at the second location within the patient, an orientation parallel to a particular direction. In some cases, some of these alternate embodiments of the ray or vector orientation will cause the ray or vector to intersect the at least the portion of the medical device 200, 300, 400 at a different intersection location than the embodiments describe above. Regardless, the resulting movement of the graphical annotation set 910A to the particular second graphical location in the two-dimensional graphical representation 904B of at least a part of a second volume within the bodily cavity (e.g., cardiac cavity) corresponding to the different intersection location is such that the particular second graphical location still corresponds to the same second location within the patient.

In some embodiments, at least in a state in which the at least the portion of the medical device (e.g., medical device 200, 300, 400) is located at the first location (e.g., represented by graphical location 908A) within the bodily cavity (e.g., cardiac cavity), the particular graphical attribute set of the graphical annotation set (e.g., graphical annotation set 910A), may visually indicate a first distance between the at least the portion of the medical device and a particular location in the bodily cavity. For example, the font size of the label "LSPV" in FIG. 9C may visually indicate, in some embodiments, a first distance between at least a portion of the medical device and a particular location corresponding to the left superior pulmonary vein in the cardiac cavity. In some embodiments, in a state in which the movement of the at least the portion of the medical device within the bodily cavity (e.g., cardiac cavity) is from the first location within the bodily cavity (e.g., cardiac cavity) to a second location (e.g., represented by graphical location 908B) within the bodily cavity, the data processing device system (e.g., data processing device system 110, 310) may be configured by the program (e.g., per some embodiments of block 826) at least to cause, via the input-output device system (e.g., input-output device system 120, 320) and in response to at least the movement of the at least the portion of the medical device 200, 300, 400 within the bodily cavity from the first location to the second location within the bodily cavity, the particular graphical attribute set of the graphical annotation set (e.g., graphical annotation set 910A) to be changed in a manner that the particular graphical attribute set of the graphical annotation set is changed, at least in a state in which the at least the portion of the medical device 200, 300, 400 is located at the second location within the cardiac cavity, to visually indicate a second distance between the at least the portion of the medical device and the particular location within the bodily cavity (e.g., cardiac cavity), the second location other than the first location, and the second distance different than the first distance. For example, the smaller font size of the label "LSPV" in FIG. 9E compared to that of FIG. 9C may visually indicate, in some embodiments, a second distance (greater than the first distance represented by the larger font size in FIG. 9C) between the at least the portion of the medical device and the particular location corresponding to the left superior pulmonary vein in the cardiac cavity.

In some embodiments associated with the annotating of the three-dimensional graphical representation of the first volume (e.g., represented by envelope 906 and may be all or part of first volume 905) within the bodily cavity (e.g., cardiac cavity) with a graphical annotation set (e.g., graphical annotation set 910A) at least in a state in which at least a portion of the medical device (e.g., medical device 200, 300, 400) is located at a first location (e.g., corresponding to graphical location 908A) within the bodily cavity, the graphical attribute set of the graphical annotation set may vary in accordance with a change in distance between the at least the portion of the medical device 200, 300, 400 and a second location within the patient to which the graphical location of the graphical annotation set in three-dimensional graphical space corresponds. For example, FIG. 9D corresponds to a state in which at least a portion of the medical device 200, 300, 400 is at a first location in the bodily cavity that corresponds to graphical location 908A of three-dimensional graphical representation 904A of the at least the portion of the medical device 200, 300, 400. This first location of the at least the portion of the medical device 200, 300, 400 is in close proximity to a second location within the patient to which the graphical annotation set 910A corresponds. In this regard, the graphical attribute set of the graphical annotation set 910A may impart a particular color (e.g., green) to at least part of the graphical annotation set 910A to indicate this "close proximity" condition. FIGS. 9E and 9F correspond to a state in which the at least the portion of the medical device 200, 300, 400 is at a different location in the bodily cavity, as compared to the state of FIG. 9D. This different location in the bodily cavity corresponds to graphical location 908B of three-dimensional graphical representation 904A of the at least the portion of the medical device 200, 300, 400. This different location of the at least the portion of the medical device 200, 300, 400 is at a further distance (e.g., as compared to the state of FIG. 9D) to the second location within the patient to which the graphical annotation set 910A corresponds. In this regard, the graphical attribute set of the graphical annotation set 910A may impart a particular color (e.g., yellow) to at least part of the graphical annotation set 910A to indicate this "further distance" condition.

Figure 9G:
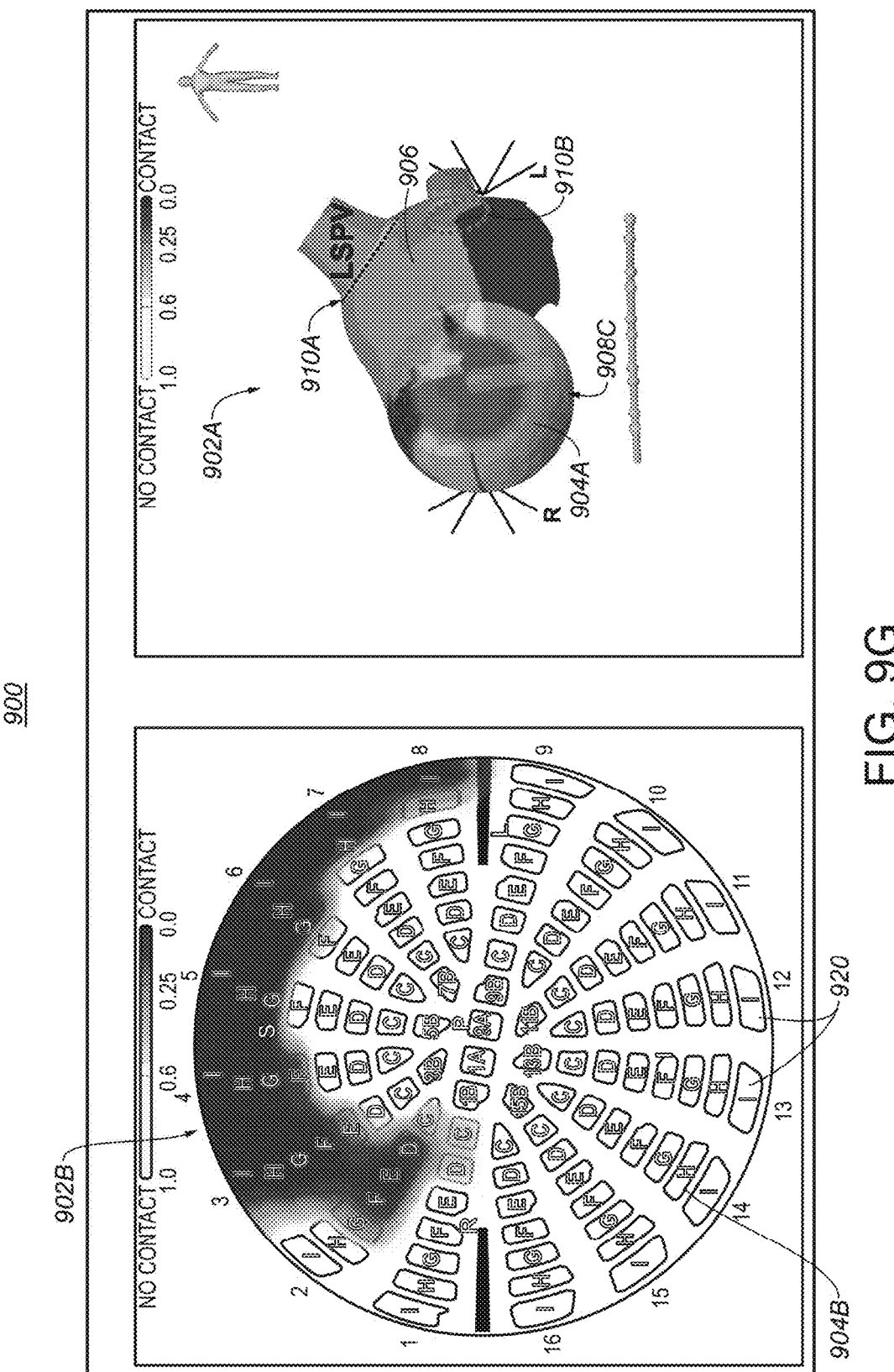

In FIGS. 9E and 9F, a second graphical annotation set 910B including a second dotted line and a graphical identifier or label "LIPV" has been annotated (for example, by methods the same or similar to as those described in this disclosure). FIG. 9G corresponds to a state in which the at least the portion of the medical device 200, 300, 400 corresponds to at least three-dimensional graphical representation 904A, which is located at graphical location 908C in the state of FIG. 9G and which is associated with a positioning of the at least a portion of the medical device 200, 300, 400 at an even further distance (e.g., as compared to the state of FIGS. 9C, 9D, 9E, 9F) to the second location within the patient to which the graphical annotation set 910A corresponds. In this regard, the graphical attribute set of the graphical annotation set 910A may impart a particular color (e.g., red) to at least part of the graphical annotation set 910A to indicate the "even further distance" condition.

According to various embodiments, it may be desirable to reposition the at least the portion of the medical device 200, 300, 400 back to a location in proximity to the second location within the patient to which the graphical annotation set 910A corresponds. For example, in some ablation procedures, it may be desirable to map electrophysiological activity at a previously ablated region identified by the graphical annotation set. Advantageously, the changing of the graphical attribute set of the graphical annotation set 910A in response to changes in distance between the at least the portion of the medical device 200, 300, 400 and the second location within the patient to which the graphical annotation set corresponds allows a user to better ascertain whether the at least the portion of the medical device 200, 300, 400 has returned to a location in sufficient proximity to the second location within the patient to which the graphical annotation set 910A corresponds (e.g., by repositioning the at least the portion of the medical device 200, 300, 400 until at least part of the graphical annotation set 910A turns green in color as per the example embodiments described above).

Determining the proximity of the at least the portion of the medical device 200, 300, 400 to the second location within the patient to which the graphical annotation set 910A corresponds via the state of the graphical attribute set of the graphical annotation set 910A may be accomplished in additional or alternate manners, according to various embodiments. For example, FIG. 9D corresponds, in some embodiments, to a state in which the placement of the graphical annotation set 910A in the two-dimensional graphical representation 904B of at least a part of a second volume within the bodily cavity (e.g., cardiac cavity) corresponds to a positioning of the at least the portion of the medical device 200, 300, 400 at the first location (corresponding to graphical location 908A) within the bodily cavity at the time of annotation. In FIG. 9D, the particular graphical attribute set of the graphical annotation set 910A indicates a particular size and shape of at least the dotted line of the graphical annotation set 910A annotated to the two-dimensional graphical representation 904B. FIGS. 9E and 9F correspond, in some embodiments, to a state in which the placement of the graphical annotation set 910A in the two-dimensional graphical representation 904B of at least a part of a second volume within the bodily cavity (e.g., cardiac cavity) corresponds to a movement of the at least the portion of the medical device 200, 300, 400 away from the first location within the bodily cavity (e.g., cardiac cavity) to a second location (e.g., corresponding to graphical location 908B) within the bodily cavity. According to various embodiments, the location of the graphical annotation set 910A in the two-dimensional graphical representation 904B is different in FIGS. 9E, 9F as compared with FIG. 9D. This difference may occur, in some embodiments, as described above in this disclosure, when at least a location of the graphical annotation set 910A in three-dimensional space is projected along a ray or vector onto the second volume (such as the volume of the medical device 200, 300, 400). According to various embodiments, the graphical attribute set of the graphical annotation set 910A displayed in the two-dimensional graphical representation 904B of at least a part of a second volume within the bodily cavity (e.g., cardiac cavity) in FIGS. 9E, 9F causes the dotted line of the graphical annotation set 910A to be different (e.g., smaller in area surrounded) than its corresponding representation in FIG. 9D due to the movement of the medical device away from the second location within the patient to which the graphical annotation set 910A corresponds.

According to various embodiments, a graphical annotation set may alternatively or additionally have a different shape or other change in graphical attribute to illustrate distance or relative positioning between a portion of the medical device and a location in the bodily cavity to which the graphical annotation set corresponds. For instance, according to various embodiments, the state of one or more graphical attributes (e.g., different sizes, colors, shapes, opacities, or other graphical attribute) of the graphical annotation set in two-dimensional graphical representation 904B of at least a part of a second volume within the bodily cavity (e.g., cardiac cavity) may be employed to visually indicate a particular distance of the at least the portion of the medical device 200, 300, 400 from a particular location within the bodily cavity (e.g., cardiac cavity) such as the first location (e.g., corresponding to graphical location 908A). It is noted that, in some embodiments, changes in a graphical attribute set of a graphical annotation set (e.g., graphical annotation set 910A) may also be due in part to graphical distortions associated with the two-dimensional mapping.

In some embodiments, the changing of the particular graphical attribute set of the graphical annotation set 910A at least in response to movement of the at least the portion of the medical device 200, 300, 400 within the bodily cavity (e.g., cardiac cavity) from the first location (e.g., corresponding to graphical location 908A) in the bodily cavity (e.g., cardiac cavity) causes, via the input-output device system, at least a graphical removal of at least a first graphical annotation in the graphical annotation set 910A. For example, according to some embodiments, FIG. 9G corresponds to a state in which the at least the portion of the medical device 200, 300, 400 has moved even further away from the first location within the bodily cavity than was associated with FIGS. 9E, 9F. In this regard, a pre-determined or determined threshold distance value between the at least the portion of the medical device and the first location has been met or surpassed, and, consequently, the graphical annotation set 910A is no longer visible in the two-dimensional graphical representation 904A.

In this regard, in some embodiments, the data processing device system (e.g., data processing device system 110, 310) may be configured by the program (e.g., per some embodiments of block 826 in FIG. 8B) to calculate a distance "x" in three-dimensional space between a particular location on the at least the portion of the medical device (e.g., medical device 200, 300, 400) and the location where the graphical annotation set was posted or pinned (e.g., as described above in this disclosure, and, e.g., corresponding to graphical location 908A). According to some embodiments, the data processing device system may be configured by the program (e.g., per some embodiments of block 826) to determine if the distance "x" is within a specific range, NearThreshold<x<FarThreshold. In some embodiments, at least part of the graphical annotation set (e.g., graphical annotation set 910A) is represented in at least part of the particular graphical representation 900 (e.g., the two-dimensional graphical representation 904B of at least a part of a second volume within the bodily cavity (e.g., cardiac cavity)) with a graphical transparency that is interpolated (e.g., linearly interpolated) between 100% graphically transparent at the FarThreshold or further and 0% graphically transparent at the NearThreshold or closer. Graphically, this configuration provides a visual effect that, when the at least the portion of the medical device 200, 300, 400 is near or at the location of the graphical annotation set that was posted or pinned, the at least the part of the graphical annotation set is rendered at or near full opacity, but fades as the distance between the at least the portion of the medical device 200, 300, 400 and the location of the graphical annotation set that was posted or pinned increases, until the graphical annotation set is no longer graphically shown.

In some embodiments, the above-discussed threshold distance or near and far thresholds may be different for different anatomical features. For instance, it may be desired to have larger anatomical features be more visible than smaller anatomical features at a same distance from the at least the portion of the medical device and, therefore, a larger anatomical feature may have a greater threshold distance in which it is displayed or it may have its opacity levels with respect to the near and far thresholds adjusted in order for it to be displayed more prominently compared to a smaller anatomical feature at the same distance from the at least the portion of the medical device, in some embodiments.

Figure 9H:
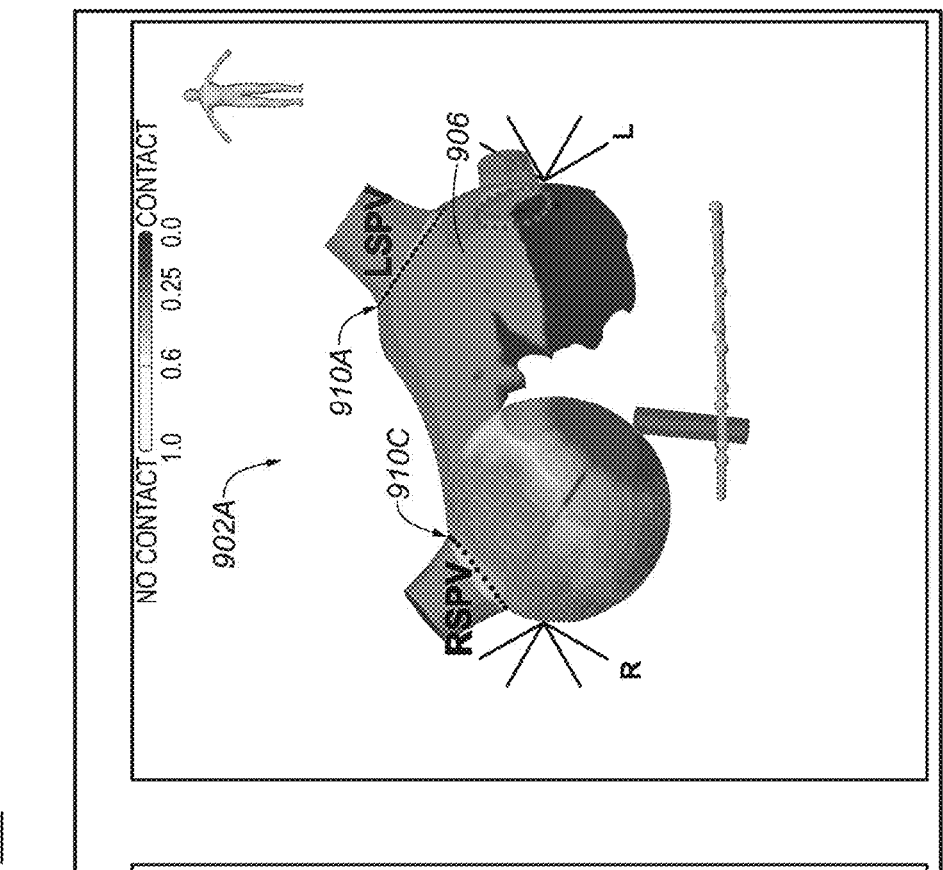

FIG. 9H corresponds to a state in which the at least the portion of the medical device 200, 300, 400 has been positioned within the bodily cavity (e.g., cardiac cavity) in the vicinity of another pulmonary vein. Another graphical annotation set 910C including a dotted line and a graphical identifier or label "RSPV" indicating the Right Superior Pulmonary Vein have been annotated to the particular graphical representation 900 in the state of FIG. 9H.

According to various embodiments, the data processing device system (e.g., data processing device system 110, 310) may be configured by the program (e.g., per some embodiments of block 822) at least to cause, via the input-output device system (e.g., input-output device system 120, 320), the graphical representation of the particular volume within the bodily cavity (e.g., cardiac cavity) to include a graphical depiction of information indicating various degrees of contact between at least a part of the medical device (e.g., medical device 200, 300, 400) and a tissue surface in the bodily cavity (e.g., cardiac cavity) at least in a state in which the at least the portion of the medical device is located at the first location (e.g., corresponding to graphical location 908A) within the bodily cavity. For example, the two-dimensional graphical representation 904B of at least a part of a second volume within the bodily cavity shows degrees of contact information in a grayscale manner in at least FIG. 9C. FIG. 9H also shows degrees of contact information in a similar manner in graphical representation 904B.

In some embodiments, the data processing device system is configured by the program (e.g., per some embodiments of block 822) at least to cause, via the input-output device system, the graphical representation of the particular volume within the cardiac cavity to include a graphical depiction of information indicating no contact between the at least the part of the medical device and the tissue surface in the bodily cavity (e.g., cardiac cavity) at least in a state in which the at least the portion of the medical device is located at a second location within the bodily cavity (e.g., cardiac cavity), the second location other than the first location. For example, FIG. 9I may be considered to correspond to a state in which the at least the portion of the medical device 200, 300, 400 is moving away from such first location toward a second location in the bodily cavity where no tissue contact exists between the medical device and the tissue surface of the bodily cavity. In the state of FIG. 9I, the lack of any grayscale pattern in the two-dimensional graphical representation 904B of at least a part of a second volume within the bodily cavity (e.g., cardiac cavity) may indicate the absence of such tissue contact. It is noted that the graphical annotation set 910A does not appear in the two-dimensional graphical representation 904B of at least a part of a second volume within the bodily cavity (e.g., cardiac cavity) in the state of FIG. 9I indicating, according to some embodiments, that the portion of the medical device 200, 300, 400 is beyond a desired threshold distance from the location to which the graphical annotation set 910A corresponds (e.g., was posted or pinned to).

FIG. 9J corresponds to a state in which the at least the portion of the medical device 200, 300, 400 has moved closer (for example, as compared to FIG. 9I) to the location to which the graphical annotation set 910A corresponds. According to various embodiments, in the state of FIG. 9J, the graphical annotation set 910A has reappeared (compared to the state of FIG. 9I) in the two-dimensional graphical representation 904B of at least a part of a second volume within the bodily cavity (e.g., cardiac cavity), indicating that the at least the portion of the medical device 200, 300, 400 has moved within a threshold distance range to the location to which the graphical annotation set 910A corresponds. According to various embodiments, the graphical attribute set of the graphical annotation set 910A annotated to the three-dimensional envelope 906 shown in FIG. 9J may also undergo a change reflecting this closer proximity (for example, a color change from red to yellow as described above in this disclosure). In the state of FIG. 9J, the graphical annotation set 910B has also reappeared (compared to the state of FIG. 9I) in the two-dimensional graphical representation 904B of at least a part of a second volume within the bodily cavity (e.g., cardiac cavity), indicating that the at least the portion of the medical device 200, 300, 400 has also moved within a threshold distance range (i.e., associated with graphical annotation set 910B) to the location to which the graphical annotation set 910B corresponds (e.g., was posted or pinned to).

Figure 9K:
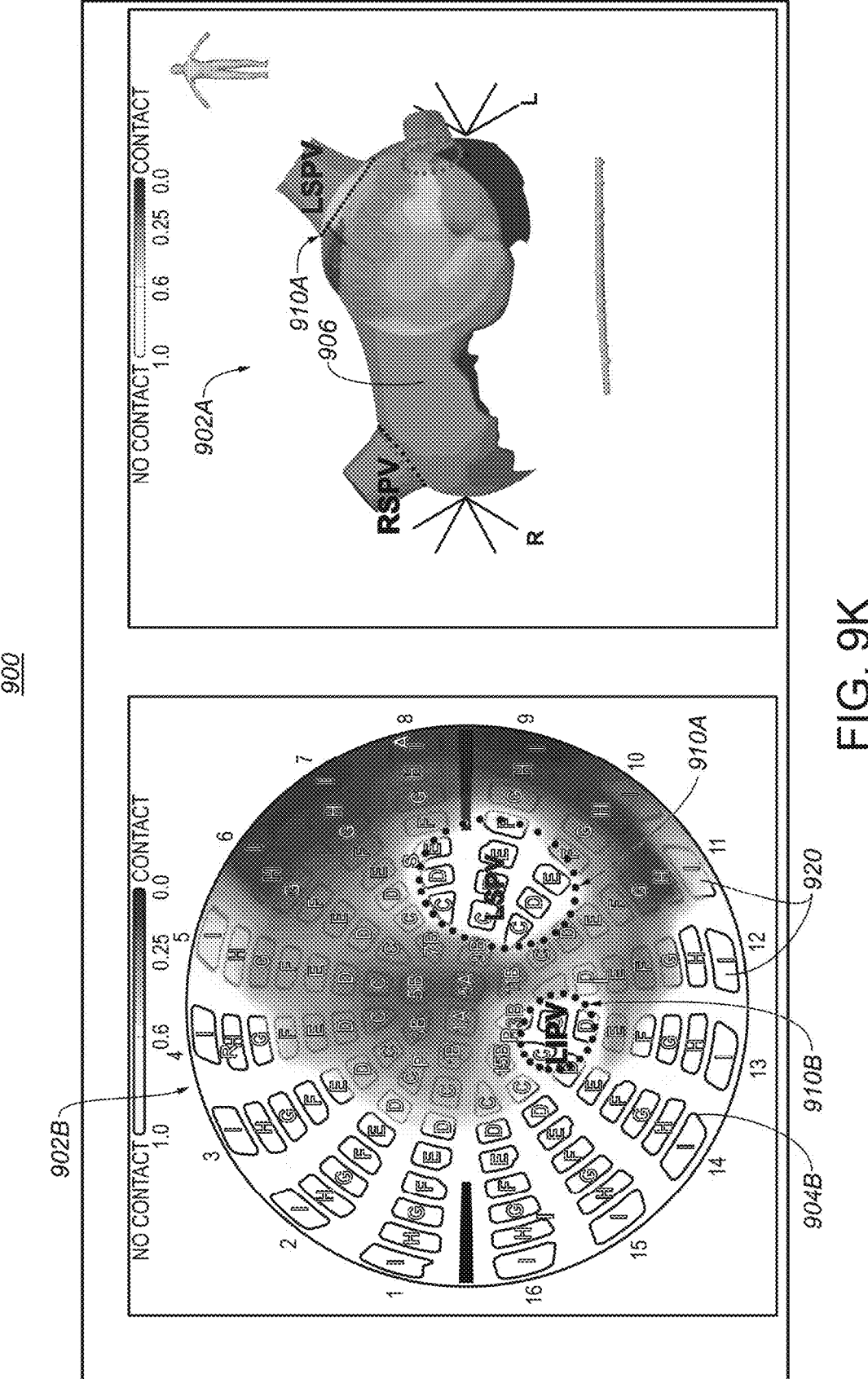
Figure 9L:
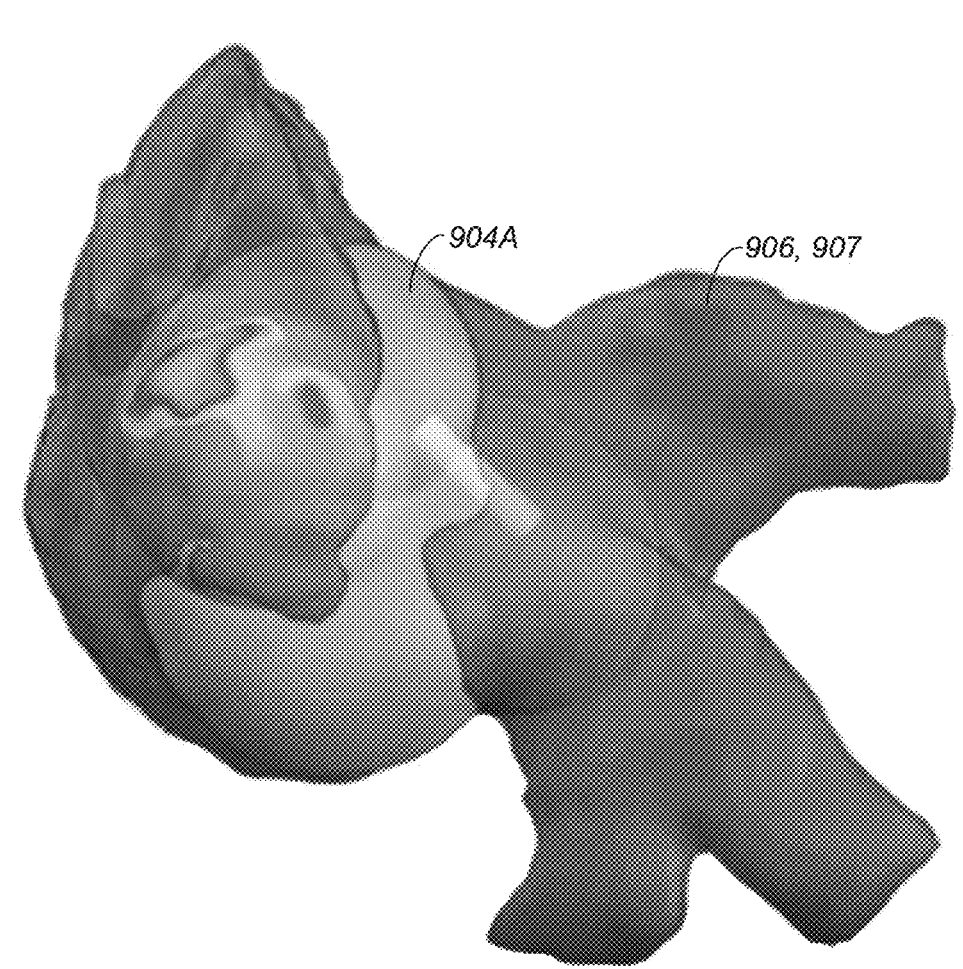
FIG. 9L illustrates a portion of a particular graphical representation in which a three-dimensional graphical model of a bodily cavity is graphically represented as a computerized tomography ("CT") scan-based image, according to various example embodiments.

FIG. 9K corresponds to a state in which the at least the portion of the medical device 200, 300, 400 has moved to, or in very close proximity to, the location to which the graphical annotation set 910A corresponds. According to various embodiments, in the state of FIG. 9K, the graphical attribute set of the graphical annotation set 910A has changed to cause the dotted line of the graphical annotation set 910A to assume a size similar to, or the same as, what the dotted line had when it was first annotated to the two-dimensional graphical representation 904B of at least a part of a second volume within the bodily cavity (e.g., cardiac cavity) (for example as shown in FIGS. 9C, 9D). According to various embodiments, this similar size may act as a graphical cue to an observer that the at least the portion of the medical device 200, 300, 400 has moved to, or is in very close proximity to the location to which the graphical annotation set 910A corresponds. According to various embodiments, the graphical attribute set of the graphical annotation set 910A annotated to the three-dimensional envelope 906 shown in FIG. 9K may also undergo a change reflecting this particular proximity condition (for example, a color change from yellow to green as described above in this disclosure). It is noted that, although the graphical annotation set 910A in FIG. 9K has been repositioned (i.e., as compared to FIG. 9J) to a particular location in the two-dimensional graphical representation 904B of at least a part of a second volume within the bodily cavity (e.g., cardiac cavity) that is very similar to the respective location of the graphical annotation set 910A in the two-dimensional graphical representation 904B in FIGS. 9C, 9D, such may not be the case in other embodiments, especially in cases where the at least the portion of the medical device has a different orientation when repositioned back to the location of the annotation in three-dimensional space (e.g., FIG. 9K) than it had when the graphical annotation set 910A was first posted or pinned (e.g., FIGS. 9C, 9D).

While some of the embodiments disclosed above are described with examples of cardiac mapping, ablation, or both, the same or similar embodiments may be used for mapping, ablating, or both, other bodily organs, for example with respect to the intestines, the bladder, or any bodily organ to which the devices of the present invention may be introduced.

Subsets or combinations of various embodiments described above can provide further embodiments.

These and other changes can be made to the invention in light of the above-detailed description. In general, in the following claims, the terms used should not be construed to limit the invention to the specific embodiments disclosed in the specification and the claims, but should be construed to include other transducer-based device systems including all medical treatment device systems and all medical diagnostic device systems in accordance with the claims. Accordingly, the invention is not limited by the disclosure, but instead its scope is to be determined entirely by the claims.

What is claimed is:

1. A medical system comprising:
    a data processing device system;
    an input-output device system communicatively connected to the data processing device system; and
    a memory device system communicatively connected to the data processing device system and storing a program executable by the data processing device system, the data processing device system configured by the program at least to:
    cause, via the input-output device system, display of a particular graphical representation including a graphical representation of a particular volume within a cardiac cavity of a patient;
    cause, via the input-output device system, the particular graphical representation to be annotated to include a graphical annotation set having a particular graphical attribute set at least in a state in which at least a portion of a medical device is located at a first location within the cardiac cavity; and
    cause, via the input-output device system and at least in response to a movement of the at least the portion of the medical device within the cardiac cavity from the first location within the cardiac cavity, a changing of the particular graphical attribute set of the graphical annotation set while the graphical annotation set, which is annotated to the particular graphical representation, graphically remains in correspondence with a same location within the patient.

2. The medical system of claim 1, wherein the data processing device system is configured by the program at least to cause, via the input-output device system, the graphical representation of the particular volume within the cardiac cavity to include a graphical depiction of at least a part of a tissue surface in the cardiac cavity at least in the state in which the at least the portion of the medical device is located at the first location within the cardiac cavity.

3. The medical system of claim 1, wherein the data processing device system is configured by the program at least to cause, via the input-output device system, the graphical representation of the particular volume within the cardiac cavity to include a graphical depiction of information indicating various degrees of contact between at least a part of the medical device and a tissue surface in the cardiac cavity at least in the state in which the at least the portion of the medical device is located at the first location within the cardiac cavity.

4. The medical system of claim 3, wherein the data processing device system is configured by the program at least to cause, via the input-output device system, the graphical representation of the particular volume within the cardiac cavity to include a graphical depiction of information indicating no contact between the at least the part of the medical device and the tissue surface in the cardiac cavity at least in a state in which the at least the portion of the medical device is located at a second location within the cardiac cavity, the second location other than the first location.

5. The medical system of claim 4, wherein, in a state in which the movement of the at least the portion of the medical device within the cardiac cavity from the first location within the cardiac cavity is a movement of the at least the portion of the medical device within the cardiac cavity from the first location to the second location within the cardiac cavity, the data processing device system is configured by the program at least to cause, via the input-output device system and in response to at least the movement of the at least the portion of the medical device within the cardiac cavity from the first location to the second location within the cardiac cavity, the graphical annotation set to have a different visual appearance when the at least the portion of the medical device is located at the second location within the cardiac cavity than when the at least the portion of the medical device is located at the first location within the cardiac cavity.

6. The medical system of claim 1, wherein the data processing device system is configured by the program at least to cause, via the input-output device system, the graphical representation of the particular volume within the cardiac cavity to include a graphical depiction of an anatomical feature of the cardiac cavity at least in the state in which the at least the portion of the medical device is located at the first location within the cardiac cavity.

7. The medical system of claim 6, wherein at least a portion of the graphical annotation set included in the particular graphical representation graphically surrounds at least a portion of the graphical depiction of the anatomical feature at least in the state in which the at least the portion of the medical device is located at the first location within the cardiac cavity.

8. The medical system of the claim 1, wherein the graphical annotation set identifies an anatomical feature of the cardiac cavity.

9. The medical system of claim 1, wherein the data processing device system is configured by the program at least to:
    receive, via the input-output device system, user input defining at least part of the graphical annotation set; and
    cause, via the input-output device system, the particular graphical representation to be annotated to include the graphical annotation set, at least in response to the received user input.

10. The medical system of claim 1, wherein the data processing device system is configured by the program at least to cause, via the input-output device system, the particular graphical representation to be annotated to include the graphical annotation set having the particular graphical attribute set at least in the state in which the at least the portion of the medical device is located at the first location within the cardiac cavity at least by causing, via the input-output device system, the graphical representation of the particular volume within the cardiac cavity to be annotated to include the graphical annotation set.

11. The medical system of claim 10, wherein the data processing device system is configured by the program at least to cause, via the input-output device system, relative graphical movement between the graphical annotation set and the graphical representation of the particular volume within the cardiac cavity at least in response to movement of the at least the portion of the medical device within the cardiac cavity from the first location within the cardiac cavity.

12. The medical system of claim 1, wherein the data processing device system is configured by the program at least to cause, via the input-output device system, a graphical repositioning of the graphical annotation set from a first location in the particular graphical representation to a second location in the particular graphical representation at least in response to movement of the at least the portion of the medical device within the cardiac cavity away from the first location within the cardiac cavity, each of the first location in the particular graphical representation and the second location in the particular graphical representation corresponding to the same location within the patient.

13. The medical system of claim 12, wherein each of the first location in the particular graphical representation and the second location in the particular graphical representation is a location in the graphical representation of the particular volume within the cardiac cavity.

14. The medical system of claim 1,
wherein the graphical representation of the particular volume within the cardiac cavity includes a map comprising a two-dimensional graphical representation of at least part of the particular volume within the cardiac cavity, and
wherein the data processing device system is configured by the program at least to cause, via the input-output device system, the particular graphical representation to be annotated to include the graphical annotation set having the particular graphical attribute set at least in the state in which the at least the portion of the medical device is located at the first location within the cardiac cavity at least by causing, via the input-output device system, the two-dimensional graphical representation of the at least part of the particular volume within the cardiac cavity to be annotated to include the graphical annotation set.

15. The medical system of claim 1, wherein the data processing device system is configured by the program at least to cause, via the input-output device system, the graphical representation of the particular volume within the cardiac cavity to remain graphically stationary in the particular graphical representation at least in a state in which the movement of the at least the portion of the medical device within the cardiac cavity from the first location within the cardiac cavity occurs.

16. The medical system of claim 15, wherein the graphical representation of the particular volume within the cardiac cavity is a three-dimensional graphical representation of the particular volume within the cardiac cavity.

17. The medical system of claim 1, wherein the data processing device system is configured by the program at least to cause, via the input-output device system, the graphical annotation set to remain graphically stationary in the particular graphical representation at least in a state in which the movement of the at least the portion of the medical device within the cardiac cavity from the first location within the cardiac cavity occurs.

18. The medical system of claim 1, wherein, at least in the state in which the at least the portion of the medical device is located at the first location within the cardiac cavity, the particular graphical attribute set of the graphical annotation set visually indicates a first distance between the at least the portion of the medical device and a particular location in the cardiac cavity.

19. The medical system of claim 18, wherein, in a state in which the movement of the at least the portion of the medical device within the cardiac cavity from the first location within the cardiac cavity is a movement of the at least the portion of the medical device within the cardiac cavity from the first location to a second location within the cardiac cavity, the data processing device system is configured by the program at least to cause, via the input-output device system and in response to at least the movement of the at least the portion of the medical device within the cardiac cavity from the first location to the second location within the cardiac cavity, the particular graphical attribute set of the graphical annotation set to be changed in a manner that the particular graphical attribute set of the graphical annotation set is changed, at least in a state in which the at least the portion of the medical device is located at the second location within the cardiac cavity, to visually indicate a second distance between the at least the portion of the medical device and the particular location within the cardiac cavity, the second location other than the first location, and the second distance different than the first distance.

20. The medical system of claim 1, wherein the data processing device system is configured by the program at least to cause the changing of the particular graphical attribute set of the graphical annotation set at least in response to the movement of the at least the portion of the medical device within the cardiac cavity from the first location in the cardiac cavity at least by changing a size, a color, or a degree of transparency of at least a first graphical annotation in the graphical annotation set.

21. The medical system of claim 1, wherein the changing of the particular graphical attribute set of the graphical annotation set at least in response to the movement of the at least the portion of the medical device within the cardiac cavity from the first location in the cardiac cavity causes, via the input-output device system, at least a graphical removal of at least a first graphical annotation in the graphical annotation set.

22. The medical system of claim 1, wherein the graphical representation of the particular volume within the cardiac cavity comprises a map including a two-dimensional graphical representation of at least part of the particular volume within the cardiac cavity.

23. The medical system of claim 1, wherein the graphical representation of the particular volume within the cardiac cavity includes a map that maps three dimensional spatial coordinates of at least part of the particular volume within the cardiac cavity onto a two-dimensional coordinate frame.

24. The medical system of claim 1, wherein the particular graphical representation includes a map that maps three-dimensional spatial coordinates of various sub-portions of the at least the portion of the medical device onto a two-dimensional coordinate frame.

25. The medical system of claim 1, wherein the particular volume within the cardiac cavity corresponds to at least part of a volume occupied by the at least the portion of the medical device.

26. The medical system of claim 1, wherein the graphical representation of the particular volume within the cardiac cavity includes a three-dimensional graphical representation of the particular volume within the cardiac cavity mapped onto a two-dimensional coordinate frame.

27. The medical system of claim 1, wherein, at least in a state in which the particular graphical representation is caused to be annotated to include the graphical annotation set having the particular graphical attribute set, the graphical annotation set having the particular graphical attribute set corresponds to a second location within the patient, and wherein, the changing of the particular graphical attribute set of the graphical annotation set occurs while the graphical annotation set, which is annotated to the particular graphical representation, graphically remains in correspondence with the second location within the patient.

28. The medical system of claim 27, wherein the second location within the patient is a location within the cardiac cavity.

29. The medical system of claim 27, wherein the second location within the patient is a location on a tissue surface in the cardiac cavity.

30. The medical system of claim 27, wherein the second location within the patient is a location of a pulmonary vein of the cardiac cavity.

31. The medical system of claim 1, wherein, at least in the state in which the at least the portion of the medical device is located at the first location within the cardiac cavity, the graphical annotation set having the particular graphical attribute set corresponds to a second location within the patient, and wherein, the changing of the particular graphical attribute set of the graphical annotation set occurs while the graphical annotation set, which is annotated to the particular graphical representation, graphically remains in correspondence with the second location within the patient.

32. The medical system of claim 1, wherein the input-output device system comprises a catheter-device-location tracking system, and wherein the first location within the cardiac cavity is indicated by a location signal set provided by the catheter-device-location tracking system.

33. The medical system of claim 1, wherein the first location within the cardiac cavity is a location where the at least the portion of the medical device contacts a tissue surface in the cardiac cavity.

34. A method executed by a data processing device system according to a program stored by a communicatively con-nected memory device system, the data processing device system also communicatively connected to an input-output device system, and the method comprising:

causing, via the input-output device system, display of a particular graphical representation including a graphical representation of a particular volume within a cardiac cavity of a patient;

causing, via the input-output device system, the particular graphical representation to be annotated to include a graphical annotation set having a particular graphical attribute set at least in a state in which at least a portion of a medical device is located at a first location within the cardiac cavity; and causing, via the input-output device system and at least in response to a movement of the at least the portion of the medical device within the cardiac cavity from the first location within the cardiac cavity, a changing of the particular graphical attribute set of the graphical annotation set while the graphical annotation set, which is annotated to the particular graphical representation, graphically remains in correspondence with a same location within the patient.

35. One or more non-transitory computer-readable storage mediums storing a program executable by a data processing device system communicatively connected to an input-output device system, the program comprising:

display instructions configured to cause, via the input-output device system, display of a particular graphical representation including a graphical representation of a particular volume within a cardiac cavity of a patient;

annotation instructions configured to cause, via the input-output device system, the particular graphical representation to be annotated to include a graphical annotation set having a particular graphical attribute set at least in a state in which at least a portion of a medical device is located at a first location within the cardiac cavity; and graphical attribute set changing instructions configured to cause, via the input-output device system and at least in response to a movement of the at least the portion of the medical device within the cardiac cavity from the first location within the cardiac cavity, a changing of the particular graphical attribute set of the graphical annotation set while the graphical annotation set, which is annotated to the particular graphical representation, graphically remains in correspondence with a same location within the patient.

* * * * *